US 6,723,512 B2

(12) United States Patent
Larocca et al.

(10) Patent No.: US 6,723,512 B2
(45) Date of Patent: *Apr. 20, 2004

(54) METHODS USING GENETIC PACKAGE DISPLAY FOR DETECTING AND IDENTIFYING PROTEIN-PROTEIN INTERACTIONS THAT FACILITATE INTERNALIZATION AND TRANSGENE EXPRESSION AND CELLS OR TISSUES COMPETENT FOR THE SAME AND METHODS FOR EVOLVING GENE DELIVERY VECTORS

(75) Inventors: David Larocca, Encinitas, CA (US); Paul Kassner, San Mateo, CA (US); Andrew Baird, San Diego, CA (US)

(73) Assignee: Selective Genetics Inc., San Diego, CA (US)

(*) Notice: Subject to any disclaimer, the term of this patent is extended or adjusted under 35 U.S.C. 154(b) by 186 days.

This patent is subject to a terminal disclaimer.

(21) Appl. No.: 09/866,073

(22) Filed: May 24, 2001

(65) Prior Publication Data

US 2002/0068272 A1 Jun. 6, 2002

Related U.S. Application Data

(63) Continuation-in-part of application No. PCT/US99/25361, filed on Oct. 29, 1999, which is a continuation-in-part of application No. 09/258,689, filed on Feb. 26, 1999, now Pat. No. 6,451,527, which is a continuation-in-part of application No. 09/193,445, filed on Nov. 17, 1998, now Pat. No. 6,589,730, which is a continuation-in-part of application No. 09/195,379, filed on Nov. 17, 1998, now Pat. No. 6,472,146, which is a continuation-in-part of application No. 09/141,631, filed on Aug. 28, 1998, now abandoned.

(60) Provisional application No. 60/057,067, filed on Aug. 29, 1997, now abandoned.

(51) Int. Cl.$^7$ .................... C12Q 1/68; C12Q 1/70; C12N 15/00; C07H 21/02
(52) U.S. Cl. ................ 435/6; 435/5; 435/69.1; 435/320.1; 435/DIG. 2; 435/DIG. 4; 435/DIG. 14; 435/DIG. 15; 435/DIG. 35; 536/23.1
(58) Field of Search ................ 435/5, 6, 69.1, 435/69.8, 320.1, DIG. 2, DIG. 4, DIG. 14, DIG. 15, DIG. 35; 536/23.1, 23.4, 25.32

(56) References Cited

U.S. PATENT DOCUMENTS

| | | | |
|---|---|---|---|
| 5,733,731 A | | 3/1998 | Schatz et al. ................. 435/6 |
| 6,054,312 A | * | 4/2000 | Larocca et al. ........... 435/320.1 |
| 6,323,004 B1 | | 11/2001 | Kang ......................... 435/69.1 |
| 6,448,083 B1 | * | 9/2002 | Larocca et al. ................ 435/5 |
| 6,451,527 B1 | * | 9/2002 | Larocca et al. ................ 435/6 |
| 6,472,146 B1 | * | 10/2002 | Larocca et al. ................ 435/5 |
| 6,589,730 B1 | * | 7/2003 | Larocca et al. ................ 435/5 |
| 2003/0148263 A1 | * | 8/2003 | Larocca et al. ................ 435/5 |

FOREIGN PATENT DOCUMENTS

| | | |
|---|---|---|
| EP | 0 585 287 B1 | 10/1999 |
| WO | WO 92/20791 | 11/1992 |
| WO | WO 95/34648 | 12/1995 |
| WO | WO 97/00271 | 1/1997 |
| WO | WO 97/06435 | 2/1997 |
| WO | WO 98/05344 | 2/1998 |
| WO | WO 98/39482 | 9/1998 |
| WO | WO 99/10485 | 3/1999 |

OTHER PUBLICATIONS

Barry et al., "Toward cell–targeting gene therapy vectors: Selection of cell–binding peptides from random peptide–presenting phage libraries," *Nature Medicine* 2(3): 299–305, 1996.

Dunn, "Mammalian cell binding and transfection mediated by surface–modified bacteriophage lambda," *Biochimie* 78: 856–861, 1996.

Goldman et al., "Targeted Gene Delivery to Kaposi's Sarcoma Cells via the Fibroblast Growth Factor Receptor," *Cancer Research* 57:1447–1451, 1997.

Hart et al., "Cell Binding and Internalization by Filamentous Phage Displaying Cyclic Arg–Gly–Asp–containing Peptide," *The Journal of Biological Chemistry* 269(17): 12468–12474, 1994.

Hart et al., "Filamentous Phage For Cell Targeting And Gene Delivery," *Journal of Cellular Biochemistry Supplement* 18A: p. 225, Abstract No. DZ 114, 1994.

Jespers et al., "λZLG6: a phage lambda vector for high–efficiency cloning and surface expression of cDNA libraries on filamentous phage," *Gene* 173:179–181, 1996.

Larocca et al., "Targeted Transduction of Mammalian Cells Using a FGF2 Modified Filamentous Bacteriophage," *Cancer Gene Therapy* 4(6): Abstract No. O–46, p. S24, 1997.

Larocca et al., "Targeted Gene Delivery to Mammalian Cells Via Fibroblast Growth Factor (FGF–2) Display Phage," *Cancer Gene Therapy* 5(6): Abstract No. PD–31, p. S10, 1998.

(List continued on next page.)

*Primary Examiner*—Padmashri Ponnaluri
(74) *Attorney, Agent, or Firm*—Seed Intellectual Property Law Group PLLC

(57) ABSTRACT

A genetic package display system and methodology for probing protein-protein interactions that lead to cell transduction, selecting and/or identifying internalizing ligands, target cells and tissues which internalize known or putative ligands, and cell transduction facilitating peptides is provided. A ligand displaying genetic package that carries a selectable marker (e.g., reporter, selection, etc.) and presents a ligand on its surface is utilized to identify internalizing ligands, tranduction facilitating peptides, and/or a variety of cells and tissue types for the ability to be successfully transduced by the ligand displaying genetic package. Also provided are methods for evolving a ligand displaying package to facilitate gene delivery or delivery of any desired agent (e.g., pharmaceutical, polypeptide, peptide, etc.) into a cell and/or targeting cellular compartments such as the nucleus, endosome, chloroplast, mitochondria, etc.

33 Claims, 18 Drawing Sheets

OTHER PUBLICATIONS

Larocca et al., "Targeting Bacteriophage to Mammalian Cell Surface Receptors for Gene Delivery," *Human Gene Therapy* 9:2393–2399, 1998.

Larocca et al., "Gene Transfer to Mammalian Cells Using Genetically Targeted Filamentous Bacteriophage," *FASEB J.* 13:727–734, 1999.

Pasqualini and Ruosiahti, "Organ Targeting in vivo Using Phage Display Peptide Libraries," *Nature* 380: 364–366, 1996.

Russell, "Peptide–displaying phages for targeted gene delivery," *Nature Medicine* 2(3): 276–277, 1996.

Sawyer et al., "Methodology for selection of human antibodies to membrane proteins from a phage–display library," *Journal of Immunological Methods* 204: 193–203, 1997.

Sosnowski et al., "Targeting DNA to Cells with Basic Fibroblast Growth Factor (FGF2)," *The Journal of Biological Chemistry* 271(52): 33647–33653, 1996.

Souriau et al., "A Simple Luciferase Assay for Signal Transduction Activity Detection of Epidermal Growth Factor Displayed on Phage," *Nucleic Acids Research* 25(8): 1585–1590, 1997.

Spada and Plückthun, "Selectively infective phage (SIP) technology: A novel method for in vivo selection of interacting protein–ligand pairs," *Nature Medicine* 3(6): 694–696, 1997.

Voiculescu, "Aspecte ale interrelatiilor bacteriofagi–celule cucariote," *Bacteriologia, Virusologia, Parazitologia, Epidemiologia XXII*(3): 141–148, 1977 (+English Translation).

Yokoyama–Kobayashi and Kato, "Recombinant f1 Phage Particles Can Transfect Monkey COS-7 Cells by DEAE Dextran Method," *Biochemical And Biophysical Research Communications* 192(2): 935–939, 1993.

\* cited by examiner

METHODS USING GENETIC PACKAGE DISPLAY FOR DETECTING AND IDENTIFYING PROTEIN-PROTEIN INTERACTIONS THAT FACILITATE INTERNALIZATION AND TRANSGENE EXPRESSION AND CELLS OR TISSUES COMPETENT FOR THE SAME AND METHODS FOR EVOLVING GENE DELIVERY VECTORS

CROSS REFERENCE TO RELATED APPLICATIONS

The present application is a continuation-in-part of PCT Application No. PCT/US99/25361, published May 25, 2000 and filed Oct. 29, 1999 (now converted); which application claims priority to U.S. application Ser. No. 09/258,689, filed Feb. 26, 1999 (now issued as U.S. Pat. No. 6,451,527); which application is a continuation-in-part of U.S. application Ser. Nos. 09/193,445 (now issued as U.S. Pat. No. 6,589,730) and 09/195,379 (Now issued as U.S. Pat. No. 6,472,146), both filed Nov. 17, 1998; which are continuation-in-part applications of U.S. application Ser. No. 09/141,631, filed Aug. 28, 1998 (now abandoned); which application claims priority to U.S. Provisional Application No. 60/057,067, filed Aug. 29, 1997 (now abandoned).

TECHNICAL FIELD

This invention relates generally to genetic package display (e.g., phage display), and in particular, to selection of ligands that bind to a cell surface receptor and internalize useful in gene therapy, screening, and in various methodologies. The methods described herein are also referred to as Ligand Identification Via Expression or "LIVE™".

BACKGROUND OF THE INVENTION

Bacteriophage expressing a peptide on its surface has been used to identify protein binding domains, including antigenic determinants, antibodies that are specifically reactive, mutants with high affinity binding, identify novel ligands, and substrate sites for enzymes. In its most common form, a peptide is expressed as a fusion protein with a coat protein of a filamentous phage. This results in the display of the foreign protein on the surface of the phage particle. Libraries of phages are generated that express a multitude of foreign proteins. These libraries are bound to a substrate or cell that presents the binding partner of interest. This screening process is essentially an affinity purification. Bound phage are recovered, propagated, and the gene encoding the foreign protein may be isolated and characterized. This technology is commonly referred to as "phage display."

Through a process called "biopanning," the specific phage carrying a peptide or protein that interacts with a protein or other moiety on a solid phase can be identified and isolated. However, in many applications, binding or binding affinity is not the sole critical parameter. For example, in gene therapy, a gene sequence needs to be introduced into a cell. In preferred methods, the gene sequence is targeted to particular cells by way of a ligand/cell surface receptor interaction. Thus, the ligand must not only bind to the cells but must also be internalized and lead to expression of the introduced nucleic acid sequence. A native ligand that is internalized, when used in a system for gene therapy may not be efficiently internalized or while internalized may not lead to gene expression. For example, both FGF2 and EGF are internalizing ligands. Further, while many ligands can be found to internalize many do not facilitate tranduction of the targeted cell, leaving the internalized nucleic acid sequence in a non-functional state.

Phage libraries can be screened for potentially internalizing ligands by biopanning on live cells and rescuing internalized phage from the cells after stripping off externally bound phage (e.g., acid elution). However, this method may result in recovery of undesired phage that bind very tightly or are only partially internalized. Moreover, phage that are internalized and subjected to proteases lose infectivity and can not be recovered.

Generally speaking, the selection of ligands from phage display libraries or other genetic packages relies on peptide affinity and avidity. The number of phage recovered is determined by the complexity of the library, the target protein, and the selection stringency. Accordingly, prior to the present invention three types of selection (shown in FIG. 1) have been evaluated over the last several years: 1) affinity selection against simple targets like immobilized proteins; 2) affinity selection against complex targets such as the cell surface; and 3) selection after phage processing such as their internalization by cells.

When utilizing affinity selection, unbound phage are washed away with buffers of different stringencies and the remaining attached phage particles are recovered, amplified in bacteria, and then further enriched by repeated rounds of adsorption and recovery. In early rounds of selection, specific binding phage may be present among millions, if not billions, of other phage particles depending on the complexity of the library. While the phage recovered may be present in extremely low concentrations, they must be recovered in an infective form in order to allow for amplification by infecting host bacteria. As the selection is repeated, the library is significantly reduced in complexity and phage encoding the binding ligands can then be characterized by DNA sequencing.

With the success of ligand selection using phage libraries screened against immobilized proteins, investigators next began to select against whole cells Hoogenboom et al., European J. of Biochem. 260:774–784, 1999; Szardenings et al., J. Biol. Chem. 272(44):27943–27948, 1997; Pereira et al., J. Immunol Meth 203(1):11–24, 1997; Pasqualini et al., Nature 380:364–366, 1996. A clear advantage of this kind of "biopanning" is that little or no prior knowledge of the target molecule (i.e. a receptor) is needed and it can be in its native form on the cell surface. But the fact that the target protein may be low in concentration relative to the other cell surface proteins presents a significant disadvantage to selection and as in affinity selection against immobilized targets, non-specifically adherent phage can give false positive signals. A low concentration of non-specific phage can interfere in the early rounds of selection when the true binders are in extremely low concentrations.

Despite these issues, the selection of peptides on complex targets has been successful. Recent studies by Pasqualini's laboratory, have extended this approach even further by demonstrating that organ homing peptides can be selected from libraries that are "biopanned" in-vivo. By applying standard phage display selection techniques to mice, in-vivo, they identified peptides capable of selectively targeting phage to the vasculature of different organs including, brain, prostate, and kidney. Pasqualini and Ruoslahti, Mol. Psychiatry 1(6):423, 1996.

In an effort to increase selection stringency and overcome the problems of non-specific adsorption that are associated with biopanning against whole cells, alternative strategies have been explored. Hart et al. initially demonstrated that RGD targeted phage are internalized through receptor mediated endocytosis. *J. Biol. Chem.* 269(17):12468–12474, 1994 Subsequently, Barry et al. showed that cell-specific internalizing peptides can be selected from large diverse libraries of displayed peptides by washing phage off the cell surface at low pH and recovering internalized phage from cell lysates. *Nat. Med.* 2:299–305, 1996. However, these methods suffered from multiple steps as well as having no clear ability to determine in an initial screen which ligands would facilitate gene transduction and which would not. The original rationale behind selection by internalization was merely to increase the stringency of selection and therefore increase the ratio of signal to background.

Accordingly, current methodologies are inadequate to determine the usefulness of ligands for facilitating transfer and transduction of a cell by a nucleic acid molecule associated with the genetic package and ligand.

Further, identification of target cells or tissues that are able to internalize ligands and express a transgene would readily allow one to identify specific target cells for known or putative ligands as well as allow one to identify ligands for specific cell or tissue types. However, current methods of target cell identification are hampered by the same difficulties, as noted above, with regard to screening for internalizing ligands. Accordingly, current methodologies are inadequate to determine which cell or tissue types are useful targets for ligand mediated gene transfer.

Thus, current screening methods are inadequate for selecting peptide or protein ligands that bind to a cell surface receptor, internalize and lead to expression of the carried nucleic acid molecule. The present invention discloses display methods that select peptide or protein ligands that internalize and facilitate cell transduction and expression of product from an associated nucleic acid molecule, and further provides other related advantages.

SUMMARY OF THE INVENTION

The present invention utilized novel genetic package display of putative ligands to investigate the ability of these molecules to facilate cellular transduction with associated nucleic acid molecules, while also providing a functional genomic benefit, in that a variety of sequences can be screened for their ability to successfully deliver a reporter gene or other nucleic acid molecule to a cell by analyzing expression of that nucleic acid molecule. The finding that this could be achieved is quite surprising as many genetic packages, including filamentous phages were thought to be too large to pass through an endosomal pathway and even if they did, it seemed unlikely that a bacterial virus could traffic appropriately through the endosomal environment, uncoat and express their single-stranded DNA in a mammalian cell. Barry et al. (supra) Remarkably, however, as demonstrated herein, significant levels of gene transfer are obtained when phage and are targeted to mammalian cells.

In principle, the genetic selection of functional ligands by the methods set forth herein represents a significant departure from traditional biopanning (see Table 1) because it increases the stringency of selection by requiring the displayed ligand to bind, internalize, taffick to the desired cellular location and deliver a selectable genetic marker. This increased stringency decreases background from phage displaying simple binding proteins. In addition, biopanning relies on the recovery of infective phage, whereas, selection by the methods described herein does not require the presence of infective phage. Therefore, the present methods allow one to recover phage that are subjected to proteolytic cleavage after internalization that would otherwise be lost during biopanning. Moreover, because selection used in the present invention is genetic, a stable inherited change in the cell (e.g., marker expression) can be used as the basis for selection. Thus, for example, it is feasible that stable cell colonies could be used to directly identify rare phage internalization events in one round of screening.

TABLE 1

Comparison of phage selection on cells using Biopanning versus LIVE ™.

| Biopanning and/or Internalization Screening | LIVE ™ |
|---|---|
| Selects by affinity or internalization | Selects by internalization and gene transfer |
| Requires recovery of infective phage | Does not require infective phage for identification and further analysis. |
| High background from adherent phage | Low background from adherent phage |
| Selection transitory | Can select cells having stable genetic change (e.g., marker expression/drug resistance) |

Accordingly, through the use of the present invention one of ordinary skill in the art could functionally assess a variety of displayed peptides, polypeptides, etc. for the ability to facilitate internaliztion and genetic transduction. Thus, a logical extension of this methodology is the use of these methods to functionally explore the existence of natural ligands present in existing libraries, such as those now deposited due to the human genome project. In this case, it is the cell surface, itself, that selects the "most fit" ligand by their ability to stimulate receptor mediated endocytosis and subsequent phage transduction. The identification of novel ligands and their receptors using the present methodologies is likely to lead to new drugs and drug targets because cell-surface interacting ligands effect critical cellular processes like cell growth and differentiation. After all, natural ligands having direct clinical utility are the leading therapeutic products in biotechnology (e.g., erythropoietin, growth hormone, IL-2, GM-CSF). Yet, such ligands are the most difficult to mine from published genomic databases because they often exist as small fragments contained in much larger genes that are processed in a cell specific fashion.

Further, the present invention lends itself to the discovery of ligands useful for more traditional therapeutics. For example, once a sequence is identified that facilitates genetic transduction this ligand could be used to target small molecules (e.g., pharmaceutical drugs) to the nucleus of a cell or to other "targeted" areas within a cell thus increasing the therapeutic efficacy of the associated drug.

Within one aspect of the present invention, a method of selecting internalizing ligands displayed on a genetic package is presented, comprising: (a) contacting a ligand displaying genetic package(s) with a cell(s), wherein the package carries a gene encoding a detectable product which is expressed upon internalization of the package; and (b) detecting product expressed by the cell(s); thereby selecting internalizing ligands displayed on a genetic package.

In another aspect, the invention provides a method of identifying an internalizing ligand displayed on a genetic package, comprising: (a) contacting one or more ligand displaying genetic packages with a cell(s), wherein each package carries a gene encoding a selectable marker which is expressed upon internalization of the package, (b) detecting the selectable marker expressed by the cell(s); and (c) recovering a nucleic acid molecule encoding an internalizing ligand from the cell(s) expressing the product, and thereby identifying an internalizing ligand displayed on a genetic package.

In yet another aspect, the invention provides a method of identifying an internalizing ligand displayed on a genetic package, comprising: (a) contacting one or more ligand displaying genetic packages with a cell(s), wherein each package carries a gene encoding a selectable product which is expressed upon internalization of the package, (b) incubating the cell(s) under selective conditions; and (c) recovering a nucleic acid molecule encoding an internalizing ligand from the cell(s) which grow under the selective conditions; thereby identifying an internalizing ligand displayed on a genetic package.

In yet another aspect, a method is provided for a high throughput method of identifying an internalizing ligand displayed on a genetic package, comprising: (a) contacting one or more ligand displaying genetic packages with a cell(s) in an array, wherein each package carries a gene encoding at least one detectable product which is expressed upon internalization of the package; and (b) detecting product(s) expressed by the cell(s) in the array, and thereby identifying an internalizing ligand displayed on a genetic package. In one embodiment, the ligand displaying package comprises a library of ligand displaying packages.

In another aspect, the present invention provides a method of identifying an internalizing ligand displayed on a genetic package, comprising: (a) contacting one or more ligand displaying a genetic packages with a cell(s), wherein each package carries a selectable marker which is detectable upon internalization of the package, (b) detecting the selectable marker internalized by the cells; and (c) recovering a nucleic acid molecule encoding an internalizing ligand from the cell(s) carrying the selectable marker, thereby identifying an internalizing ligand displayed on a genetic package.

Within one aspect of the present invention, a method of selecting internalizing ligand/anti-ligand pairs is presented, comprising: (a) contacting a ligand displaying genetic package(s) with a cell(s), wherein the package carries a gene encoding a detectable product which is expressed upon internalization of the package; and (b) detecting product expressed by the cell(s); thereby selecting ligand/anti-ligand pairs.

In another aspect, the invention provides a method of identifying a ligand or anti-ligand of an internalizing ligand/anti-ligand pair, comprising: (a) contacting one or more ligand displaying genetic packages with a cell(s), wherein each package carries a gene encoding a detectable product which is expressed upon internalization of the package, and wherein the cell(s) expresses an anti-ligand-receptor fusion protein on its surface; (b) detecting product expressed by the cell(s); and (c) recovering a nucleic acid molecule encoding an internalizing ligand and/or a nucleic acid molecule encoding an internalizing anti-ligand from the cell(s) expressing the product, and thereby identifying a ligand or anti-ligand of a internalizing ligand/anti-ligand pair.

In yet another aspect, the invention provides a method of identifying a ligand or anti-ligand of an internalizing ligand/anti-ligand pair, comprising: (a) contacting one or more ligand displaying genetic packages with a cell(s), wherein each package carries a gene encoding a detectable product which is expressed upon internalization of the package, and wherein the cell(s) expresses an anti-ligand-receptor fusion protein on its surface; (b) incubating the cell(s) under selective conditions; and (c) recovering a nucleic acid molecule encoding an internalizing ligand and/or a nucleic acid molecule encoding an internalizing anti-ligand from the cell(s) which grow under the selective conditions; thereby identifying a ligand or anti-ligand of a internalizing ligand/anti-ligand pair.

In yet another aspect, a method is provided for a high throughput method of identifying a ligand or anti-ligand of an internalizing ligand/anti-ligand interactions, comprising: (a) contacting one or more ligand displaying genetic packages with a cell(s) in an array, wherein each package carries a gene encoding at least one detectable product which is expressed upon internalization of the package; and (b) detecting product(s) expressed by the cell(s) in the array, and thereby identifying a ligand or anti-ligand of a internalizing ligand/anti-ligand interactions. In one embodiment, the array contains cells expressing a library of anti-ligand-receptor fusion proteins. In another embodiment, the ligand displaying package comprises a library of ligand displaying packages.

Within one aspect of the present invention, a method of identifying a target cell or tissue for internalizing ligands is presented, comprising: (a) contacting a library of ligand displaying genetic packages with a cell(s) or tissue(s), wherein each package carries a gene encoding a detectable product which is expressed upon internalization of the package; and (b) detecting product expressed by the cell(s) or tissue(s), and thereby identifying a target cell or tissue for internalizing ligands.

In another aspect, the invention provides a method of selecting an internalizing ligand for a selected target cell or tissue within a pool of target cells or tissues and identifying a target cell or tissue for the internalizing ligand, comprising: (a) contacting a library of ligand displaying genetic packages with a pool of cell(s) or tissue(s), wherein each package carries a gene encoding a selectable marker which is expressed upon internalization of the package; (b) detecting the selectable marker expressed by the cell(s) or tissue (s); and (c) recovering a nucleic acid molecule encoding an internalizing ligand from a selected set of cell(s) or tissue(s) within the pool expressing the product.

In yet another aspect, the invention provides a method of selecting an internalizing ligand for a selected target cell or tissue within a pool of target cells or tissues and identifying a target cell or tissue for the internalizing ligand, comprising: (a) contacting a library of ligand displaying genetic packages with a pool of cell(s) or tissue(s), wherein each package carries a gene encoding a detectable product which is expressed upon internalization of the package; (b) incubating the cell(s) or tissue(s) under selective conditions; and (c) recovering a nucleic acid molecule encoding an internalizing ligand from a selected set of cell(s) or tissue(s) within the pool which grow under the selective conditions; thereby selecting internalizing ligands and identifying a target cell or tissue for the internalizing ligand.

In yet another aspect, a method is provided for a high throughput method of identifying target cells or tissues for internalizing ligands, comprising: (a) contacting a library of ligand displaying genetic packages with cells or tissue in an array, wherein each package carries a gene encoding at least one detectable product which is expressed upon internalization of the package; and (b) detecting product(s) expressed by the cells or tissue in the array; thereby identifying target cells or tissues for internalizing ligands. In one embodiment, the array contains a variety of cell types. In another embodiment, the method further comprises step (c), wherein the library is a library of ligand displaying bacteriophages that is repeatedly divided into subset pools and screened using steps (a) and (b) until a specific bacteriophage expressing an internalizing ligand is identified.

In yet additional embodiments a medicament for gene therapy is provided, comprising an internalizing ligand identified by the of the present invention. Also provided are anti-bacterial agents comprising an internalizing ligand identified by the methods of the present invention.

Also provided are methods for identifying transduction facilitating peptides, comprising: (a) contacting one or more ligand displaying a genetic packages with a cell(s), wherein each package displays a putative transduction facilitating peptide and a ligand known to internalize, and wherein each package carries a selectable marker which is detectable upon internalization of the package, (b) detecting the selectable marker internalized by the cells; and (c) recovering a nucleic acid molecule encoding an internalizing ligand from the cell(s) carrying the selectable marker, and thereby identifying an internalizing ligand displayed on a genetic package.

In related embodiments, the selectable marker is selected from reporter gene expression, expression of a gene that confers the ability to permit cell growth under selection conditions, non-endogenous nucleic acid sequences that permit PCR amplification, and nucleic acid sequences that can be purified by protein/DNA binding.

In preferred embodiments, the ligand displaying genetic package comprises a bacteriophage. The bacteriophage are filamentous phage or lambdoid phage in other preferred embodiments. In some embodiments, the bacteriophage carries a genome vector. In other embodiments, the bacteriophage carries a hybrid vector.

In other embodiments, the library is a cDNA library, an antibody gene library, a random peptide gene library, or a mutein library. In other preferred embodiments, the detectable product is selected from the group consisting of green fluorescent protein, β-galactosidase, secreted alkaline phosphatase, chloramphenicol acetyltransferase, luciferase, human growth hormone and neomycin phosphotransferase.

In other embodiments, the cells may be isolated by flow cytometry, for example. In further embodiments, the methods further comprise recovering a nucleic acid molecule encoding the ligand from the cell(s) expressing the product. Also provided are methods for enhancing transduction by utilizing genotoxic agents, heat shock, and transduction facilitating peptides.

In certain embodiments, PCR or Hirt extraction methods are used to recover the internalized nucleic acid molecules.

These and other aspects of the present invention will become evident upon reference to the following detailed description and attached drawings. In addition, various references are set forth below which describe in more detail certain procedures or compositions (e.g., plasmids, etc.), and are therefore incorporated herein by reference in their entirety.

BRIEF DESCRIPTION OF THE DRAWINGS

FIG. 1A depicts the parent phage vector with wild type pIII coat protein. The base vector is M13 genome with ampicillin resistance (Amp$^R$) gene and GFP expression cassette inserted into the intergenic region between pIV and pII (MEGFP3). The MEGFP3 vector contains the following elements: ori-CMV, SV40 replication origin and CMV promoter; EGFP, enhanced green fluorescent protein gene; BGH, and a bovine growth hormone polyadenylation sequence. FIG. 1B represents the FGF-pIII fusion display phage (MF2/1G3).

FIG. 3A depicts the amount of phage protein detected using both the empty MEGFP3 (i.e., MG3) vector and the FGF2 fusion construct (FGF2-MEGFP). FIG. 3B depicts the amount of FGF2 detected on the phage having the fusion construct.

DETAILED DESCRIPTION OF THE INVENTION

As noted above, the present invention provides methods of using ligand displaying genetic packages to identify protein-protein interactions, ligands that bind and internalize and lead to genetic transduction of a marker nucleic acid molecule or that to identify target cells and/or tissues for known or putative ligands and to identify transduction facilitating peptides. While it should be understood that a variety of ligand display methods may be utilized (e.g., phage display, RNA-peptide fusions, and ligand displaying bacteria), the present invention uses bacteriophage ligand display to exemplify the various embodiments.

Figure 1A:
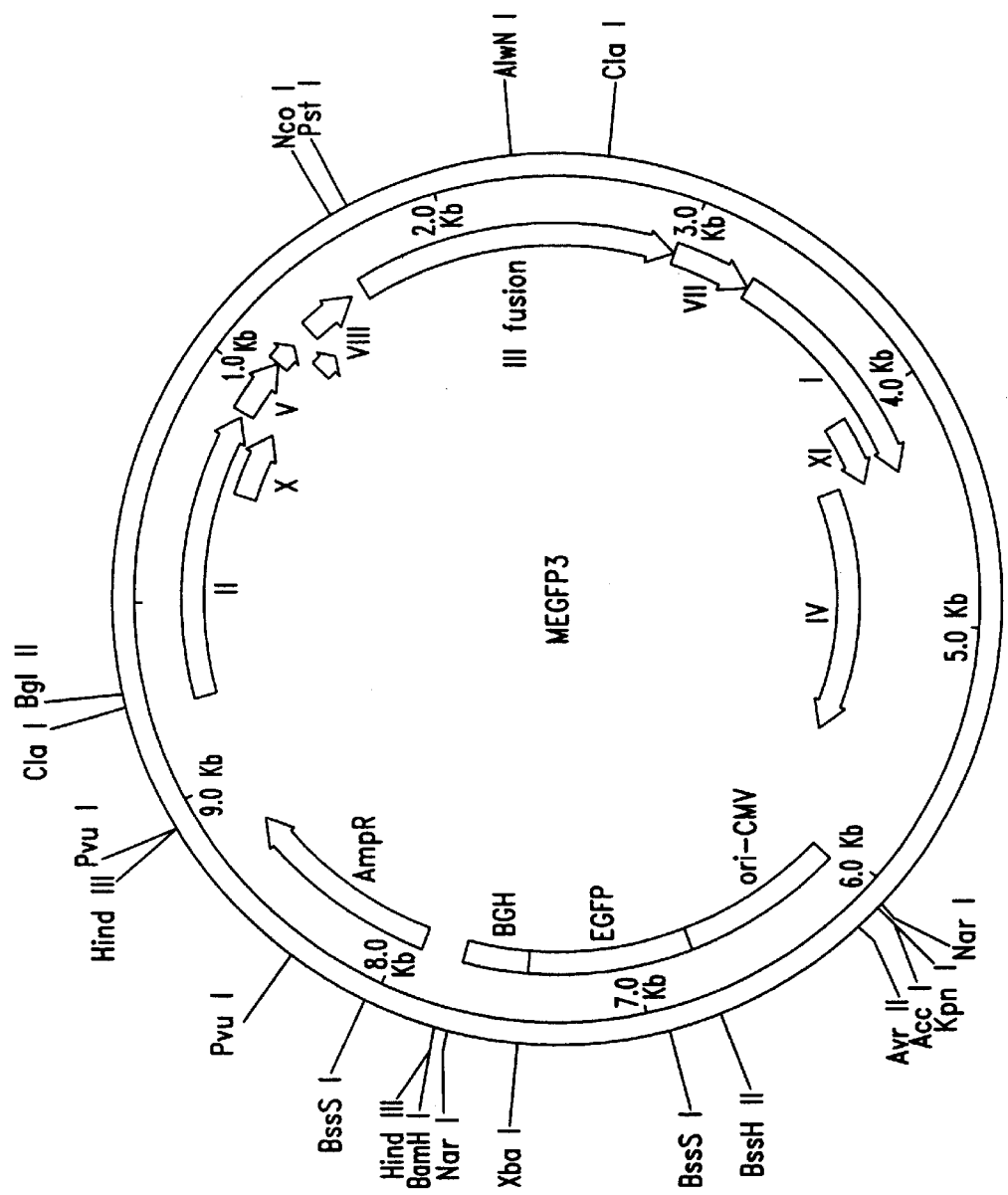
FIGS. 1A and 1B are schematic representations of phage vectors for mammalian cell transduction.

Briefly, in one embodiment of the present invention, a library of antibodies, cDNAs, or genes encoding random peptides is cloned into a coat protein of a ligand displaying genetic package (e.g., gene III protein of filamentous phage) is utilized. The phage genome also contains an "expression cassette" encoding a transgene/marker nucleic acid molecule placed downstream from a cell promoter that is active in the cells to be infected (FIG. 1A). The transgene is generally a selectable gene product and/or a detectable marker. Phage are contacted with test cells and expression of the transgene is monitored or selected. Desirable genetic packages, such as phage that internalize and lead to transgene expression will confer the phenotype of the transgene, such as drug resistance or expression of a fluorescing protein. The cells may be isolated on the basis of transgene expression. For example, when the transgene is a drug resistance gene, cells are grown in the presence of the drug, such that only those cells receiving and expressing the transgene are propagated. The gene(s) that are fused with the coat protein and that promoted cell binding, internalization, and transgene expression are recovered from the selected cells by a suitable method.

I. Display Packages

A variety of ligand displaying genetic packages may be used within the context of the present invention. A "ligand displaying genetic package" as used herein, refers to any package which comprises a peptide/protein ligand and carries a nucleic acid molecule capable of detection, once internalized in the target cell. In one embodiment, a nucleic acid carried by the ligand displaying genetic package is expressed upon internalization into the cell thereby allowing for recovery and detection of an internalized genetic package. In other embodiments, the ligand displaying genetic package may carry a nucleic acid molecule which allows for detection via PCR of unique sequences, the Hirt extraction method, or by the ability of the internalized nucleic acid sequences to bind non-endogenous DNA binding proteins (e.g., nucleic acid sequence could comprise a lac operon, thereby allowing for lac repressor binding). Accordingly, display may be by a virus, RNA-peptide fusions, bacteriophage, bacteria, or similar system (See, Phage Display of Peptides and Proteins, pages 151–193, Kay (Ed.), *Academic Press*, San Diego, 1996). Certain specific embodiments described herein utilize bacteriophage. Such phage include the filamentous phages, lambda, T4, MS2, and the like. A preferred phage is a filamentous phage, such as M13 or f1. Accordingly, many illustrations, while exemplifying the use of phage, could also be performed with any ligand displaying genetic package.

Phage that present the foreign protein or peptide as a fusion with a phage coat protein are engineered to contain the appropriate coding regions. A variety of bacteriophage and coat proteins may be used. Examples include, without limitation, M13 gene III, gene VI, gene VII, gene VIII, and gene IX; fd minor coat protein pIII (Saggio et al., *Gene* 152:35, 1995); lambda D protein (Sternberg and Hoess, *Proc. Natl. Acad. Sci. USA* 92:1609, 1995; Mikawa et al., *J. Mol. Biol.* 262:21, 1996); lambda phage tail protein pV (Maruyama et al., *Proc. Natl. Acad. Sci. USA* 91:8273, 1994; U.S. Pat. No. 5,627,024); fr coat protein (WO 96/11947; DD 292928; DD 286817; DD 300652); φ29 tail protein gp9 (Lee, *Virol.* 69:5018, 1995); MS2 coat protein; T4 small outer capsid protein (Ren et al., *Protein Sci.* 5:1833, 1996), T4 nonessential capsid scaffold protein IPIII (Hong and Black, *Virology* 194:481, 1993), or T4 lengthened fibritin protein gene (Efimov, *Virus Genes* 10:173, 1995); PRD-1 gene III; Qβ3 capsid protein (as long as dimerization is not interfered with); and P22 tailspike protein (Carbonell and Villaverde, *Gene* 176:225, 1996). Techniques for inserting foreign coding sequence into a phage gene sequences are well known (see e.g., Sambrook et al., *Molecular Cloning: A Laboratory Approach*, Cold Spring Harbor Press, NY, 1989; Ausubel et al., *Current Protocols in Molecular Biology*, Greene Publishing Co., NY, 1995).

In the preferred filamentous phage system, a wide range of vectors are available (see, Kay et al., Phage Display of Peptides and Proteins: A Laboratory Manual, Academic Press, San Diego, 1996). The most common vectors accept inserts in gene III or gene VIII. Furthermore, the foreign gene can be inserted directly into the phage genome or into a phagemid vector. Methods of propagation of filamentous phage and phagemids are well known.

Filamentous phage vectors generally fall into two categories: phage genome and phagemids. Either type of vector may be used within the context of the present invention. Many such commercial vectors are available. For example, the pEGFP vector series (Clontech; Palo Alto, Calif.), M13mp vectors (Pharmacia Biotech, Sweden), pCANTAB 5E (Pharmacia Biotech), pBluescript series (Stratagene Cloning Systems, La Jolla, Calif.), pComb3 and M13KE (New England Biolabs), and others may be used. One particularly useful commercial phagemid vector is pEGFP-N1, which contains a green fluorescent protein (GFP) gene under control of the CMV immediate-early promoter. This plasmid also includes an SV40 origin of replication to enhance gene expression by allowing replication of the phagemid to high copy number in cells that make SV40 T antigen.

Other vectors are available in the scientific community (see e.g., Smith, in *Vectors: A Survey of Molecular Cloning Vectors and their Uses*, Rodriquez and Denhardt, eds., Butterworth, Boston, pp 61–84, 1988) or may be constructed using standard methods (Sambrook et al., *Molecular Biology: A Laboratory Approach*, Cold Spring Harbor, N.Y., 1989; Ausubel et al., *Current Protocols in Molecular Biology*, Greene Publishing, NY, 1995) guided by the principles discussed below.

The source of the ligand (e.g., gene, gene fragment, peptide encoding nucleic sequence, chemically conjugated peptide or protein, non-covalently conjugated peptide or protein) may be for example, derived from a cDNA library, antibody library or random peptide library. Alternatively, the ligand may be from a library of random or selective mutations of a known ligand. In an additional alternative, the ligand may be from a library of known receptor or cell surface binding agents. For example, the library may contain a subset of peptides known to bind the FGF or EGF receptor, but that have unknown gene delivery and expression characteristics (i.e., transduction capacity). Further, the ligand may be from a library of single chain antibodies, Fab fragments and other antibody fragments. Virtually any peptide or polypeptide that can be attached to the surface via covalent or non-covalent attachment or via genetic fusion of the nucleic acid sequence encoding the peptide or polypeptide of interest as a putative ligand. Other ligands may include randomly or selectively cleaved protein fragments.

When a cDNA library is used, the starting cDNA is synthesized from mRNA isolated from the source tissue or cell line from which the desired ligand originates. cDNA is then amplified using primers containing sequences of appropriate restriction enzyme sites for insertion into the desired vector. Alternatively, commercially available cDNA libraries (e.g., Clontech; Palo Alto, Calif.) may be amplified for insertion into the vector.

Similarly, libraries of antibody fragments can be made from mRNA isolated from the spleen cells of immunized animals (immunized for example with whole target cells or membranes) or subcloned from existing antibody libraries from immunized or naive animals. Random peptide encoding sequences are subcloned from libraries that are commercially available (New England Biolabs; Mass.) or can be synthesized and cloned using previously described methods (see, Kay et al., supra).

Phage display libraries of random or selective mutations of known ligands (referred to herein as a "mutein library") for improved gene delivery are performed in the same manner as described for screening random peptide libraries. Random mutations of the native ligand gene may be generated using DNA shuffling as described by Stemmer (*Nature* 370:389–391, 1994). Briefly, in this method, the ligand is amplified and randomly digested with DNase I. The 50–300 base pair fragments are reassembled in an amplification performed without primers and using Taq DNA polymerase or similar enzyme. The high error rate of this polymerase introduces random mutations in the fragments that are reassembled at random thus introducing combinatorial variations of different mutations distributed over the length of the gene. Error prone amplification may alternatively be used to introduce random mutations (Bartell and Szostak, *Science*, 261:1411, 1993). The ligand may be mutated by cassette mutagenesis (Hutchison et al., in *Methods in Enzymology* 202:356–390, 1991), in which random mutations are introduced using synthetic oligonucleotides and cloned into the ligand to create a library of ligands with altered binding specificities. Additional mutation methods can be used. Some additional methods are described in Kay et al., supra. Further, selective mutations at predetermined sites may be performed using standard molecular biological techniques (Sambrook et al., *Molecular Cloning: A Laboratory Manual*, Cold Spring Harbor Press, 1989).

If a cDNA library cannot be generated because, for example, the source of the desired ligand is not available or is unknown, random peptide libraries or a cDNA library from placenta may be used as a starting point for screening. Methods for construction of random peptide libraries may be found, for example, in Kay et al., supra. Briefly, the random peptides are encoded by DNA assembled from degenerate oligonucleotides and inserted into one of the bacteriophage vectors described herein. Several different strategies may be used to generate random peptides or peptide encoding sequences. For example, triplets of NNN, wherein each N is an equimolar representation of all four nucleotides, will generate all 20 amino acids (as well as 3 stop codons). Alternative strategies use NN(G/T) and NN(G/C), which results in 32 codons that encodes all 20 amino acids and only 1 stop codon. Other strategies utilize synthesis of mixtures of trinucleotide codons representing all 20 amino acids and no stop codons. Once the oligonucleotides are synthesized, they are assembled as double strands by a variety of schemes, one of which involves synthesis of the complementary strand (see Kay et al., supra).

In addition to the ligand/coat protein fusion, in one embodiment, the vector may contain a gene whose product can be detected or selected for. As referred to herein, a "reporter or marker" gene is one whose product can be detected, such as by immunodetection, fluorescence, enzyme activity on a chromogenic or fluorescent substrate, and the like or selected for by growth conditions. Such reporter genes include, without limitation, green fluorescent protein (GFP), β-galactosidase, chloramphenicol acetyltransferase (CAT), luciferase, neomycin phosphotransferase, secreted alkaline phosphatase (SEAP), and human growth hormone (HGH). Selectable markers include drug resistances, such as neomycin (G418), hygromycin, and the like. However, the present invention is not limited to these markers as one of skill in the art could readily envision using any detectable product that allows one to distinguish an cell that wherein the transgene was introduced and/or expressed. For example, the gene or transgene may be a structural gene that is heterologous or endogenous to the host. If endogenous to the host, detection may be by comparison to a control of untreated cells.

The marker gene is in operative linkage with a promoter. Any promoter that is active in the cells to be transfected can be used. The vector should also have a viral origin of replication and a packaging signal for assembling the vector DNA with the capsid proteins.

Most applications of the present invention will involve transfection of mammalian cells, including human, canine, feline, equine, and the like. However, several embodiments of the present invention utilize expression in non-mammalian cells (e.g., fungal, yeast, bacteria, and plant). The choice of the promoter will depend in part upon the targeted cell type. Promoters that are suitable within the context of the present invention include, without limitation, constitutive, inducible, tissue specific, cell type specific, temporal specific, or event-specific, although constitutive promoters are preferred.

Examples of constitutive or nonspecific promoters include the SV40 early promoter (U.S. Pat. No. 5,118,627), the SV40 late promoter (U.S. Pat. No. 5,118,627), CMV early gene promoter (U.S. Pat. No. 5,168,062), bovine papilloma virus promoter, and adenovirus promoter. In addition to viral promoters, cellular promoters are also amenable within the context of this invention. In particular, cellular promoters for the so-called housekeeping genes are useful (e.g., β-actin). Viral promoters are generally stronger promoters than cellular promoters.

Additional promoters known and available to those of skill in the art may also be useful within the context of the present invention. For example, if display packages are to be used to transduce yeast, a yeast promoter will be required and are available in the context of a number of commercially available vectors from a variety of sources including Clontech, (Palo Alto, Calif.), and Invitrogen (Carlsbad, Calif.). Further, if transduction of bacteria is of interest a number of bacterial vectors are available of which most are derived from the pUC lineage. In addition, a variety of plant vectors and promoters are available, for example general descriptions of plant expression vectors and reporter genes can be found in Gruber et al., "Vectors for Plant Transformation, in Methods in Plant Molecular Biology & Biotechnology" in Glich et al., Eds. pp. 89–119, CRC Press, 1993. Promoters useful within the context of the present invention include both constitutive and inducible natural promoters as well as engineered promoters. Such promoters may be obtained from plants, viruses, or other sources, and include, but are not limited to: those described herein such as the 35S promoter of cauliflower mosaic virus (CaMV). Typically, for plant expression vectors, suitable promoters include the 35S RNA and 19S RNA promoters of CaMV (Brisson et al., *Nature* 310:511, 1984; Odell et al., *Nature* 313:810, 1985); the full-length transcript promoter from Figwort Mosaic Virs FMV) (Gowda et al., *J. Cell Biochem.* 13D: 301, 1989 and U.S. Pat. No. 5,378,619) and the coat protein promoter to TMV (Takamatsu et al., *EMBO J* 6:307, 1987). Alternatively, plant promoters such as the light-inducible promoter from the small subunit of ribulose bisphosphate carboxylase (ssRUBISCO) (Coruzzi et al., *EMBO J* 3:1671, 1984; Broglie et al., *Science* 224:838, 1984); mannopine synthase promoter (Velten et al., *EMBO J* 3:2723, 1984) nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley et al., *Mol. Cell. Biol.* 6:559, 1986; Severin et al., *Plant Mol. Biol.* 15:827, 1990) may be used. See PCT Publication WO 91/19806 for a review of a variety of known plant promoters which are suitable for use within the context of the present invention.

In preferred embodiments, the phage has an origin of replication suitable for the transfected cells. Viral replication systems, such as EBV ori and EBNA gene, SV40 ori and T antigen, or BPV ori, may be used. Other mammalian replication systems may be interchanged. As well, the replication genes may cause high copy number. Expression of therapeutic genes from the phage genome may be enhanced by increasing the copy number of the phage genome. In one method, the SV40 origin of replication is used in the presence of SV40 T antigen to cause several hundred thousand copy number. The T antigen gene may be already present in the cells, introduced separately, or included in the phage genome under the transcriptional control of a suitable cell promoter. Other viral replication systems for increasing copy number can also be used, such as EBV origin and EBNA.

As noted above, phagemid vectors may also be utilized in the practice of the present invention. Phagemid vectors are plasmid vectors that contain filamentous phage sequences and therefore can be packaged into phage particles when the complementing phage structural proteins are provided in trans by helper phage. In conventional phagemid systems both the phagemid and helper phage encode pIII coat protein. A combination of both wild type and pIII-fusion protein is displayed on the resulting phagemid particles with the phagemid encoding the pIII fusion and the helper encoding wild type pIII. This results in a monovalent display of peptides or proteins with often less than one recombinant pIII fusion protein displayed per phage particle. Many antibody libraries are made in phagemid vectors because monovalent display is advantageous for selecting high affinity antibodies over lower affinity antibodies which in a high valence system might be selected on the basis of avidity. While similar concerns may justify the use of monovalent display vectors in the practice of the present invention, current data suggests, however, that multivalent display is important for mammalian cell internalization. (Larocca et al., *FASEB J.* 13:727–734, 1999; Larocca et al., *Human Gene Therapy* 9:2393–2399, 1998; Becerril et al., *Biochem. Biophys. Res. Comm.* 255:386–393; Ivanenkov et al., *Biochim. Biophys. Acta* 1448:450–462, 1999). Thus, a phagemid vector with multivalent display would likely be more useful for selecting internalizing phage in mammalian cells.

Multivalency in a phagemid system may be provided by a variety of techniques including by rescuing with helper having a gIII deletion (or gVI, gVII, gVIII, gIX deletion or similar phage coat protein, depending on the phagemid). Accordingly, rescuing with a gIII deleted helper can alter the valency of phagemid vectors. Rakonjac and colleagues have developed host strains which allow production of the gIII deleted helper phage with very low background of gIII containing recombinants (as low as 1 in $10^9$). See, e.g., Rakonjac et al., *Gene* 198:99–103, 1997. In this system there is little or no wild type pIII provided by the helper phage so that each phage displays multiple copies of the pIII fusion derived from the phagemid. Thus, in one embodiment the present invention utilizes a vector containing the EGF-pIII fusion protein from the phage vector, MG4-EGF (the vector MG4 is constructed by reversing the orientation of the SV40ori/CMV/GFP expression cassette in the MEGFP3 (MG3) phage vector. MG4-EGF has the EGF encoding gene inserted "in-frame" at the pst1/Nco1 sites in MG4) and similarly the control vector containing the CMV/SV40ori/GFP cassette and the pIII gene from the control phage. The pIII genes are under the transcriptional control of the inducible lac promoter to minimize synthesis of pIII protein in the absence of a suitable inducer (i.e. IPTG).

Figure 17:
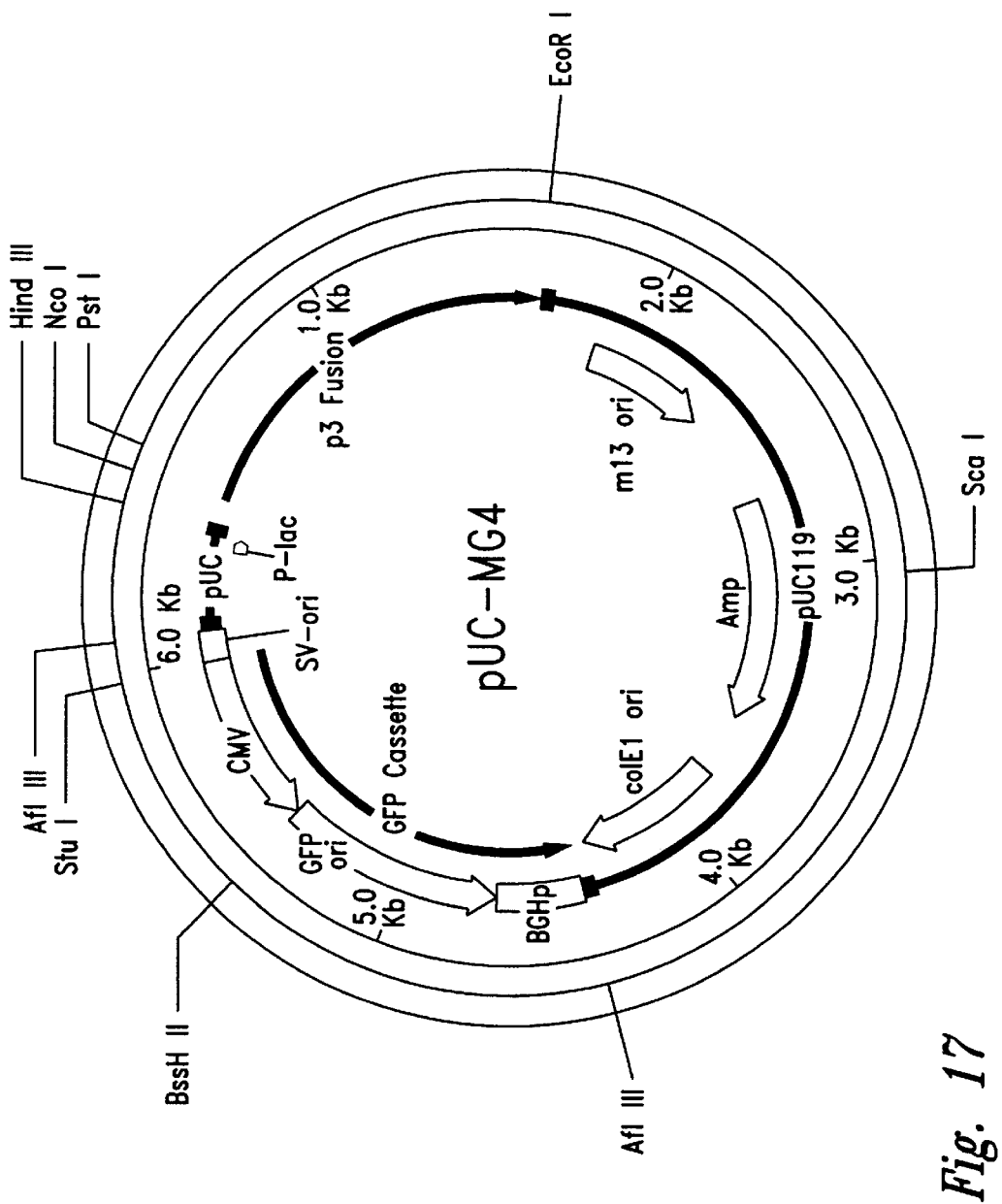
FIG. 17 is a vector map of a pUC-MG4 phagemid vector.

Construction and utilization of multivalent phagemid vectors is within the knowledge of those of skill in the art. Briefly, the backbone of the above phagemids can be easily constructed from pUC119 (purchased from ATTC) which contains an M13 phage origin of replication and an ampicillin resistance gene. The CMV/SV40ori/GFP gene is PCR amplified using primers that incorporate an AflIII endonuclease site and is inserted into the unique AflIII site in pUC119 to create pUC-GFP. The pIII and EGF-pIII fusion genes are subcloned from MG4 and MG4-EGF by PCR amplification using primers that encode HindIII and EcoR1 endonuclease sites and insertion into pUC-GFP at the unique HindIII and EcoR1 sites in the multicloning site to create pUC-MG4 (FIG. 17) and pUC-MG4-EGF. The phagemid DNA constructs are used to transform host bacteria (XL-1 Blue; Stratagene, San Diego, Calif.) that contain the lac IQ repressor protein gene to suppress expression of the pIII or EGF-pIII fusion gene in the absence of IPTG. Phagemid particles are rescued from transformed bacteria with a wild type helper phage (i.e. R408 or VCSM13) or a gIII deleted helper (i.e. R408d3 or VCSM13d3, Stratagene, San Diego, Calif.) and tested on COS1 cells for phage mediated transduction efficiency as measured by % GFP positive cells. The results of these experiments (not shown) indicate that the multivalent phage (VCSM13d3 rescued) are about 2 orders of magnitude more efficient at transducing COS1 cells than the monovalent display phagemid particles (wild type rescued). Western blot analysis (not shown) of CsCl phagemid particles reveals that about 50% of the pIII protein displayed on the VCSM13d3 rescued phagemid particles is fused to EGF; the remaining pIII protein is likely derived from a proteolytic cleavage of the fusion protein. Analysis of the monovalent phagemid particles shows that more than 66% of the displayed pIII is the length of wild type pIII and of MG4-EGF phage shows that 60–80% of the pIII displayed is full length. Accordingly, such data demonstrate that multivalent display of the targeting ligand facilitates uptake of the ligand targeted phage via cognate receptor mediated endocytosis and that it is feasible to construct and use a multivalent phagemid system for phage mediated mammalian cell transduction.

In yet further embodiments, ligand fusions to a truncated pIII, pVI, pVII, pVIII, pIX or other appropriate phage coat gene may be utilized. Several advantages become apparent when expressing displayed ligands as fusions to a truncated phage coat gene. For example, rescue by helper phage is simplified because there is no interference of phagemid derived pIII with the infection by helper phage. Thus multivalent phagemid yields will likely be increased by infection with helper phage after induction of the phagemid pIII fusion gene (not possible with fusions to full length pIII because of interference). Additionally some ligands may be more efficiently expressed as a fusion to truncated pIII.

Phagemid vectors having truncated fusions to pIII or pVIII are easily produced by those of ordinary skill in the art. Briefly, a phagemid vector is created with a pIII gene having only domain 2 of pIII (preferably starting from amino acids 198–250 and ending at amino acid 406), as described by Dottavio (in Phage Display of Peptides and Proteins, Kay et al. (Eds.) San Diego, Academic Press, 1998). When this phagemid is rescued with the R408d3 or VCSM13d3 helper phage the resulting phagemid particles are no longer infective in bacteria since domain 1 of pIII is required for infectivity. However these particles can be used for non-bacterial cell transduction and subsequent rescue of ligand encoding sequences as described herein. Further, to enhance ligand recognition it may be beneficial to fuse the sequence encoding the peptide or protein ligand or the peptide or protein ligand itself to domain 2 of pIII via a linker molecule (e.g., $gly_4ser$, heterobifunctional linkers, and the like).

In a further embodiment, a viral replication system such as an SV40 based shuttle vector can be used as the phagemid. Accordingly, cells infected by the ligand-expressing phage package the phagemid DNA into SV40 viral particles. These viral particles infect neighboring cells, thus spreading the phagemid DNA. Following growth in culture, a dish of cells contains millions of copies of the original phagemid, thereby enriching the population of internalized ligand encoding genetic packages several fold. The cell lines used with such a system can either be transfected with DNA sequences encoding SV40 small and large T-antigens or can contain the proteins through delivery with fusion constructs, such as VP22. VP22 is a herpes virus structural protein that is exported from cells and spreads to neighboring cells where it concentrates in the nucleus (Elliot and O'Hare, *Cell* 88:223–233, 1997). VP22-SV40 T antigen fusion protein encoding vectors exist in the art and are available from Invitrogen Corp., as the pVP22myc-His vector. The vector useful in this application ideally contains an f1, M13 or comparable phage origin, a coat protein fusion cassette (pIII or pVIII), the SV40 late region genes, and an SV40 origin.

Similarly, an adeno-associated virus/phage hybrid vector may be used to achieve the same amplified ligand production. An AAV-phage hybrid vector combines selected elements of both vector systems, providing a vector that is simple to produce in bacteria that is not constrained by a capsid packaging limit, while allowing infection of quiescent cells combined with integration into the host chromosome. Vectors containing many of the appropriate elements are readily available, and can be further modified by standard methodologies to include the necessary sequences. For example, the phagemid pAAV/Svneo, ATCC Accession No. 68065, contains AAV ITR sequences and an F1 origin of replication. In addition the vector pAV.CMV.LacZ provides many of the appropriate elements Fisher et al., *J. Virol.* 70(1):520–532, 1996.

Adeno-associated virus (AAV) is a defective member of the parvovirus family. The AAV genome is encapsulated as a single-stranded DNA molecule of plus or minus polarity (Berns and Rose, *J. Virol.* 5:693–699, 1970; Blacklow et al., *J. Exp. Med.* 115:755–763, 1967). Strands of both polarities are packaged, but in separate virus particles (Berns and Adler, *Virology* 9:394–396, 1972) and both strands are infectious (Samulski et al., *J. Virol.* 61:3096–3101, 1987). The single-stranded DNA genome of the human adeno-associated virus type 2 (AAV2) is 4681 base pairs in length and is flanked by inverted terminal repeated sequences of 145 base pairs each (Lusby et al., *J. Virol.* 41:518–526, 1982; Muzyczka, *Curr. Top. Microbiol. Immunol.* 158:97–129, 1992). In addition, the viral rep protein appears to mediate non-homologous recombination through the ITRs (Giraud et al., *J. Virol.* 69:6917–6924, 1995; Linden et al., *Proc. Natl. Acad. Sci. USA* 93:7966–7972, 1996). Accordingly, as parvoviral genomes have ITR sequences at each end which play a role in recombination and which are generally required for parvoviral replication and packaging, the vectors of the present invention generally contain all or a portion of at least one of the ITRs or a functional equivalent thereof.

Adeno-associated viruses may be readily obtained and their use as vectors for gene delivery has been described in, for example, Muzyczka, *Curr. Top. Microbiol. Immunol.* 158:97–129, 1992; U.S. Pat. No. 4,797,368, and PCT Application WO 91/18088. Construction of AAV vectors is described in a number of publications, including U.S. Pat. No. 5,173,414; Lebkowski et al., *Mol. Cell. Biol.* 8:3988–3996, 1988; Tratschin et al., *Mol. Cell. Biol.* 5(11):3251–3260; Hermonat and Muzyczka, *Proc. Nat'l. Acad. Sci. USA* 81:6466–6470, 1984; U.S. Pat. Nos. 5,871,982, 5,773,289, 5,843,742, and 5,474,935; and PCT Application Nos. WO 98/45462 and WO 98/48005, all of which are incorporated herein by reference.

AAV-2 can be propagated as a lytic virus or maintained as a provirus, integrated into host cell DNA (Cukor et al., in "The Parvoviruses," Berns ed., Plenum Publishing Corp., N.Y. pp. 33–66, 1984). Although under certain conditions AAV can replicate in the absence of helper virus (Yakobson et al., *J. Virol.* 61:972–981, 1987), efficient replication requires coinfection with either adenovirus (Atchinson et al., *Science* 194:754–756, 1965; Hoggan, *Fed. Proc. Am. Soc. Exp. Biol.* 24:248, 1965; Parks et al., *J. Virol.* 1:171–180, 1967); herpes simplex virus (Buller et al., *J. Virol.* 40:241–247, 1981) or cytomegalovirus, Epstein-Barr virus, or vaccinia virus. Hence the classification of AAV as a "defective" virus.

The AAV-phage hybrid vector for ligand identification generally comprises an F1, M13 or comparable origin, a coat protein fusion cassette (e.g., pIII-ligand, pVI-ligand, pVII-ligand, pVIII-ligand, pIX-ligand, or other phage coat-ligand combinations), a bacterial gene which facilitates selection, such as ampicillin resistance, and the two AAV ITRs (or functional equivalents thereof), between which is inserted the promoter driven reporter or selectable gene. The hybrid phage can then be used to transduce cells. The positive cells are identified and the ligand sequences are amplified by PCR using the ITRs or coat protein gene as the template sequence. This amplified ligand fusion construct can then be sub-cloned into other vectors for further rounds of transfection, selection, and ligand sequence identification.

In related embodiments, the present invention provides an AAV-phage vector that is designed to produce functional AAV viral particles upon co-infection with a "rescue" virus, such as an adenovirus. In this embodiment, the AAV-phage particle enters the cell as a "phage particle", but once inside, produces AAV particles that infect surrounding cells. This method can thus be used to amplify gene delivery effectiveness in a target organ or tissue. Briefly, in this approach, a ligand displaying phage particle containing a AAV-phage vector which contains a transgene of interest as well as ligand fused to the coat protein is used to transduce a cell. Concurrent with or subsequent to contacting the cells with the transgene containing AAV-phage particle, a ligand displaying helper AAV-phage is also used to supply the rep and cap genes for viral particle formation. Following transduction with the appropriate bacteriophage, the cell is infected with a "rescue" virus, such as an adenovirus, which allows viral particles to form and infect neighboring cells. Alternatively, the rep and cap functions can be supplied on the helper adenoviral genome.

In another aspect, mutant coat proteins or additional components or methods may be used to increase transduction efficiency. A particularly preferred manipulation is to mutagenize a coat protein so as to facilitate uncoating upon cellular internalization. For example, the filamentous phage coat protein VIII encoding gene can be mutagenized such that it is encodes a slightly unstable protein and thus allows more rapid uncoating and increased transduction capacity. Accordingly, one of ordinary skill in the art would readily recognize that given the teachings presented herein that mutations may be selected for using reporter gene expression.

In the various embodiments, when utilizing filamentous phage or another single-stranded DNA vector, transduction may be enhanced by facilitating the conversion of the single-stranded DNA to double-stranded DNA. The mechanism for conversion of single-stranded phage DNA to double-stranded DNA is analogous to that which occurs during infection with single-stranded DNA genome of a parvovirus such as an adenoassociated virus (AAV). In the case of recombinant AAV, conversion to dsDNA is a rate-limiting step for efficient transduction. The E4 orf6 gene product provided by helper Adenovirus or on a separate expression plasmid provides this function and increases transduction efficiency between 100–1000 fold. Accordingly, as variety of genotoxic treatments including gamma radiation, UV, heat shock, and DNA synthesis inhibitors and topoisomerase inhibitors (e.g., hydroxyurea, camptothecin, etoposide, and the like, see, e.g., Ferrari et al., *J. Virol.* 70:3227–3234, 1996; Alexander et al., *J. Virol.* 68:8282–8287, 1994; Russell et al., PNAS 92:5719–5723, 1995) will increase rAAV transduction efficiency in the absence of infection by helper virus, similar treatments can also increase the transduction efficiency of recombinant phage vectors and thus may be utilized in the practice of the present invention. Accordingly, any such treatment or agent that facilitates DNA repair and/or facilitates the conversion of single stranded DNA to double stranded DNA is considered a genotoxic agent or treatment as that term is utilized herein.

In other embodiments, peptides or other moieties that allow or promote the escape of the vectors (and any molecule attached thereto or enclosed therein) from the endosome and/or target the vectors to the nucleus are incorporated and expressed on or attached to the surface of the of the ligand displaying genetic package (e.g., bacteriophage). Such "other moieties" include molecules that are not themselves peptides but which have the ability to disrupt the endosomal membrane, thereby facilitating the escape of the vector, and molecules that otherwise mimic the endosomal escape properties of the within-described peptide sequences (see, e.g., published PCT Application No. WO 96/10038, the disclosure of which is incorporated by reference herein).

Peptide sequences that confer the ability to escape the endosome are particularly preferred. Such sequences are well known and can be readily fused or conjugated covalently or genetically to a coat protein, such as genes III, VI, VII, VIII, and IX or similar coat protein encoding genes of filamentous phage. Although fusion of one or more peptide sequences to a coat protein is described herein as a preferred embodiment, it should be understood that other methods of attachment—and other moieties besides peptides—are useful as well. Further, as those of skill in the art can readily appreciate, the present invention may be utilized to screen for peptide sequences that enhance transduction via endosomal escape or nuclear targeting when combined with ligand targeting agents. Accordingly, dual display peptides may be utilized for such screening, wherein one coat fusion or conjugate represents a known ligand and the other coat protein fusion or conjugate represents the sequence to be screened.

As with single display vectors, novel peptides or variants may be selected through rounds of cell contact and recovery of cells expressing the reporter gene, followed by identification of the encoded ligand.

In yet other embodiments, combinations of elements that facilitate transduction may be utilized. For example any combination of genotoxic treatment, endosomal escape peptides, and nuclear targeting may be used. In one example, UV and heat shock or heat shock and an endosomal escape peptide or nuclear targeting peptide may be utilized.

In yet another embodiment, cell attachment moieties (e.g., peptides) may be chemically conjugated, non-covalent, (e.g., electrostatic, antibody-antigen, biotin-streptavidin, etc.) or genetically fused to the exterior of the ligand display package. For example, many animal viruses encode sequences for both general cell binding and sequences specific for internalization. In this regard, adenovirus particles use both the knob protein (for receptor binding) and integrin binding for internalization. Highly charged proteins such as polylysine also facilitate binding to the negatively charged cell membrane, but may also result in undesirable non-specific transduction of any cell. Thus, when non-specific transduction is sought, highly charged peptides such as polylysine, histone, etc. may be used. However, in the practice of the present invention preferred peptides are those that will bind to cells at low affinity and facilitate internalization only in the presence of a second displayed ligand (e.g., EGF). Examples include L-selectin, the sequences encoding known heparin binding peptides (e.g., residues 65–81 from FGF2 which have been implicated in heparin binding (Imamura et al., *Biochem. Biophys. Acta* 1266:124–130, 1995)) and the heparin binding sequences identified in angio-associated migratory cell protein (Beckner et al., *Cancer Res.* 55:2140–2149, 1995) that fit a heparin binding consensus RRXRRX (SEQ ID NO: 18) (Cardin and Weintraub, *Arteriosclerosis* 9:21–32, 1995) and RGD containing sequences (Pierschbacher and Ruoslahti, *Nature* 309:30–33, 1984) that bind cell surface integrins.

As one of skill in the art can readily appreciate the selection methodologies described herein may be utilized to screen for additional cell attachment peptides. Briefly, cell attachment peptides may be conjugated or genetically fused to the exterior of a ligand display package. Typically, the cell attachment moiety will be attached to a display package such as a dual display phage such that an internalizing ligand and the cell attachment moiety will be jointly displayed. Accordingly, such joint display allows one of skill in the art to detect a change in transduction efficiency between packages displaying internalizing ligands alone and co-display in the presence of a cell attachment moiety (e.g., peptide).

In one example, to allow independent binding of the EGF-pIII fusion protein and the accessory cell attachment peptide, the cell attachment peptides are fused or conjugated to the phage major coat protein, pVIII (a small protein that makes up the tubular protein sheath that encapsulates the phage genome of which there are about 2700 copies per particle). Further, it has been established that pVIII can tolerate the addition of small peptides on its N-terminus (Ilyichev et al., *FEBS Lett* 301:322–324, 1992; Makowski *Gene* 128:5–11, 1993) which is used to produce the so-called "landscape phage" (Petrenko et al., *Protein Eng.* 9:797–801, 1999). Small peptides (~6–8aa) may be fused directly to the N-terminus or made as substitutions in the middle of pVIII as described by Petrenko (supra). For larger peptides or where more than one peptide is to be inserted into or conjugated to the coat, a wild type pVIII protein may be included in the phage system as described for the dual display phagemid. Once sequences are found that enhance transduction efficiency in a representative cell line such as COS1 or other cells, the sequences may be further optimized by mutation and further selection by the ligand identification methods described herein.

As noted above, dual display vectors are useful within the context of the present invention. In dual display embodiments additional elements displayed on a coat protein (e.g., pIII, pVI, pVII, pVIII and/or pIX and the like) such as an endosomal escape sequence, nuclear trafficking sequences or random peptide sequence may be incorporated into or conjugated to the phage particle to enhance phage mediated transduction or to test for enhanced transduction. These elements enhance transduction by facilitating cell binding, endosomal escape, nuclear localization, and other points along the transduction pathway that are currently rate limiting. Accordingly, it would be advantageous to display separate elements on pIII and pVIII (or analogous exterior proteins, e.g., pVI or others) such that for example, the targeting ligand is expressed on pIII and the endosomal escape sequence on pVIII. Such separation may also minimize the possibility of interference of the function of one element with the other. Thus, a phagemid vector can be constructed that allows fusion and display of distinct peptides or proteins on both pIII and pVIII. For example, in one embodiment, only one pIII gene (the fusion) may be present when phage rescue is performed with pIII deleted helper phage. However, 2 pVIII genes are present: one on the phagemid (the pVIII fusion) and one (wild-type) on the helper phage. Thus the vector is designed to display a peptide or protein ligand on pIII and additional accessory peptide(s) or protein(s) on pVIII as a mosaic with wild type pVIII. Further, as there may exist an upper limit to displaying peptides on pVIII because peptides larger than about 8 residues interfere with assembly of the phage particle (Ilyichev et al. (supra); Makowski, (supra)), displaying the accessory protein as a mosaic allows for proper particle assembly and the display of peptides larger than 6–8 residues on the major coat protein, pVIII.

Thus, an example of a dual display filamentous phage presents a ligand (e.g., FGF) as a fusion to gene III and an endosomal escape peptide fused to gene VIII. The locations of the ligand and escape sequences are interchangeable. Escape sequences that are suitable include, without limitation, the following exemplary sequences: a peptide of Pseudomonas exotoxin (Donnelly, J. J., et al., *PNAS* 90:3530–3534, 1993); influenza peptides such as the HA peptide and peptides derived therefrom, such as peptide FPI3; Sendai Virus fusogenic peptide; the fusogenic sequence from HIV gp1 protein; Paradaxin fusogenic peptide; and Melittin fusogenic peptide (see WO 96/41606).

Another sequence that may be included in a vector is a sequence that facilitates trafficking proteins into the nucleus. These so-called nuclear translocation or nuclear localization sequences (NLS) are generally rich in positively charged amino acids. Because the carboxyl terminus of gene VIII protein of filamentous phage already carries a positive charge, increased charge and likeliness of nuclear transport may be enhanced by fusing known mammalian cell NLS sequences to the gene VIII protein. NLS fusions to other coat proteins of filamentous phage may be substituted.

Examples of NLS sequences include those resembling the short basic NLS of the SV40 T antigen; the bipartite NLS of nucleoplasmin; the ribonucleoprotein sequence A1; the small nuclear ribonucleoprotein sequence U1A, and human T-lymphocyte virus-1 Tax protein. Other useful NLS sequences include the HIV matrix protein NLS; and the nuclear translocation components importin/hSRP1 and Ran/TC4; the consensus sequence KXX(K/R) (SEQ ID NO: 4) flanked by Pro or Ala; the nuclear translocation sequence of nucleoplasmin; or the NLS from antennapedia (see WO 96/41606).

Further, sequences which direct the genetic package to various cellular compartments may be useful within the context of the present invention. For example, while FGF appears to be trafficked to the nucleus via a nuclear localization-like peptide, EGF appears to be trafficked through the lysosome. Accordingly, in addition to the putative ligand, a lysosomal directing sequence may be incorporated into one of the coat proteins of the genetic package. Exemplary sequences in this regard are KCPL (SEQ ID NO: 11) which acts as a lysosomal targeting sequence (Blagoveshchenskaya et al., *J. Biol. Chem.* 273(43): 27896–27903, 1998), the ubiquitin-dependent endocytosis motif DSWVEFIELD (SEQ ID NO: 12)(Govers et al., *EMBO J.* 18(1):28–36, 1999, and DQRDLI (SEQ ID NO: 13) or EQLPML (SEQ ID NO: 14) from MCHII which also target the lysosome (Kang et al., *J. Biol. Chem.* 273(32) :20644–20652, 1998).

As described herein, the library is then propagated in the display phage by transfection of a suitable bacteria host (e.g., DH5αF' for filamentous phages), and growing the culture, with the addition of a replication-competent helper virus (for phagemid vectors) if necessary, overnight at 37° C. The phage particles are isolated from the culture medium using standard protocols.

Infection of mammalian cells with phage is performed under conditions that block entry of wild type phage into cells (Barry et al., *Nature Med.* 2:299–305, 1996). Phage are added directly to cells, typically at titers of $\leq 10^{12}$ CFU/ml in a buffer, such as PBS with 0.1% BSA or other suitable blocking agents, and allowed to incubate with the cells at 37° C. or on ice. The amount of phage added to cells will depend in part upon the complexity of the library. For example, a phage display library containing $10^5$ members has each member represented $10^6$ times in 1 ml of a typical phage titer of $10^{11}$ colony forming units/ml.

II. Detection/Selection of Transgene Expression

The genetic package display library is ultimately screened against the target tissue or cell line. Screening can be performed in vitro or in vivo. While combinatorial screening methods have been performed in the past, these methods are unable to determine the transduction capability of the displayed ligand (see, U.S. Pat. No. 5,733,731, incorporated herein by reference). The criteria for a positive "hit" in the present invention is that the phage must be able to bind, be internalized, and enable detection of the internalized ligand by detecting a selectable marker, such as, for example, by expressing the phage genomic DNA containing the reporter/selectable gene in the target or test cell or allowing direct nucleic acid detection (e.g., PCR or DNA binding). In this regard, while not wishing to be bound to a particular theory, it is believed that the phage should bind, internalize, uncoat, translocate to the nucleus, and replicate, in order to express the gene or otherwise facilitate detection (however, translocation and uncoating may occur in any order). Thus, in preferred embodiments only sequences that reach the nucleus are selected.

The test cells may be any cells that express a receptor of choice or may be a cell type or source for which gene therapy is destined. Thus, in some instances, the receptor may be unknown. In such cases, the selection method can be used to isolate a ligand for a receptor without a known ligand (orphan receptor) such as erbB3 or similar orphan receptor. Briefly, the orphan receptor is cloned into a mammalian expression vector that also contains a selectable drug resistance gene and transfected into mammalian cells, such as COS cells. Stable transfectants that overproduce the orphan receptor are selected by cultivation in the appropriate drug. This receptor-transformed COS cell line is then used as the cell line for selection of ligand-displaying phage.

In one aspect of the present invention, natural ligands or domains (i.e., the naturally occurring ligand for a cell surface protein that internalize). In this aspect display of protein domains is utilized instead of full length cDNAs by fragmenting the cDNAs to an average size that would encode proteins ranging from about 50 to 900 amino acids (~150 to 2700 base pairs). It is estimated that 80% of all active protein domains fall within this range. In addition to revealing active domains, fragmentation may allow more sequences to be displayed because the smaller active peptide domains would be separated from sequences that inhibit display. Fragmentation is accomplished by using random primers and PCR amplification during cDNA synthesis or by DNAse 1 digestion of full-length cDNA. See, e.g., Cochrane et al., *J. Mol. Biol.* 297(1):89–97, 2000 and Santini et al., *J. Mol. Biol.* 282(1):125–135, 1998 Accordingly, the present invention has application in identifying cell-targeting ligands from cDNAs derived from various cell types.

In one embodiment a library of cDNAs that is representative of the sequences encoding all the protein domains made by a cell type or tissue are utilized. Briefly, the library is constructed using random oligonucleotide primers that have extensions encoding restriction enzyme recognition sites such that the final cDNA products can be cut with the restriction enzymes and ligated into an appropriate phage vector (e.g., MG4, pUC-MG4). For example, the first strand cDNA synthesis is primed with a random 6-mer oligonucleotide containing a Pst1 restriction site extension. The second strand synthesis is performed using a random 6-mer oligonucleotide extended with a Nco1 restriction endonuclease. In this manner the cDNA fragments are cloned into the Nco1/Pst1 sites in a vector in the 5' to 3' direction. Thus only 3 possible reading frames out of 6 (if read off both coding and complementary strands) are inserted into the vector and one or more of these orfs encodes a protein that is present in the cell. The resulting cDNA fragments may be size selected to obtain a population of a preferred size ranging from 30 to 1000 nucleotides. The preferred library is normalized to remove highly redundant sequences and increase the probability of selecting protein domains encoded by rare mRNAs. For example, normalization could be performed using subtractive hybridization to remove repetitive sequences (high Cot), (see e.g., Bonaldo et al., *Genome Res.* 6:791–806, 1996). An alternative to random cDNA synthesis is to make a library of DNAse fragmented cDNAs (from a library or from individual cDNAs) or using methods described by Roninson for the generation of GSEs (Gudkov et al., *Proc. Natl. Acad. Sci. USA* 91:3744–3748, 1994) and others (Fehrsen and du Plessis, *Immunotechnology* 4:175–184, 1999; Petersen et al., *Mol. Gen. Genet.* 249:425–431, 1995; Kay (supra)).

Following vector construction and phage production the phage cDNA library is contacted with cells or tissues that display the receptor for which the cognate ligand is sought and the ligand selected using the selection strategies described herein. The cell line may express the natural receptor or be engineered to overexpress a recombinant receptor gene that is stabley expressed in that cell line using standard recombinant DNA methods. At 72 to 96 hours after phage addition the cells are harvested and the reporter gene (e.g. GFP) positive cells are collected. The sequences encoding the ligand are recovered by PCR or Hirt supernatant extraction analyzed or the phage reconstituted and used as input phage for the next round or selection. The library is monitored at each round of selection by restriction enzyme analysis of phage DNA to determine if the complexity of the library has been sufficiently reduced to allow identification of one or more active ligands. The ligand encoding sequences are compared to databases of known genes to determine if the recovered sequence is a portion of a known gene. Alternatively, the ligand encoding cDNAs are used as probes of conventional cDNA libraries to identify the full-length gene using standard molecular biology protocols for identification of full-length cDNA from partial sequences.

The feasibility of the aforementioned approach can be evidenced by using the cDNA encoding the proopiomelanocortin (POMC) gene (which encodes six different peptide ligands) is fragmented at random by DNA 1, ligated to the appropriate linker adaptors (see Chapter 9 by Du Plessis and Jordaan in Kay et al., 1998) and inserted into an appropriate phage or phagemid. The resulting library contains a mixture of DNA fragments, some of which will be inserted in-frame ($\frac{1}{3}$ if cloning is directional and $\frac{1}{6}$ if cloning is bi-directional) with the pIII coat protein of the phage vector. The phages that display fragments encoding one of the six peptide ligands or a functional fragment thereof will bind and internalize in cells that display the appropriate receptor. The library is selected against cell lines that naturally express one of the receptors or against cells that are engineered to overexpress the receptor. For example, the POMC fragmented gene library is selected against COS cells that are made to overexpress the melanocortin1 receptor. Accordingly, the cDNA fragments that are selected encode the MSH-α peptide contained within the POMC cDNA. A series of overlapping cDNAs selected in this manner will define the minimal sequence that is sufficient to functionally interact with the melanocortin1 receptor. Thus, the minimal functional peptide is defined in a manner analogous to the identification of minimal epitopes for antibody binding using methods described by Geyson et al. (*J. Immunol. Meth.* 102:259–274, 1987). Similarly, the library may be selected against COS cells that overexpress ACTH or β-endorphin receptor to identify cDNAs encoding their cognate receptors.

In further embodiments, due to post-translational modifications the selection of natural ligands for mammalian cells may be enhanced by utilizing ligands produced in mammalian cells and conjugating such ligands to ligand display package of interest. Briefly, the cDNAs are expressed in mammalian cells thereby allowing post-translational processing and modification that takes place in these cells. In this regard, the phages may be conjugated to the mammalian cell synthesized library by non-covalent (e.g., electrostatic, etc.) linkage (e.g., an antibody-antigen epitope interaction, streptavidin-biotin, etc.) or by covalent means. The total cDNA is subcloned into a mammalian expression vector such as pSecTag2 (available from Invitrogen, Calif.), that is designed to tag each cDNA gene product with a binding site for an antibody or other site specific protein-binding sequence (e.g., IgG binding domain). As many cDNA molecules may contain stop codons, an additional tag may be added downstream of the secretion signal, but upstream of the cDNA insert (e.g., HA etc.). The cells are transfected with an epitope tagged library and distributed into individual or pools of transfected cells. The conditioned media is removed from the cells, phage that display an epitope binding antibody fragment or other epitope binding moiety are added to the medium (at about $10^{11}$ pfu/ml), and the mixture is added to fresh target cells. The phages bind the ligands via the displayed antibody and the epitope tag on the ligand. Those ligands that are internalized by the target cells direct phage-mediated transduction of the target cells. Positive transduction is detected by GFP fluorescence, drug selection, or any reasonable detection means. The cells that secrete functional ligands are identified as those from which transduction competent conditioned medium was drawn and the positive cDNAs are recovered by PCR. In the case of pools of cDNAs the pools are deconvoluted to identify individual cDNAs.

In yet additional embodiments, tissue-specific or tumor-specific ligands can be selected by pre-absorption of the phage library against normal or non-targeted tissues of cell cultures. The selection process can also be applied in vivo by injecting the library into tumor-bearing mice. The tumor is removed from the mouse 48–72 h after injection. A cell suspension is prepared and phage genome bearing cells selected by one of the methods described herein. The gene whose product allows entry and expression of the phage genome is then isolated from the drug resistant cell colonies.

Screening may be performed directly against the target cells with no pre-screening or pre-enrichment. In one aspect, the present invention provides a method of identifying target cells or tissues for known or putative ligands. In this regard, phage display may be used to display a library of known or putative ligands (e.g., peptides, antibody fragments and the like) and screen singular tissues or cell types, or pools of tissues or cell types, thereby identifying target cells or tissues which are effectively transduced by a ligand. As used herein, "pool" refers to two or more cell types or tissue types. In one embodiment, known ligands are presented on a ligand displaying genetic package to a pool of a variety of cell or tissue types and transgene expression is monitored. In a further embodiment, putative ligands are used to screen a pool of a variety of cell or tissue types for transduction ability. In this regard ligands may be recovered and identified which efficiently transduce a particular tissue or cell type. Identification of cell specific ligands could greatly improve existing vectors for therapeutic gene delivery by targeting specific cells thus reducing toxicity and allowing vectors to be administered systemically.

Such cell type or tissue-type screening provides for selection that requires biological interaction rather than simple binding and does not require recovery of infective phage. In addition, cell surface receptors need not be identified and purified for the screening to be effective. A further aspect of the present invention is that it can be easily adapted to high throughput applications for screening a variety of cell types or tissues and/or for screening libraries of putative ligands against libraries of putative receptors/binding partners (i.e., anti-ligands) which lead to transgene expression (see infra). In this regard, screening of a variety of ligand/cell interactions could be performed, including, for example, pathogen/host interactions, ligand/receptor, etc.

In one aspect, the present invention may be utilized to identify a variety of protein-protein interactions. In particular, a set of unknown proteins/peptides may be selected based upon interaction with another set of known or unknown proteins/peptides (e.g., random peptides, cDNA libraries, or antibody gene libraries). In one embodiment, putative ligands are displayed on the surface of filamentous phage that carry a reporter gene. These display phage are contacted with a cell line displaying a putative anti-ligand (protein/peptide) on its surface as a receptor fusion protein, such that binding of successful detection of the reporter gene requires binding of the phage display ligand and the cell surface displayed anti-ligand, as well as internalization and transgene expression. Such screening can be utilized in a variety of methods, for example, a known ligand may be screened against a library of potential anti-ligands, a library of unknown ligands may be screened against a known protein/peptide anti-ligand, and two libraries of peptides/proteins may be screened against each other to identify ligand/anti-ligand interactions (protein-protein).

A ligand/anti-ligand pair refers to a complementary/anti-complementary set of molecules that demonstrate specific binding, generally of relatively high affinity. Exemplary ligand/anti-ligand pairs include an antibody and its ligand as well as ligand/receptor binding. While it should be understood that the designation of either component of the above mentioned ligand/anti-ligand pairs as either a ligand or anti-ligand is arbitrary, when necessary to specify a particular component, a "ligand", as used herein, is meant to describe peptides or proteins displayed on a genetic package carrying an expressible transgene. Further, when necessary to define anti-ligand with specificity, an "anti-ligand", as used herein, demonstrates high affinity and is expressed on the surface of the target cell to be monitored for transgene expression.

Any cell surface receptor may be used as the fusion construct for the cell surface displayed anti-ligand. However, in a preferred embodiment, the extracellular domain of the receptor is replaced with the putative anti-ligand. Construction of such fusions is routine in the art given that sequences as well as the extracellular intracellular domains of numerous receptors are known and available in the art. Komesli et al., *Eur. J. Biochem* 254(3):505–513, 1998; Naranda et al., *Proc. Natl. Acad. Sci. USA* 94(21):11692–11697, 1997; Rutledge et al., *J. Biol. Chem.* 266(31):21125–21130, 1991; Lemmon et al., *Embo J.* 16(2):281–294, 1997; Foehr et al., *Immunol. Cell Biol* 76(5):406–413, 1998. Exemplary fusion constructs include, for example, anti-ligand-FGF receptor or anti-ligand-EGF receptor constructs.

In a further embodiment, a large pool of cDNAs may be tested by transfecting into a large number of mammalian cells (e.g., COS cells). Ligand displaying phage are exposed to the transfected cells and positive cells identified by either drug selection or detection of an expressed transgene (e.g., GFP sorted by FACs). PCR may be performed on single cells to identify ligand/anti-ligand binding pairs. In this regard PCR primers directed to the known portion of the fusion construct may be used. For example, for phage display using pIII to display the ligand, the PCR primer will be directed to the pIII gene, while in order to identify the anti-ligand, the PCR primer will be directed to the surface membrane protein (e.g., a receptor domain) encoding portion of the fusion construct. Alternatively, the plasmids within positive cells may be rescued by Hirt supernatant method and separated from phage DNA by gel electrophoresis or chromatography. (Kay et al., supra). The selected cDNA plasmids may then be used to retransform bacteria. New plasmid DNA is prepared and used for additional rounds of screening by transfection into the cells and phage contact.

In an alternative embodiment, detection may be by any means which allows for the detection of the internalized nucleic acid molecules, and may include Hirt extraction of small DNA, direct polymerase chain reaction (PCR) amplification of ligand DNA from reporter gene expressing cells and non-endogenous protein-nucleic acid molecule binding interactions (e.g., lac operon and lac repressor in a mammalian cell) in positive cells. In addition, it is possible to use direct PCR amplification of ligand DNA from cells wherein no reporter gene is used.

In the various embodiments of the present invention utilizing PCR amplification of ligand sequences, the methodologies allow for the rapid amplification of only internalized sequences. Typical phage display technologies require that the phage of interest (e.g., that which binds to a particular target) be eluted and amplified following transduction of the appropriate host bacterial strain. However, transduction of bacteria requires that bacteriophage are intact and maintain infectivity. To eliminate the requirement for infective phage, methodologies provided herein allow those of ordinary skill in the art to recover, by PCR, phage DNA sequences that have been trafficked to the nucleus, digest these sequences with appropriate restriction enzymes, remove extraneous sequences, subclone the desired sequences back into the phage display vector, and transform bacteria with this vector. Accordingly, by not requiring that the recovered phage be infective, the ability to display larger ligands as fusion constructs with coat proteins is possible. Further, recovery of uncoated phage, such as those targeted to the lysosomal or endosomal compartments, as well as those capable of directing expression in the nucleus is possible.

Briefly, in one aspect, the recovery by PCR and amplification proceeds as follows: An initial selection of cells is performed using the detection of a reporter gene, selective conditions, or the like and the total DNA is recovered from these cells. The recovered DNA is used as a template for PCR primers that are designed to flank the sequence of interest (the ligand encoding sequence, i.e., by using the pIII or pVIII sequences flanking the ligand insert as primer templates). The primers can be manufactured such that they can be easily removed from the ligand insert following restriction enzyme digestion, for example, the primers may contain a biotin moiety at the 5'-end. In the alternative, the primers may be removed by any known methods, including, for example, gel extraction, selective precipitation, and the like. In other alternatives primers need not be removed, however their removal facilitates ligation efficiency of ligand insert to vector. Further, the primers can provide restriction sites for subcloning etc.

Following amplification, the PCR product is purified to remove the polymerase and digested with restriction enzyme to excise the putative ligand insert. Enzymes are chosen in order to facilitate directional subcloning into either the original vector or a new construct, if so desired. Following enzyme digestion, the extraneous sequences are removed (e.g., by using biotinylated primers and streptavidin conjugated to beads or other solid support). The resulting DNA sequences are then ligated into the desired vector and the resulting vector is transformed into bacteria using standard methodologies. The transformed bacteria are then used to generate new phage particles or new DNA for additional rounds of screening. However, while it should be understood that the use of a reporter gene may lead to enhanced DNA recovery and fewer rounds of screening, there is not always a requirement that a reporter gene be used.

In an alternative embodiment, recovery of replicated internalized nucleic acid molecules may be achieved via a nucleic acid binding domain. Accordingly, when using phage, the phage genome can be altered such that a DNA binding sequence is incorporated therein. In one example, the phage vector may contain one or more copies of the lac operon, thereby allowing any internalized and replicated phage vectors to be purified from a cell lysate by a solid surface having conjugated thereto the lac repressor protein. Briefly, target cells are contacted with ligand displaying genetic packages (e.g., phage) for 48 to 72 hours. Since only the packages displaying an appropriate ligand are internalized and reach the cell nucleus where vector replication takes place, these will be the sequences that will be selected for and thus, no reporter gene is required (e.g., GFP). Accordingly, the replicated vector is double stranded and the double stranded form of the lac operon will bind the lac repressor. The cells are then lysed and nuclear extracts are prepared, which are then passed over a solid support (e.g., Sepharose 4B) having conjugated thereto the lac repressor protein. The column is washed, then eluted by a salt or pH gradient, thereby releasing the bound DNA which can now be utilized in PCR reactions to amplify the ligand sequences for sub-cloning into another vector for further rounds of infection or characterization or the DNA can be used directly (without PCR) to transform bacteria and thereby produce more phage for further screening.

In other embodiments, the ligand displaying genetic package may also contain the nucleic acid sequences that encode the nucleic acid binding protein. For example, in the illustration above, the vector could also encode the lac repressor and the solid support has an anti-lac repressor antibody conjugated thereto, thereby allowing for recovery of nucleic acid molecules bound by the lac repressor.

One of ordinary skill in the art would readily recognize that a variety of nucleic acid binding proteins could be utilized as described above. In this regard, many proteins have been identified that bind specific sequences of DNA. These proteins are responsible for genome replication, transcription and repair of damaged DNA. The transcription factors regulate gene expression and are a diverse group of proteins. These factors are especially well suited for purposes of the subject invention because of their sequence-specific recognition. Host transcription factors have been grouped into seven well-established classes based upon the structural motif used for recognition. The major families include helix-turn-helix (HTH) proteins, homeodomains, zinc finger proteins, steroid receptors, leucine zipper proteins, the helix-loop-helix (HLH) proteins, and β-sheets. Other classes or subclasses may eventually be delineated as more factors are discovered and defined. Proteins from those classes or proteins that do not fit within one of these classes but bind nucleic acid in a sequence-specific manner, such as SV40 T antigen and p53 may also be used.

These families of transcription factors are generally well-known (see GenBank; Pabo and Sauer, Ann. *Rev. Biochem.* 61:1053–1095, 1992; and references below). Many of these factors are cloned and the precise DNA-binding region delineated in certain instances. When the sequence of the DNA-binding domain is known, a gene encoding it may be synthesized if the region is short. Alternatively, the genes may be cloned from the host genomic libraries or from cDNA libraries using oligonucleotides as probes or from genomic DNA or cDNA by polymerase chain reaction methods. Such methods may be found in Sambrook et al., supra.

Helix-turn-helix proteins include the well studied λ Cro protein, λcI, and *E. coli* CAP proteins (see Steitz et al., *Proc. Natl. Acad. Sci. USA* 79:3097–3100, 1982; Ohlendorf et al., *J. Mol. Biol.* 169:757–769, 1983). In addition, the lac repressor (Kaptein et al., *J. Mol. Biol.* 182:179–182, 1985)

and Trp repressor (Scheritz et al., *Nature* 317:782–786, 1985) belong to this family. Members of the homeodomain family include the Drosophila protein Antennapaedia (Qian et al., *Cell.* 59:573–580, 1989) and yeast MATα2 (Wolberger et al., *Cell.* 67:517–528, 1991). Zinc finger proteins include TFIIIA (Miller et al., *EMBO J.* 4:1609–1614, 1985), Sp-1, zif 268, and many others (see generally Krizek et al., *J. Am. Chem. Soc.* 113:4518–4523, 1991). Steroid receptor proteins include receptors for steroid hormones, retinoids, vitamin D, thyroid hormones, as well as other compounds. Specific examples include retinoic acid, knirps, progesterone, androgen, glucocosteroid and estrogen receptor proteins. The leucine zipper family was defined by a heptad repeat of leucines over a region of 30 to 40 residues. Specific members of this family include C/EBP, c-fos, c-jun, GCN4, sis-A, and CREB (see generally O'Shea et al., *Science* 254:539–544, 1991). The helix-loop-helix (HLH) family of proteins appears to have some similarities to the leucine zipper family. Well-known members of this family include myoD (Weintraub et al., *Science* 251:761–766, 1991); c-myc; and AP-2 (Williams and Tijan, *Science* 251:1067–1071, 1991). The β-sheet family uses an antiparallel β-sheet for DNA binding, rather than the more common α-helix. The family contains the MetJ (Phillips, *Curr. Opin. Struc. Biol.* 1:89–98, 1991), Arc (Breg et al., *Nature* 346:586–589, 1990) and Mnt repressors. In addition, other motifs are used for DNA binding, such as the cysteine-rich motif in yeast GAL4 repressor, and the GATA factor. Viruses also contain gene products that bind specific sequences. One of the most-studied such viral genes is the rev gene from HIV. The rev gene product binds a sequence called RRE (rev responsive element) found in the env gene. Other proteins or peptides that bind DNA may be discovered on the basis of sequence similarity to the known classes or functionally by selection. Furthermore, those of ordinary skill in the art will appreciate that the nucleic acid binding domain will chosen for a particular recovery method will preferably be one which is not already present within the target cells.

In a further embodiment, known or putative ligand-display phage may be used to screen a panel of cells that each express a potential target receptor. The source of the target receptor may be a known (i.e. cloned) receptor cDNA, or a collection of putative receptor cDNAs. For example, the putative receptor cDNAs may be identified from an epitope-tagged cDNA library as cDNAs that encode proteins that appear on the surface of cells. (see, Sloan et al., *Protein Expression and Purification* 11:119–124, 1997). Such cDNAs are inserted into an appropriate mammalian expression vector and transfected into a host cell. Preferably the host cell is eukaryotic, and more preferably the host cell is mammalian. The expression of the cDNA may be either stable or transient. Following expression the cells are contacted with the ligand-display phage and monitored for transgene expression (e.g., drug resistance, GFP, or other detectable product). One skilled in the art would recognize that identification of cell or tissue types as described above, in addition to using ligand display phage, could also performed by utilizing other ligand displaying means, such as RNA-peptide fusions as described by Roberts and Szostak (*Proc. Nat. Acad. Sci. USA* 94:12297–12302, 1997), other phage types, viruses, or on bacteria.

Pre-screening or pre-enrichment may be used and can be especially helpful when either too few or too many hits are observed. Enrichment for cell binding may improve detectability if no hits are found in the initial screen. A prescreen to remove phage that bind non-specific cells surface proteins may reduce non-specific hits if there are too many initial hits. For example, infection of $10^7$ target cells is performed with about $10^{11}$ phage, however a variety of cell density and phage titer ranges are useful. The cells are incubated for at least 2 hours and preferably 24–48 hours in PBS/BSA and washed extensively (Barry et al., *Nature Med.* 2:299–305, 1996). The cells are incubated in media at 37° C. for 24–96 hours and then detected or selected on the basis of expression of the reporter gene.

Assays for each of these reporter gene products are well known. For example, GFP is detected by fluorescence microscopy or flow cytometry, SEAP is detected in medium using a fluorescent substrate (Clontech; Palo Alto, Calif.), human growth hormone may be detected in medium by a simple and sensitive radioimmune assay (Nichols Institute; CA). Western blotting and ELISA may also be used to immunologically detect and measure the presence of reporter gene product. Alternatively, the message for the reporter gene is detected using RNase probe protection or fluorescent probe hybridization. For isolation of the phage vector DNA and insert, any technique that can identify and isolate the cells expressing detectable marker product may be used. Flow cytometry, in particular, is well suited for detecting fluorescence in or on a cell and isolating that cell. Further, flow cytometry is well suited for high throughput methodologies when necessary to isolate individual cells or groups of cells that express a reporter gene.

When the reporter gene is a selectable marker, the cells are grown in selective conditions. Depending upon the marker, the conditions may be a particular growth temperature, addition of a drug, or the like. In the examples provided herein, the selectable marker is neomycin transferase, which confers G418 resistance on mammalian cells. Briefly, the cells are grown in the presence of G418 for 7–14 days or until resistant colonies are visible microscopically. Colonies are picked, and phage vector DNA recovered, conveniently as amplification of the insert or Hirt supernatent.

Alternatively, multiple rounds of infection and selection are performed to reduce the complexity of the infecting phages. For example, drug-resistant colonies are pooled and the selected inserts amplified and cloned back into the phage display vector for a new round of infection. When the reporter is fluorescent, flow cytometry can be used to select the strongest fluorescing cells to select the most highly efficient gene delivery ligands. More stringent screening conditions also include higher selective drug concentrations. At the completion of a selection process, representative phage clones may be subjected to DNA sequence analysis to further characterize gene delivery ligands.

In a further aspect, high throughput screening methodologies, such as screening libraries by sub-selection of pools, may be utilized to identify ligands. Briefly, phage stocks containing a variety of members, as individual plaques, may be used in combination with an array to identify potential internalizing ligands. For example, a stock of bacteriophages containing library members may be divided into subset pool stocks such that each stock contains about $10^2$ to about $10^3$ members. Each stock solution is then screened utilizing an array (e.g., multi-well plates containing target cells). Upon detection of a reporter gene the phage stock may be sub-divided again and screened repeatedly until the phage which contains the internalizing ligand is identified. Alternatively, those of skill in the art will appreciate that the array may contain a variety of cell types which are capable of being screened with one or more phage libraries, of which may also include a variety of reporter genes (if so desired). For example, a variety of alternatively colored fluorescent protein expression vectors are available which can be used as reporter genes to provide multiplexing capability (Clontech, Palo Alto, Calif.). Accordingly, rapid identification of those cells which internalize the bacteriophage and/or libraries that contain internalizing ligands for a specific cell type, may be identified. Utilizing both a variety of bacteriophage libraries as well as a variety of cell types, would allow for a high throughput method of determining subsets of libraries that contain ligands for specific cell types, simultaneously. Array's for binding biomolecules are known in the art and therefore could be adapted to utilize the phage screening methodology of the present invention, see, e.g., PCT Application No. WO 95/11755, PCT Application No. WO 95/35505, U.S. Pat. No. 4,591,570. In addition, affinity based biosensors such as a Biacore instrument, available commercially from Biacore AB, Uppsula, Sweden, may be used to immobilize phage or cells for high throughput screening.

Moreover, while commonly used high throughput methodologies which utilize live cells are typically performed on arrays of 6 to 96 well plates, the current invention may also be carried out using cellular micro-arrays such as those described by U.S. Pat. No. 5,776,748. Briefly, such arrays may be manufactured such that designated areas of the array bind a defined number of cells or size of tissue. For example, the arrays can be constructed such that they bind only a single cell. Therefore, an array of single cells may be constructed with a variety of cell or tissue types. Because the size of the cell binding islands on the array may be chosen such that no more than one cell may bind on any given island, because the locations and geometric pattern of the islands may be predetermined, and because the cells will remain at fixed locations during assaying, cellular micro-arrays can provide for a high efficiency and high throughput method of assaying for internalizing ligands, anti-ligands, or target cells or tissues.

In a preferred embodiment flow cytometry is utilized, the cells are identified and counted by an automated detector unit. Because the locations and geometric patterns of the islands are predetermined, the detector can be designed or programmed to take measurements specifically at those locations. Therefore, identification of individual cells which have been successfully transduced by a ligand displaying genetic package carrying a nucleic acid molecule which encodes a detectable product is easily accomplished. In some embodiments, cells transduced by a ligand displaying genetic package carrying a nucleic acid molecule which encodes a selectable marker may be first selected on the basis of the appropriate sensitivity or resistance and then plated as individual cells and further selected or characterized by the methods described herein. In particular, selection may be employed prior to plating on the plates to isolate transformed or transfected cells and then the cells may be assayed in situ.

In addition, when using fluorescence assays, a detector unit may be placed above the plate or, if the plate is translucent, below the plate. In the case of transmission spectrophotometric assays, a translucent plate is used, a source of electromagnetic radiation is placed on one side of the plate and a detector unit on the other. Because of the small distances between individual isolated cells permitted by the present invention, detectors employing fiber optics are particularly preferred. Such sources of electromagnetic radiation and such detectors for electromagnetic transmission, reflection or emission are known in the applicable art and are readily adaptable for use with the invention disclosed herein.

The constructs and methods disclosed herein are also applicable to screening in vivo. Such screening may be performed similar to methods for targeting organs or xenograft tumors using phage displayed peptides (Pasqualini et al., Nature Biotech. 15: 542–546, 1997; Pasqualini et al., Nature 380: 364–366, 1996; and U.S. Pat. Nos. 5,622,699; 6,232,287; and 6,068,829 all of which are incorporated by reference herein in their entirety), except that the tissues, organs, or tumors are examined for reporter gene expression instead of the presence of phage. Briefly, a phage display library is injected intravenously into animals, generally mice, but preferably humans, and organs or tumor samples are tested for reporter gene function at 48–96 hours after injection. Tumor cells may be cultured in selective conditions or sorted by flow cytometry or other method to enrich for cells that express the phage transducing gene. The ligand encoding sequences can be amplified from selected cells as described above. As in in vitro screening, repeated rounds of infection and re-screening, alone or in combination with increased screening stringency, may be used to obtain the most efficient gene delivery ligands.

Specificity may also be examined in vitro using a panel of non-targeted and targeted cell lines and detecting expression of the phage transducing gene. Competition studies with free ligand or a neutralizing antibody to the ligand or receptor are used to confirm specific entry of phage via the ligand receptor complex. Alternatively, the cloned receptor for the ligand can be overexpressed in a cell line that normally does not express that receptor. Phage internalization and expression into the stable transfectants expressing the receptor but not the parent cell line indicates the specificity of the ligand for its receptor on receptor bearing cells.

Ligands that are identified as gene targeting ligands using the selection strategies described herein may be further tested for specificity by reporter gene expression in target and non-target cells and tissues. The ligand may also be tested in a variety of gene delivery methods, such as ligand-polylysine/DNA complexes (Sosnowski et al., J. Biol. Chem. 272:33647–33653, 1996) or retargeted adenovirus gene delivery (Goldman et al., Cancer Research 57:1447–1451, 1997).

The specificity of the targeting ligand may alternatively be determined in vivo by biodistribution analysis using one of the reporter genes described herein, such as luciferase. At various time points, mice injected with the ligand displaying phage are sacrificed and tissues examined for the presence of phage in non-targeted tissues by immunohistochemistry, an enzymatic assay that detects reporter product activity, or the like.

III. Uses

The methods described herein are designed to select cDNAs, Fabs, sFv, random peptides, and the like for discovery of new ligands or anti-ligands. They can also be used to select mutated and gene-shuffled versions of known ligands for targeting ability. Accordingly, as discussed above, the methodologies described herein allow for the directed evolution of genetic packages and/or ligands to develop ligands or whole vectors that delivery their associated components to the interior of the cell and facilitate expression of associated nucleic acid molecules. Thus the methods can be used to identify ligands useful for delivery of any molecule to the interior of a cell and can be further screened to target specific intracellular compartments, such as the nucleus, mitochondria, chloroplast, etc. The methods also can be used to direct the unbiased evolution of genetic packages into a vector for gene delivery and confer mammalian-cell specific tropism.

Although it is possible to modify vectors both chemically and genetically for more efficient gene transfer, the choice of each enhancing element must be determined by trial and error. However with genetic display packages such as phage, it becomes possible to apply the power of phage display and genetic selection to the evolution of more efficient vectors and thus bypass the more tedious and time-consuming process of rational design. Indeed along these lines, it is demonstrated herein that it is possible to selectively enrich for specific phage by their ability to introduce a reporter gene into the target cells. Thus, novel sequences, unanticipated by rational design, can be selected from libraries of highly diverse peptides or cDNAs using the methods described herein.

This directed evolution can also be used to create phage that are more suitable for in-vivo gene delivery having for example: increased serum half-life, selective tissue targeting, and decreased immunogenicity. A recent example of this is the selection of long-lived phage by repeated rounds of injection of phage libraries into animals and selection of surviving phage using either lambda or T7 phage. See, e.g, Merril et al., *Proc. Natl. Acad. Sci USA* 93(8):3188–3192, 1996 and Sokoloff et al., *Mol. Ther* 2(2): 131–139, 2000. Sokoloff et al. have identified sequences that increase the half-life of T7 phage by protecting phage against complement activation. Perhaps even more importantly, these peptides could be used as "stealthing" agents to protect other gene or drug delivery vectors from clearance. The work of Pasqualini and coworkers also demonstrates the ability to evolve phage in-vivo for the ability to home to specific tissues or to tumors. Recently, Samoylova et al. applied in-vivo panning to identify phage that targeted muscle indicating that phage can be developed that penetrate the vasculature to target tissues in-vivo. *Muscle Nerve* 22(4):46–466, 1999. Accordingly, these cited studies demonstrate the disclosed methodologies utilizing the present invention allows not only evolving of a targeting agent, but more importantly an agent that targets, internalizes, and facilitates the expression of an associated nucleic acid molecule. Thus, allowing for the evolution of a highly effective vector for in vivo gene delivery rather than creation through rational design.

These ligands may have increased transduction efficiency (as measured by an increase in the percentage of infected cells that express the reporter gene); increased expression of the reporter gene (as measured by intensity of reporter gene expression) in the phage transduced cells; increased specificity of transduction for target cells (as measured for ligand specificity); increased stability of the ligand (as measured by ability to target the ligand in vivo to tumor cells); increased affinity for receptor (e.g., removing dimerization requirements for ligands that dimerize); increased functionality (e.g., stimulates internalization); elimination of the need for cofactors (e.g., development of an FGF variant that binds with high affinity to the FGF receptor but not to heparin); altered specificity for receptor subtypes (e.g., an FGF variant that reacts with only one of the four FGF receptors).

The ligands identified by the methods described herein may be used as targeting agents for delivering therapeutic agents to cells or tissues. For example, a therapeutic gene can be incorporated into the phage genome and delivered to cells via phage bearing the gene delivery ligand on its protein coat.

A transducing gene, as used herein, refers to a gene which encodes a detectable product in the target cell. Preferentially, the transducing gene is a therapeutic gene. A "therapeutic nucleic acid" or "therapeutic gene" describes any nucleic acid molecule used in the context of the invention that effects a treatment, generally by modifying gene transcription, translation, or which supplies a replacement or amplification of an existing gene. It includes, but is not limited to, the following types of nucleic acids: nucleic acids encoding a protein, ribozyme, antisense nucleic acid, DNA intended to form triplex molecules, protein binding nucleic acids, and small nucleotide molecules. As such, the product of the therapeutic gene may be DNA or RNA. These gene sequences may be naturally-derived sequences or recombinantly derived. A therapeutic nucleic acid may be used to effect genetic therapy by serving as a replacement for a defective gene, by encoding a therapeutic product, such as TNF, or by encoding a cytotoxic molecule, especially an enzyme, such as saporin. The therapeutic nucleic acid may encode all or a portion of a gene, and may function by recombining with DNA already present in a cell, thereby replacing a defective portion of a gene. It may also encode a portion of a protein and exert its effect by virtue of co-suppression of a gene product.

As discussed above, the therapeutic gene is provided in operative linkage with a selected promoter, and optionally in operative linkage with other elements that participate in transcription, translation, localization, stability and the like.

The therapeutic nucleotide composition of the present invention is from about 20 base pairs to about 100,000 base pairs in length. Preferably the nucleic acid molecule is from about 50 base pairs to about 50,000 base pairs in length. More preferably the nucleic acid molecule is from about 50 base pairs to about 10,000 base pairs in length. Even more preferably, it is a nucleic acid molecule from about 50 pairs to about 4,000 base pairs in length.

The ligands/anti-ligands provided herein are useful in the treatment and prevention of various diseases, syndromes, and hyperproliferative disorders, such as restenosis, other smooth muscle cell diseases, tumors, such as melanomas, ovarian cancers, neuroblastomas, pterygii, secondary lens clouding, and the like. As used herein, "treatment" means any manner in which the symptoms of a condition, disorder or disease are ameliorated or otherwise beneficially altered. Treatment also encompasses any pharmaceutical use of the compositions herein. As used herein, "amelioration" of the symptoms of a particular disorder refers to any lessening, whether permanent or temporary, lasting or transient, that can be attributed to or associated with administration of the composition.

In certain embodiments, the compositions of the present invention may be used to treat angiogenesis-dependent diseases. In these diseases, vascular growth is excessive or allows unwanted growth of other tissues by providing blood supply. These diseases include angiofibroma, arteriovenous malformations, arthritis, atherosclerotic plaques, corneal graft neovascularization, delayed wound healing, diabetic retinopathy, granulations due to burns, hemangiomas, hemophilic joints, hypertrophic scars, neovascular glaucoma, nonunion fractures, Osler-weber syndrome, psoriasis, pyogenic granuloma, retrolental fibroplasia, scleroderma, solid tumors, trachoma, and vascular adhesions.

By inhibiting vessel formation (angiogenesis), unwanted growth may be slowed or halted, thus ameliorating the disease. In a normal vessel, a single layer of endothelial cells lines the lumen, and growth of the vessel requires proliferation of endothelial cells and smooth muscle cells.

As well, the ligands, anti-ligands, and cells identified by the present invention may be used to treat tumors. In these diseases, cell growth is excessive or uncontrolled. Tumors suitable for treatment within the context of this invention include, but are not limited to, breast tumors, gliomas, melanomas, prostate cancer, hepatomas, sarcomas, lymphomas, leukemias, ovarian tumors, thymomas, nephromas, pancreatic cancer, colon cancer, head and neck cancer, stomach cancer, lung cancer, mesotheliomas, myeloma, neuroblastoma, retinoblastoma, cervical cancer, uterine cancer, and squamous cell carcinoma of skin. For such treatments, ligands are chosen to bind to cell surface receptors that are generally preferentially expressed in tumors.

Through delivery of the compositions of the present invention, unwanted growth of cells may be slowed or halted, thus ameliorating the disease. The methods utilized herein specifically target and kill or halt proliferation of tumor cells having receptors for the ligand on their surfaces.

The identified ligands/anti-ligands may also be used to treat or prevent atherosclerosis and stenosis, a process and the resulting condition that occurs following angioplasty in which the arteries become reclogged. Generally, treatment of atherosclerosis involves widening a stenotic vascular lumen, permitting greater blood flow and oxygenation to the distal tissue. Unfortunately, these procedures induce a normal wound healing response in the vasculature that results in restenosis. Of the three components to the normal vascular response to injury, thrombosis, elastic recoil and smooth muscle cell proliferation, anti-thrombotics/platelet inhibitors and vascular stents effectively address acute/subacute thrombosis and elastic recoil, respectively. However, no existing therapy can modify the vascular remodeling that is due to proliferation of smooth muscle cells at the lesion, their deposition of extracellular matrix and the subsequent formation of a neointima. Accordingly, phage could be used to deliver therapeutic nucleic acids or proteins that would inhibit restenosis.

Wound response also occurs after other interventions, such as balloon angioplasty of coronary and peripheral vessels, with or without stenting; carotid endarterectomies; vein grafts; and synthetic grafts in peripheral arteries and arteriovenous shunts. Although the time course of the wound response is not well defined, if the response can be suppressed for a short term (approximately 2 weeks), a long term benefit is achieved.

In other various embodiments the applications of the technology described herein is virtually limitless. For example, bacteriophage may be retargeted (e.g., redirected from their native binding) using ligands added to their coat to treat bacterial disease in plants and animals. Briefly, ligands may be screened against a variety of pathogenic bacteria and ligands which effectively deliver expressible products to the interior of the cell may be utilized to shuttle toxic components selectively into these bacteria. One of ordinary skill in the art would readily recognize that the methods described herein may be modified to alter the native binding of a bacteriophage such that the bacteriophage binds and injects its contents or is internalized thereby delivering its contents in select bacteria. Accordingly, once ligands are identified the bacteriophage may be used to delivery cytotoxic expression plasmids to the interior of the bacteria or alternatively the ligands may be attached to toxic chemical moieties that will be delivered to the bacteria in high concentrations via the ligand targeting agent. Further, the mere delivery of a replication competent phage to a bacteria could induce death by cell lysis, thereby creating a bacteriophage antibiotic, specifically targeted to select bacteria. Such targeting may also be extended to targeting plant cells, yeast, fungi, and virtually any other cell or microorganism. For example, food production may be enhanced by transducing yeast or cheese producing bacteria with bacteriophage carrying a gene of interest and targeted to the yeast or bacteria using a ligand identified by the methods described herein.

The present invention provides the capability of identifying ligands which internalize as well as proteins, antibodies, cell/cell interacting proteins that define the interrelationships between cells, host/pathogen, tumor/stroma, autocrine/paracrine factors and allows identification of molecules that are targets for new drug discovery or are themselves therapeutically or diagnostically useful. Further, other peptides can be discovered by the methodologies taught herein that enhance endosomal escape, nuclear localization, cell binding, and thus discover ligands that are useful not only in phage mediated gene therapy, but generally applicable to standard gene therapy methodologies (e.g., enhancing gene expression from animal viral vectors, DNA-conjugates etc.)

The following examples are offered by way of illustration, and not by way of limitation.

EXAMPLES

Example 1

Modified Phage Vectors for Mammalian Cell Transduction

A mammalian expression cassette is inserted into a phage or phagemid vector and is used to detect ligand mediated phage entry via reporter gene expression in mammalian cells. A type 3 filamentous phage vector is modified for transduction of mammalian cells by insertion of a GFP expression cassette consisting of a CMV mammalian transcriptional promoter, the green fluorescent protein gene from pEGFP-N1 (Clontech; Palo Alto, Calif.), and a bovine growth hormone transcriptional terminator and polyadenylation signal to make the vector, MEGFP3 (see FIG. 1A). The mammalian expression cassette also contains an SV40 origin of replication adjacent to the CMV promoter. Similar constructs for monitoring entry and subsequent expression of phage genomes in mammalian cells are constructed from other known phage or phagemid vectors including pCANTAB 5 E (Pharmacia Biotech; Piscataway, N.J.) or M13 type 3 or 33 for gene III fusions (see Kay et al., *Phage Display of Peptides and Proteins: A Laboratory Manual*, Academic Press, 1996; McConnell et al., *Mol. Divers.* 1:165–176, 1996) and M13 type 8 or 88 vector for fusions to gene VIII protein (Roberts et al., *Methods Enzymol.* 267:68–82, 1996; Markland et al., *Gene* 109:13–19, 1991).

Example 2

Construction of FGF2-Containing Phage Display Vectors

Figure 1B:
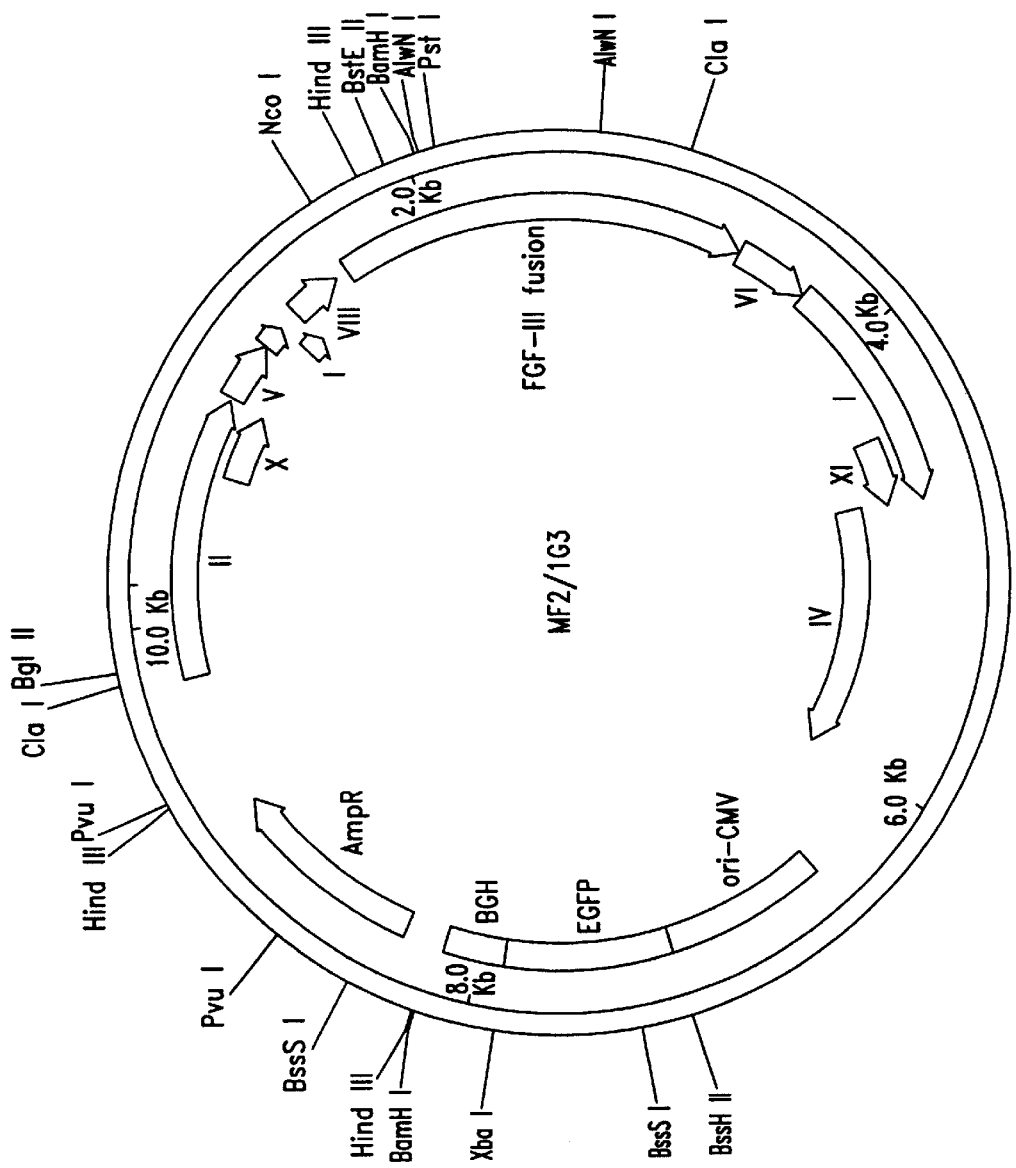

In the following examples, a phage that displays FGF2 on its surface is used to bind to the FGF2 receptor on mammalian cells and be internalized. An FGF2 gene is subcloned into the modified M13 phage type 3 vector, MEGFP3, to create the ligand display phage, MF2/1G3 (see FIG. 1B). The gene may also be mutated such that it encodes an FGF2 (C96S) (C78S) double mutant which enhances expression efficiency. The MEGFP3 vector has been modified with a mammalian expression cassette designed to express the reporter gene GFP to monitor mammalian cell transduction by the phage. Other vectors include pCANTAB 5 E (Pharmacia Biotech; Piscataway, N.J.) or M13 type 3 or 33 for gene III fusions (see Kay et al., *Phage Display of*

Peptides and Proteins: A Laboratory Manual, Academic Press, 1996; McConnell et al., Mol. Divers. 1:165–176, 1996). Similarly, FGF2 is cloned into M13 type 8 or 88 vector for fusion to gene VIII protein (Roberts et al., Methods Enzymol. 267:68–82, 1996; Markland et al., Gene 109:13–19, 1991).

Figure 2:
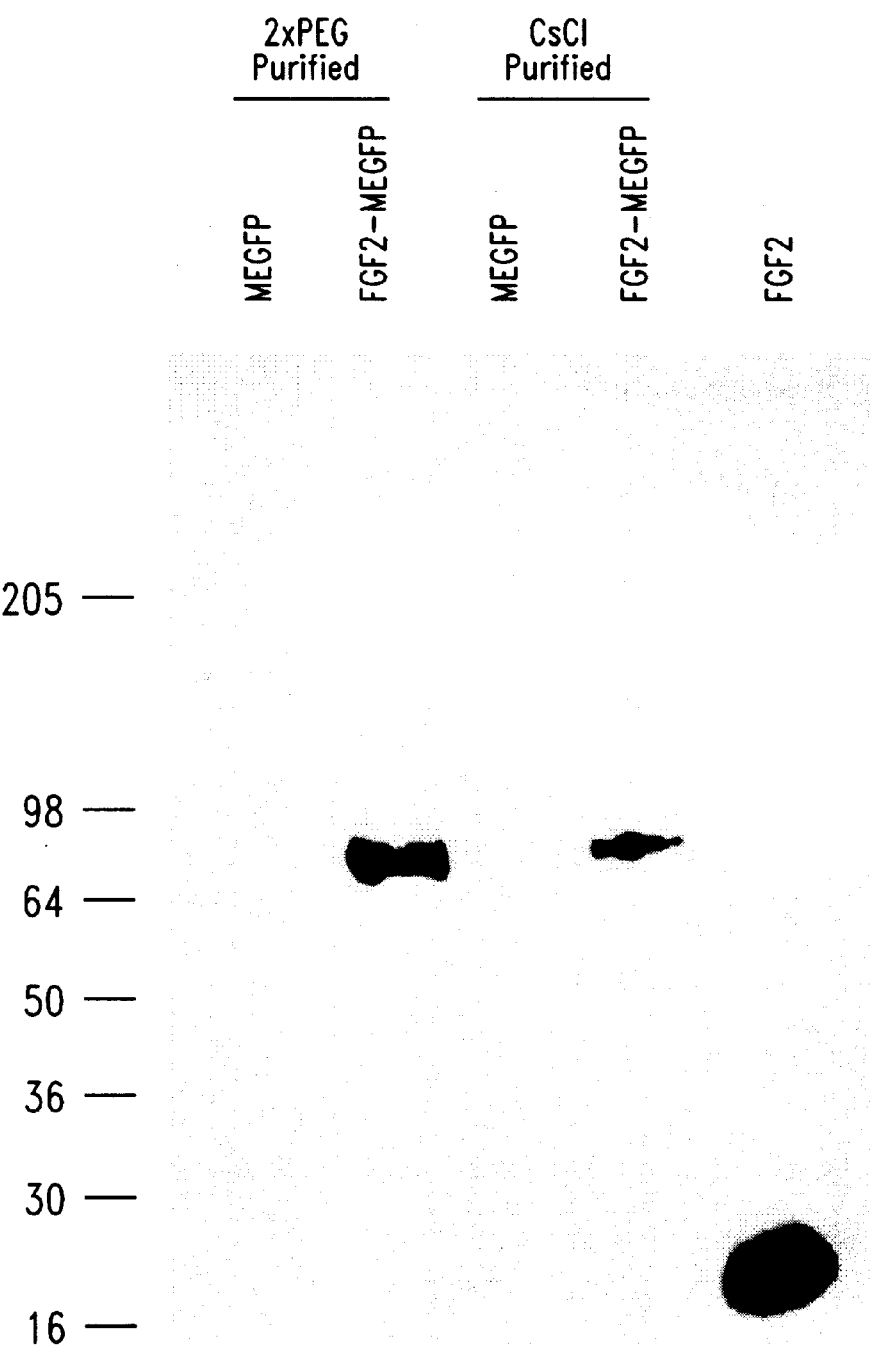
FIG. 2 is a scanned image of a Western Blot analysis representing detection of FGF2-pIII fusion protein in protein extracts from purified FGF2-phage (FGF2-MEGFP).

To facilitate cloning, the FGF2 gene is amplified by PCR using oligonucleotide primers that contain appropriate restriction endonuclease sites in the phage vector gene III or VIII genes. The resulting phage express FGF2 on their surface coat as detected by anti-FGF2 antibodies in Western blots (FIG. 2) and by ELISA (FIG. 3).

Western blot detection of FGF2-pIII fusion utilizes extracts from equivalent phage titers of purified FGF2 phage and control phage (MEGFP3) separated by polyacrylamide gel electrophoresis and blotted onto nitrocellulose. FGF2 and FGF2-fusion phage are detected with an anti-FGF2 monoclonal antibody (Transduction Labs; Lexington, Ky.) and HRP conjugated anti-mouse secondary antibody (American Qualex; San Clemente, Calif.) with chemiluminescent development. A single protein band is detected in the cesium chloride purified FGF2-phage extract migrating at about 80 kDa. This is about the size predicted for the FGF2-pIII fusion protein (FGF2 (18 kDa) fused to pIII (migrates-60 kDa)). CsCl purification is performed to remove any non-covalently bound FGF2 fusion protein from the phage particles.

Figure 3A:
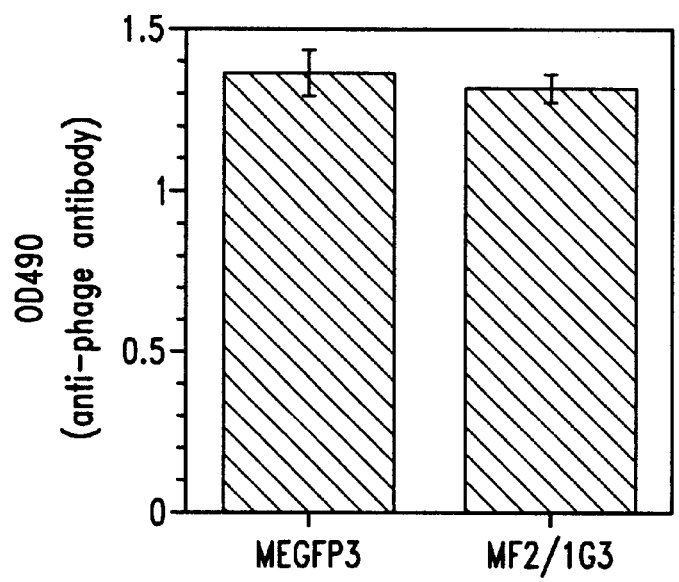
FIGS. 3A and 3B are bar graphs of ELISA detection of FGF2 on FGF2-phage.
Figure 3B:
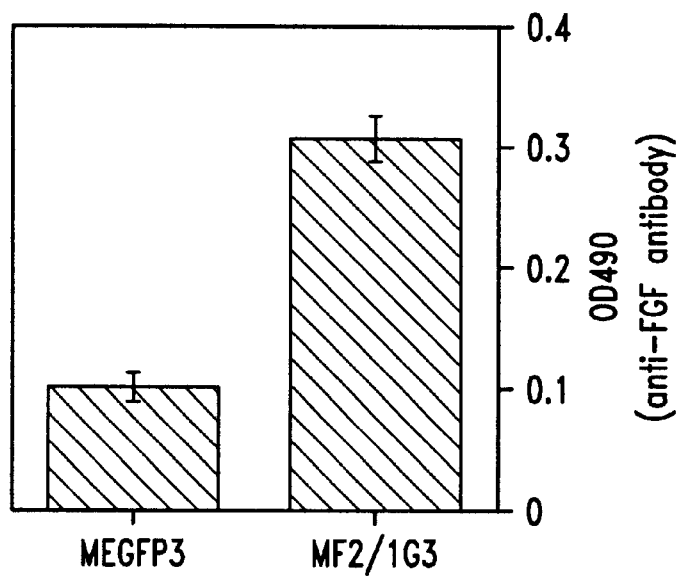

Binding of the FGF2 fusion phage to FGF2 receptor is assessed by ELISA in which recombinant FGF2 receptor is attached to the solid phase and an anti-phage antibody is used as the primary detection antibody. Briefly, phage were captured with an anti-FGF2 rabbit polyclonal antiserum bound to the plate well. An HRP conjugated anti-M13 antibody (Pharmacia Biotech; Piscataway, N.J.) was used to detect the bound phage. When anti-phage antibody is used to capture the phage and equivalent OD is observed for both control (MEGFP3) and FGF2-phage (MF2/1G3) indicating that equivalent phage particles are applied to the plate (FIG. 3A). In FIG. 3B an increased OD indicates the presence of FGF2 on the MF2/1G3 FGF2-phage.

Example 3

Target Cell Line Engineering

To increase the sensitivity of the assay for transduction by ligand display phage the target cell line is transfected with a plasmid that is designed to express the SV40 large T-antigen (i.e. pSV3neo). This plasmid also contains a drug selection gene such as neomycin phosphotransferase (neo) which confers resistance to the antibiotic G418 in stabley transfected mammalian cells. Following transfection of the target cell line with plasmid DNA using standard methods (i.e. $CaPO_4$ co-precipitation) the cells are split and maintained in G418 containing media until drug resistant colonies appear. The colonies are expanded to test for SV40 T-antigen synthesis by western blotting or immunoprecipitation using a suitable antibody. Examples of T-antigen expressing target cell lines are: BOS (BHK with SV40 T-Ag) for screening FGF variants; HOS-116 (HCT116 with SV40 T-Ag) for screening peptides that target human colon carcinoma; AOS-431 (A431 with SV40 T-Ag) for screening EGF variants (all parent cell lines are available from ATCC, Manassas, Va.)

Example 4

Binding and Internalization of FGF2-Expressing Phage

The FGF2-expressing phage are also assayed for high affinity receptor binding and internalization in receptor bearing cells by immunolocalization and fluorescence microscopy (Hart, J. Biol. Chem. 269:12468–12474, 1994; Barry et al., Nature Med. 2:299–305, 1996; Li, Nature Biotech. 15:559–563, 1997).

Infection of mammalian cells with FGF2-expressing phage is performed under conditions that block entry of wild type M13 phage into cells except chloriquine is not used (Barry et al., supra). Phage are added directly to cells at titers of $\leq 10^{10}$ CFU/ml in PBS with 0.1% BSA or other suitable blocking agents and incubated at 37° C. or on ice for at least 1 hour. The cells are then washed extensively in PBS, fixed in 2% paraformaldehyde, and permeabilized in 100% methanol at room temperature for 10 minutes. Cells are incubated with rabbit anti-M13 antibody (Sigma; St. Louis, Mo.) in PBS/BSA for 1 hour. The primary antibody is detected with a phycoerythrin labeled anti-rabbit antibody (Life Technologies (Gibco BRL); Rockville, Md.). Surface bound (incubated on ice) or internalized (37° C. incubation) phage are detected by fluorescence microscopy.

Example 5

Transduction of Mammalian Cells by FGF2-Ligand Display Phage

Figure 4A:
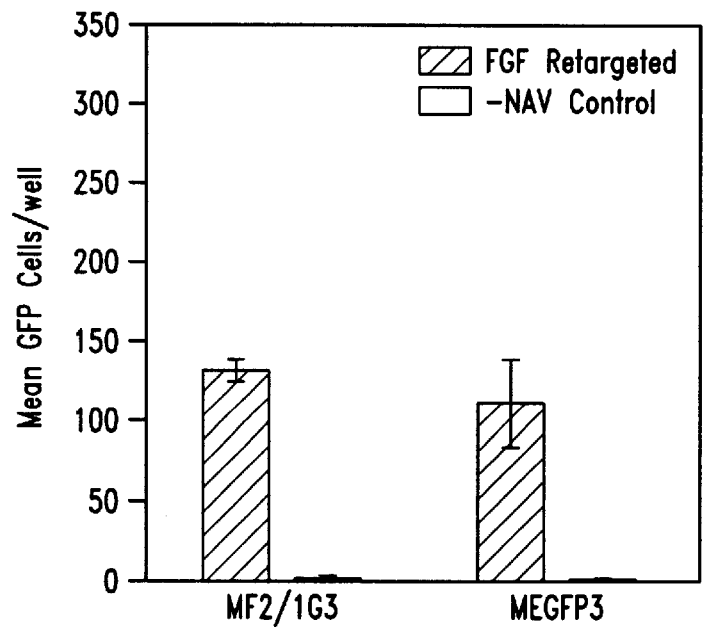
FIGS. 4A and 4B are bar graphs representing the transduction of COS cells by FGF2-phage.
Figure 4B:
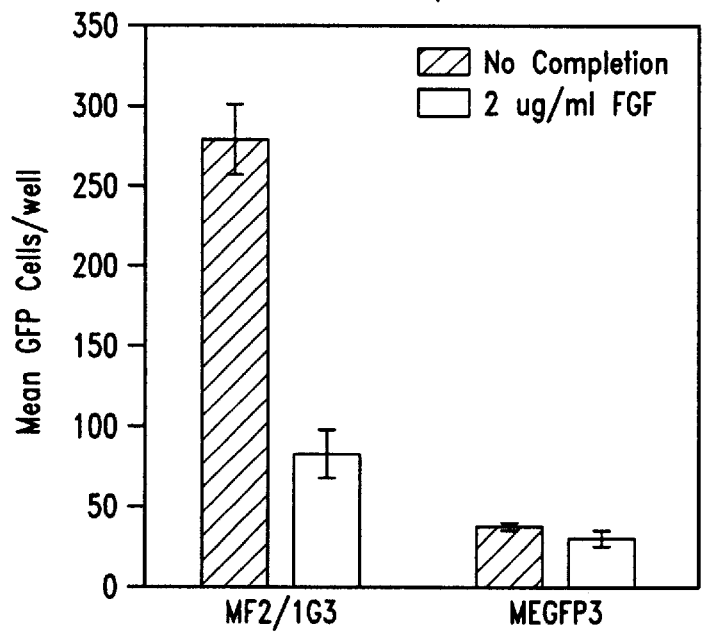

FGF2 display phage (MF2/1G3) and an identical phage that lacks the FGF2 gene (MEGFP3) are compared for receptor mediated internalization and reporter gene expression in COS cells. The phage are incubated with the cells for 4 hours at 37° C. in DME (Dulbecco's modified Eagles medium, Life Technologies (Gibco BRL); Rockville, Md.) containing 2% BSA (bovine serum albumin) as a blocking agent. After washing to remove unbound phage the cells are returned to the incubator for an additional 72 hours. Transduction is measured by counting GFP positive autofluorescent cells. As shown in FIG. 4B, the FGF2 display phage result in about a 10 fold greater transduction efficiency than the control phage indicating that the displayed FGF2 ligand on the surface of the phage particles results in receptor mediated binding and internalization of phage with subsequent expression of the phage reporter gene. The specificity of the FGF2-phage mediated transduction is demonstrated by successful inhibition of transduction with excess free FGF2 (2 µg/ml) (FIG. 4B). The low level nonspecific uptake and transduction by the control phage (MEGFP3) is not affected by the presence of excess FGF2.

It is important to show that the MEGFP3 control phage is equally capable of transducing mammalian cells as the display phage when appropriately targeted. To compare the transduction ability of both the FGF2-phage and the control phage, equivalent titers of each phage were used to transfect COS cells using a avidin-biotin FGF2 targeting method. In this method biotinylated FGF2 is contacted with the cells and used to capture phage particles via the addition of avidin and a biotinylated anti-phage antibody. The phage/FGF2/cell binding is performed on ice, unbound phage removed by washing, cells returned to the incubator at 37° C., and transduction assessed at 72 hours. As seen in FIG. 4A, there is no significant difference in transduction between FGF2-phage and control phage when FGF2 is attached to the phage via an avidin biotin linkage. In this case the biotinylated FGF2 is in excess of the FGF2 displayed on the phage surface such that internalization is expected to be primarily via the biotinylated FGF2. These data demonstrate specific receptor mediated transduction of mammalian cells by filamentous phage that genetically display a targeting ligand (FGF2).

Example 6

Construction of a Reporter Gene and a Drug Resistance Gene in Phage Display Vectors A GFP expression cassette consisting of the GFP gene (Cormack et al., Gene 173:33–37, 1996) under control of a CMV promoter, a neomycin phosphotransferase gene under control of the SV40 early gene promoter, and an SV40 origin of replication are cloned into a gene III phagemid vector such as pCANTAB 5E using standard methods (Sambrook et al., *Molecular Cloning: A Laboratory Manual*, Cold Spring Harbor Press, 1989). The resulting phage is designated pmaM13. The same phagemid genome also containing FGF2-3 fused to gene III is designated pFGF-maM13. Similar constructs are also made with M13 phage type3 and type 33 and gene VIII phagemid and phage vectors. Recombinant phage displaying FGF2 on the coat and carrying the mammalian expression cassettes including the SV40 replication origin are prepared by phagemid rescue with M13K07 (or suitable helper phage) are added to COS cells as described above. GFP expression is detected by fluorescence microscopy, fluorometry, and flow cytometry at 48–96 hours after phage addition. Drug resistant cells are selected with G418.

Example 7

Selection of FGF2-Expressing Phage from a Mixed Population

A M13 phage display library of random or unknown sequences is spiked with pFGF-maM13 phage. The mixture is used to infect COS cells as described above. The cells are washed extensively to remove non-specifically bound phage. Cells are re-plated 48–96 hours later at a 1 to 10 dilution and grown in G418 to select only cells that receive the transducing phage gene. Alternatively, the GFP expressing cells are isolated by flow cytometry using an excitation wavelength of 488 and emission wavelength of 510.

DNA is extracted from G418-resistant cells and the FGF2 sequence is amplified. The amplification primers have sequences complementary to phage sequences located on each side of the FGF2 sequence in the gene III coding sequence. Detection of the FGF2 sequences in selected COS cells that are infected with a mixture of phage where the pFGF-maM13 phage is diluted at least 1:10,000 with the random sequence phage library demonstrates feasibility of the technique.

Example 8

Identification of FGF2 Variants for Improved Gene Delivery

A library of shuffled FGF2 mutants is created using the gene shuffling method described by Stemmer (supra). The FGF2 gene is amplified by PCR and fragmented by DNAse 1 treatment. The fragments are reassembled using PCR in the absence of primers. The reassembled gene is cut with the appropriate restriction enzymes and cloned into an M13 phage vector such that the FGF mutants are fused in-frame with the pIII coat protein gene. The phage vector contains a CMV promoter driven GFP reporter gene and an SV40 origin of replication. Several individual phage clones are sequenced to confirm that an average of 3 mutations per phage have been generated during the reassembly process. The resulting phage library of FGF2 mutations is amplified by standard protocols. The target cell line, BOS (BHK with T-Ag) is incubated with the library such that each member of the library is at an m.o.i. of at least 10. Accordingly, $10^{11}$ phage representing $10^6$ copies of $10^5$ individual phage species are applied to $10^5$ cells. The phage are incubated with the cells in PBS supplemented with 2% fetal bovine serum for 1–3 hours, after which non-binding phage are removed by extensive washing with PBS. Media is added and the cells are returned to the incubator at 37° C. to allow phage internalization.

Example 9

Screening Libraries for Gene Delivery Ligands

If the source of the desired ligand is not known, random peptide libraries or a cDNA library from placenta is used as a starting point for cDNA library screening. The library is amplified in the maM13–33 phage by infecting DH5αF' (or other suitable host) bacteria, growing the culture overnight at 37° C. and isolating the phage from the culture medium using standard protocols. A cDNA library containing $10^5$ members has each member represented $10^6$ times in a typical phage titer of $10^{11}$ colony forming units/ml. The amount of phage used to infect is adjusted to the complexity of the library.

The completed maM13 phage library is screened against the target tissue or cell line. Screening can be performed in-vitro or in-vivo. The criteria for a positive "hit" is that the phage must be able to bind, be internalized, translocate to the nucleus, uncoat and replicate and express the genomic DNA containing the reporter gene in the target cell. Thus, only transduced target cells are selected either by GFP expression and cell sorting or drug resistance. Screening is performed directly against the target cells with no prescreening or enrichment. Enrichment for cell binding is performed if no hits are found in the initial screen. A prescreen to select out phage that bind non-specific cells surface proteins is performed to reduce non-specific hits or if there are too many initial hits. Infection of at least $10^7$ target cells is performed with at least $10^{11}$ phage. The cells are incubated for at least 2 hours in PBS and washed extensively as described by Barry (Barry et al., *Nature Med.*, 2:299–305, 1996). The cells are incubated in media at 37° C. for 48–96 hours and selected in the appropriate drug (e.g., G418) for 7–14 days or until resistant colonies are visible microscopically. Drug resistant colonies are pooled, and the selected cDNAs amplified and subcloned back into the maM13–33 phage vector using PCR and standard molecular biology methods. Alternatively individual colonies are screened. Representative phage clones are sequenced to identify potential gene delivery ligands. Repeated rounds of infection and selection are performed to reduce the complexity of the selected clones. More stringent screening conditions such as increased selective drug concentrations or FACS sorting or the strongest fluorescent cells are performed in the later screens to select the most highly efficient gene delivery ligands from the initial screening.

Screening in-vivo is performed using methods previously described by Pasqualini for targeting organs or xenograft tumors using phage displayed peptides (Pasqualini, R. et al., *Nature Biotechnology*, 15, 542–546 (1997); Pasqualini, R. et al., *Nature*, 380, 364–366 (1996)) except that the organs or tumors are examined for reporter gene expression instead of the presence of phage. The phage library is injected intravenously into mice and organs or tumor samples tested for reporter gene function at 48–96 hours after injection. Tumor cells are cultured in G418 or FACs sorted (for GFP expression) to enrich for cells that express the phage transducing gene. The ligand encoding sequences are amplified from selected cells using PCR as described for in-vitro screening. As in in-vitro screening, repeated rounds of infection and rescreening are performed at increasing screening stringency to obtain the most efficient gene delivery ligands.

Example 10

Identification of Ligands that Target Colon Carcinoma

In this example, a library of oligonucleotides encoding random peptides is inserted into a filamentous phage genome such that the peptides are fused to the C-terminus of intact pIII coat proteins. A type 3 phage vector that only contains one copy of the pIII gene is used and, therefore, all of the pIII protein that is made will be fused to a peptide. Thus, 3–5 copies of a peptide is displayed on each phage. To simplify the screening the complexity of the library is first reduced by screening it for internalizing peptides. Peptides that facilitate the internalization of phage into a colon carcinoma cell line are isolated through several rounds of selection. The phage library is incubated with the cells for 3 hours at room temperature. The cells are washed extensively in PBS. A brief proteinase K treatment is used to inactivate phage that adhere to the cell surface. The cells are then lysed and cell lysates incubated with host bacteria. Internalized phage are amplified in bacteria and subjected to 4 or more iterations of exposure to cells and recovery of internalized phage. Replicative form DNA is prepared from the resulting sublibrary of internalizing phage. The random sequences in the sublibrary are subcloned into a phage vector MEGFP2 that contains a copy of the CMV driven reporter gene (GFP) and an SV40 replication origin. MEGFP2 differs from MEGFP3 (FIG. 1A) in that the ori-CMV/EGFP expression cassette is in the reverse order, EGFP is followed by an SV40 polyadenylation site instead of Bovine Growth Hormone poly A, and the vector contains three additional Nco I sites within the ori-CMV/EGFP expression cassette.

The resulting CMV-GFP modified sublibrary is incubated with the HOS-116 recipient cell line such that each member of the library is represented at least $10^6$ times. Thus, for example, a library with $10^5$ members is added to $\sim 10^5$ cells at a titres of $\sim 1 \times 10^{11}$ yielding an m.o.i. for each member of at least 10. The phage are incubated with the cells in PBS supplemented with 2% fetal bovine serum for 1–3 hours, after which non-binding phage are removed by extensive washing with PBS. Media is added and the cells returned to the incubator at 37° C. to allow phage internalization.

Example 11

Recovery of Ligand Encoding Sequences from Replicative Phage

At 72 hours following the addition of the phage library. The target cells are removed from the plate and sorted for GFP expressing cells by FACS. The positively sorted cells are lysed and treated with proteinase K. The proteins are extracted with phenol/chloroform (24:1 solution) and nucleic acids precipitated in ethanol. The resulting DNA is resuspended in S1 nuclease buffer and treated with S1 nuclease to remove non-replicative single strand phage DNA. The DNA is again extracted with phenol/chloroform, precipitated, and resuspended in polymerase chain reaction buffer. Alternatively, nuclei are prepared from the positive cells, proteinase K treated and the lysate used directly in the PCR reaction. In either case, an equivalent number of negatively sorted cells are treated in parallel and used in the PCR reaction to monitor the enrichment of replicative phage DNA (double-stranded) over non-replicative phage DNA (single stranded) such that there is no phage DNA amplified in the samples from GFP negative cells. If phage DNA is amplified from negatively sorted cells then conditions must be made more stringent for the removal of single stranded phage DNA such as increasing treatment with S1 nuclease or further purification of nuclei through repeated sucrose step gradient purification or other suitable methods known for purification of nuclei (to remove non-replicative phage). These conditions might need to be determined empirically for each cell line and library used.

The phage sequence(s) encoding the ligand peptide is amplified using an appropriate set of oligonucleotide primers that flank the ligand encoding DNA sequence inserts that is fused to the pIII gene. These amplified inserts are recloned into the parent phage vector to create a sub-library of phage enriched now for gene delivery ligands for the target colon carcinoma cell line. Sequencing is performed on representative clones to determine the complexity. The screening process is reiterated until the complexity is reduced sufficiently to identify one or more targeting ligands.

Example 12

Second Generation Screening of Peptides

Peptides are selected which have been previously identified from a random library by one or more panning or screening procedures using conventional vectors and panning methods (see Kay et al., *Phage Display of Peptides and Proteins: A Laboratory Manual*, Academic Press, 1996). The DNA encoding the selected peptides is inserted as a fusion to the pIII coat protein in the MEGFP2 vector containing the GFP reporter gene cassette.

An M13 phage random peptide library is screened for peptides that bind and internalize in an FGF receptor over-producing cell line, F1g37 (an FGFR1 stable transfectant of L6 cells (available from the ATCC; Manassas, Va.) obtained from Dr. Murray Korc, UCI; Irvine, Calif.). In addition, such a cell line may be easily created by those skilled in the art. Following 5 rounds of panning and rescreening the complexity of the library is reduced such that 80% of the phage are represented by a single peptide-pIII fusion. The resulting peptide, FL5, has the sequence FVPDPYRKSR (SEQ ID NO: 1). The same library is also screened against F1g37 cells by selecting infective phage particles that internalize and associate with nuclei and cytoskeletal proteins. The 2 predominant peptide sequences identified by this screen after 5 rounds of panning are FN5A, CGGGPVAQRC (43%) (SEQ ID NO: 2) and FN5B, CLAHPHGQRC (34%) (SEQ ID NO: 3).

Figure 5:
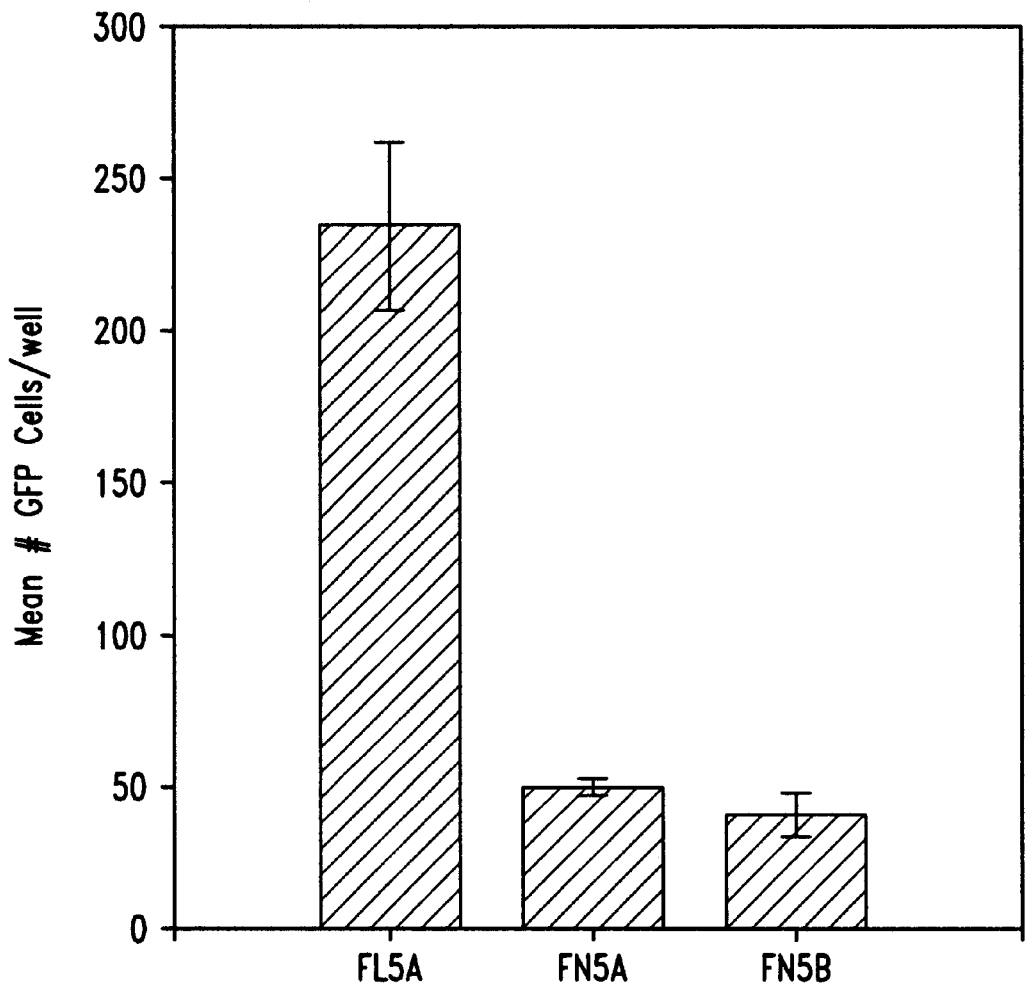
FIG. 5 is a bar graph representing the transduction of COS cells by peptide display phage.

Oligonucleotides encoding the 3 peptides are inserted into the MEGFP vector as fusions to the pIII coat protein. The resulting phage are used to transfect COS cells. Phage are added to cells and incubated overnight at 37° C. in medium with 10% fetal calf serum. The cells are washed to remove unbound phage and returned to the incubator. Transduction is assessed by counting GFP expressing autofluorescent cells at 72 hours after the addition of phage. The results (FIG. 5 are that a greater transduction efficiency is observed with FL5 than FN5A or FN5B indicating that FL5 is a more efficient as a gene transfer ligand in this system. The transduction screening method as a second generation screen is capable of distinguishing among peptides that were selected by different primary cell based screens.

Example 13

EGF Medicated Mammalian Cell Transduction

Figure 6:
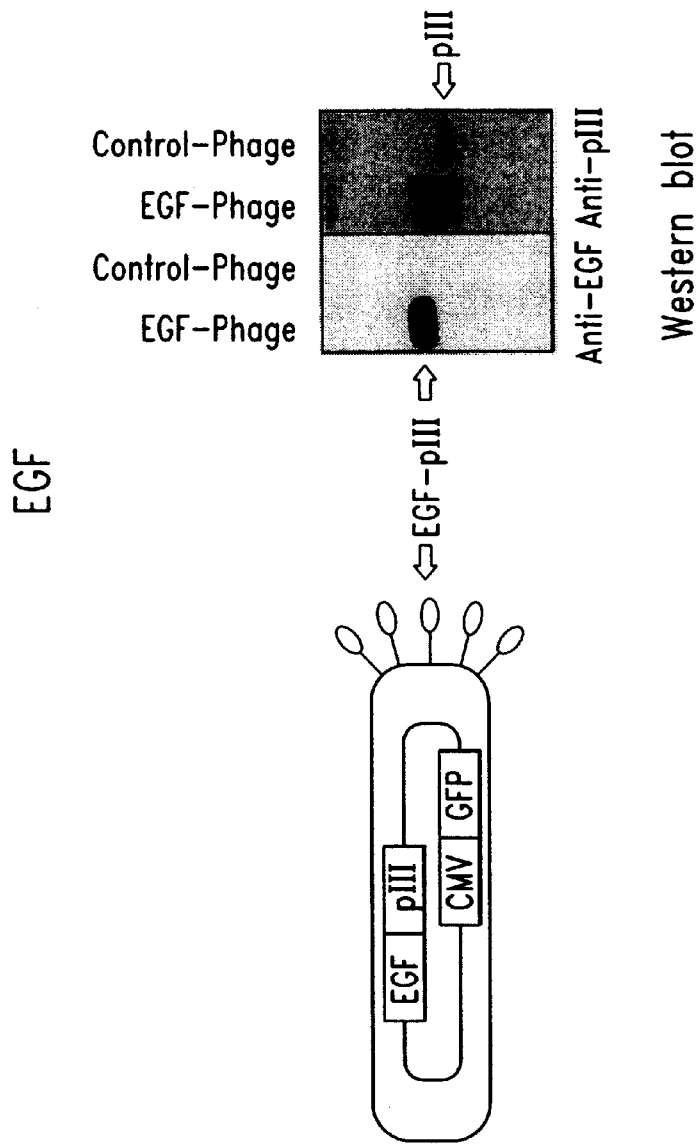
FIG. 6 is a scanned image of a Western Blot analysis representing detection of EGF-pIII fusion protein in protein extracts from purified EGF-phage.

Epidermal growth factor displaying phage were constructed as described above for FGF displaying phage. Western blot analysis demonstrates that EGF was efficiently expressed on the phage coat in a multivalent manner (FIG. 6). Phage were prepared for Western analysis by obtaining the EGF-phage from cultures of infected host bacteria and purified by PEG precipitation and CsCl gradient centrifugation. The phage particle proteins were then separated by gel electrophoresis and blotted onto a nitrocellulose membrane. Blots were then probed with either anti-EGF or anti-pIII antibody (mouse anti-human EGF, Biosource International; Camarillo, Calif.) or anti-pIII antibody (mouse anti-pIII, MoBiTech; Germany) followed by HRP-goat-anti-mouse (Jackson Laboratories, USA).

Figure 7:
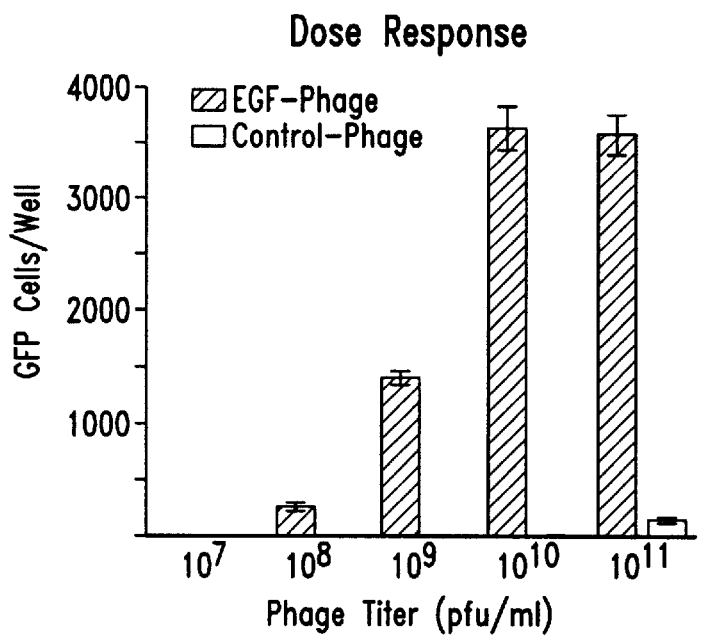
FIG. 7 is a bar graph representing the dose response of COS cells to various phage titers.
Figure 8:
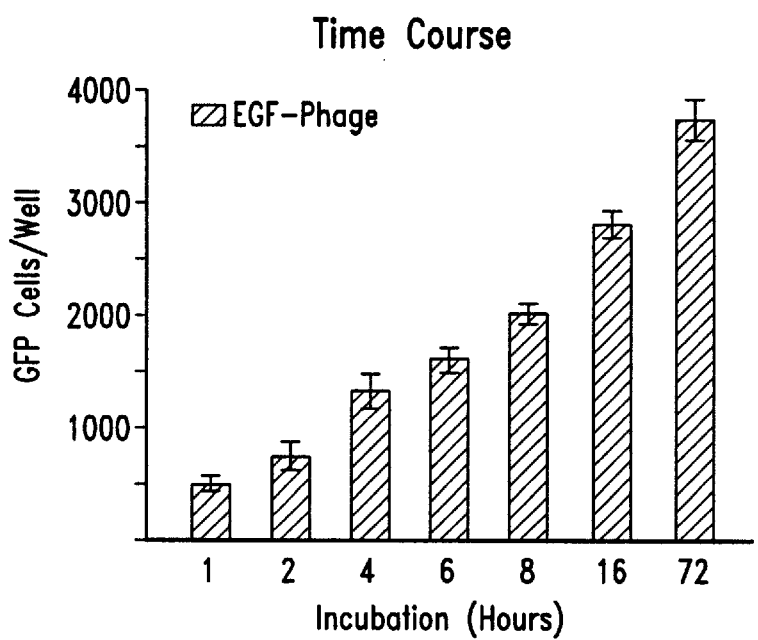
FIG. 8 is a bar graph representing a time course analysis of various incubation times and the effect on transduction.

Following the procedures detailed above, EGF-phage were screened for their ability to effectively transduce COS cells. Briefly, EGF-phage were incubated with COS cells (~75,000 cells/well) for 72 hours with a variety of phage titers. As demonstrated by FIG. 7 the optimal dose was $10^{10}$ pfu/ml which resulted in the highest transduction efficiency with almost no non-specific transduction by untargeted phage. Transduction efficiency also increases with longer incubation times. As demonstrated in FIG. 8 when EGF-phage were incubated with COS cells (~75,000 cells/well) at $10^{11}$ pfu/ml for various times and subsequently measured for GFP expression at 72 hours, longer incubation times increased transduction efficiency.

Figure 9A:
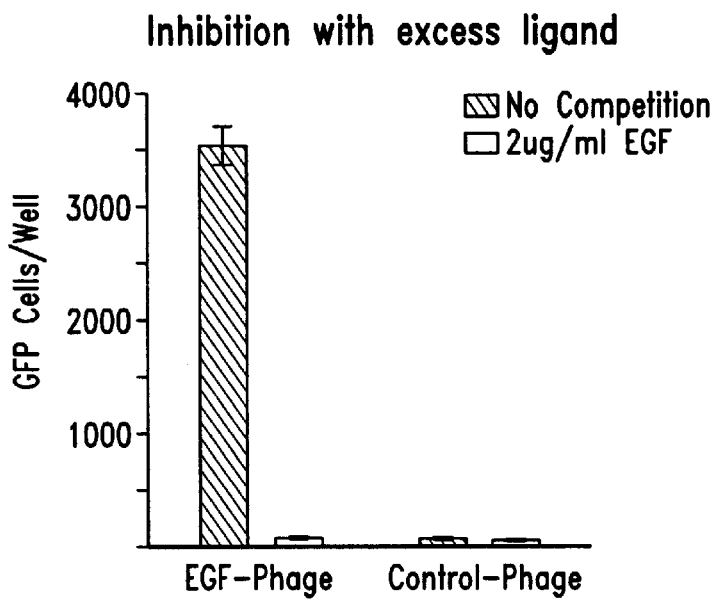
FIGS. 9A and 9B are bar graphs representing the specificity of transduction of COS cells by EGF-phage.
Figure 9B:
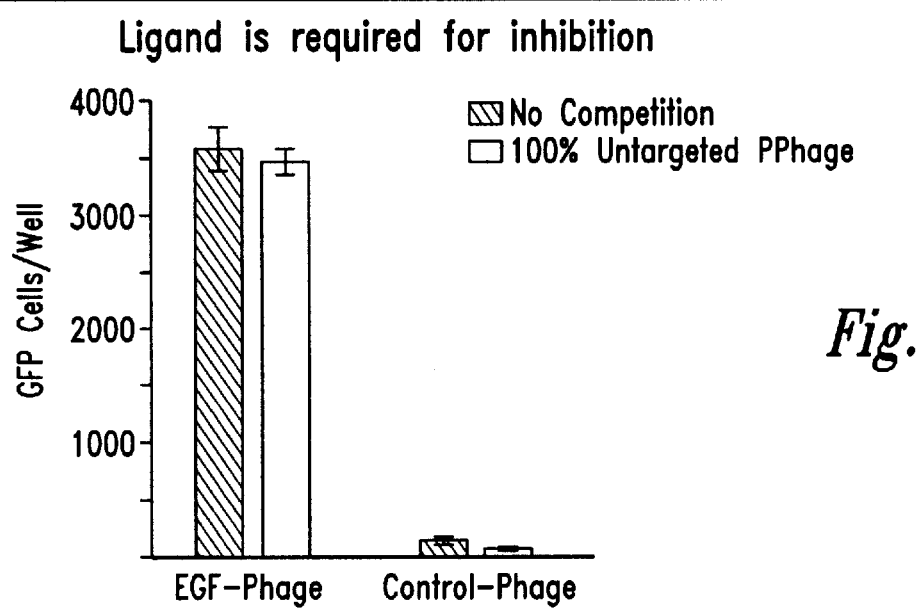

Further, specificity of EGF-phage mediated COS cell transduction was determined by incubating EGF-phage with excess ligand. As depicted in FIGS. 9A and 9B, COS cells incubated with $10^{11}$ pfu/ml of phage for 72 hours with or without excess ligand or untargeted phage demonstrate that targeting is due to the presence of the ligand.

Example 14

Simultaneous Identification of Internalizing Ligands and Anti-Ligand Binding Targets To identify internalizing ligand-anti-ligand binding target interactions, the putative ligand is displayed on the surface of filamentous phage that carry a mammalian reporter gene expression cassette. The candidate binding target peptides/proteins are expressed on the surface of COS cells by substituting the target cDNA for the extra cellular domain encoding DNA portion of the EGF receptor in a suitable mammalian cell expression vector (i.e., pcDNA 3.1; Invitrogen, Calif.).

To accomplish this, a library of cDNAs is inserted into a mammalian expression vector (pcDNA 3.1) such that the cDNAs are fused to the transmembranes and intracellular domains of EFG receptor cDNA. DNA is prepared from individual or pools of bacterial clones that have been transformed to carry the cDNA-receptor fusion protein expression plasmid. COS cells are transfected with the resulting plasmid DNAs in six well plates at low density. At 24 hours later, ligand display phage carrying the CMV driven reporter gene GFP are added to the transfected COS cells.

Binding of the phage displayed ligand to the cell surface display binding target (i.e. protein—EGF receptor fusion protein), results in dimerization of the receptor and subsequent internalization of phage that display the binding ligand. The internalized phage are trafficked to the nucleus where the reporter gene is expressed. 72 hours after adding phage, cells expressing the reporter gene are selected by FACs. cDNAs encoding reactive peptides are identified by the presence of GFP positive cells in the COS transfectants for each cDNA or cDNA pool. The binding ligand is identified by PCR amplification and sequencing of the phage ligand-pIII fusion gene. The target peptide is identified by PCR amplification and sequencing the peptide-EGF receptor fusion protein from the selected cell(s).

Example 15

Identification of Cell Targets

Phage that display a ligand as a pIII fusion on the phage coat and carry the GFP expression cassette are prepared using standard protocols, as discussed above. Control phage that carry GFP but don't display a ligand are also prepared. Candidate cell targets are seeded into 6 well culture plates at about 40,000 cells/well. At 24 hours after seeding cells, phage are added at ~$10^{10}$ pfu/ml. The plates are incubated at 37° C. for an additional 72 hours. Each cell well is scored by counting GFP positive autofluorescent cells. The cell types that have a ratio of GFP positive cells in the ligand-phage treated well/control phage treated cells of greater than 1.0 are selected as targets for further study and characterization. As an alternative to GFP, a drug resistance gene can be used in which case after 72 hours the cells are allowed to continue growth in selective medium containing the drug. Positive cell types are scored by counting wells that have drug resistant colonies.

Figure 10:
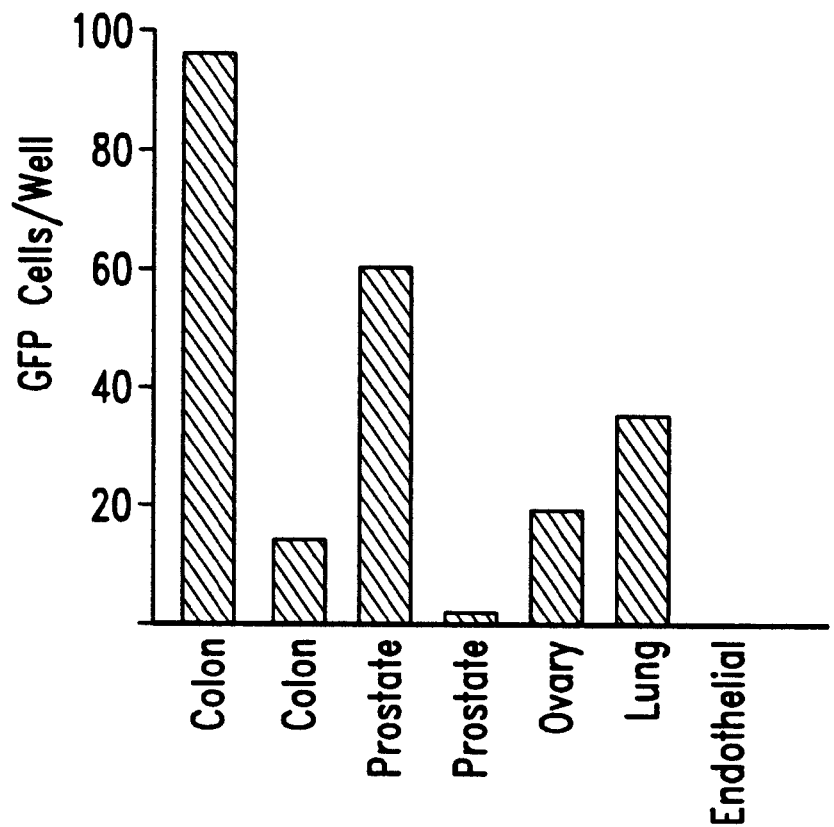
FIG. 10 is a bar graph representing transduction specificity of a variety of human carcinoma cells.

Carcinoma cell lines which are known to express EGF were screened by the above method using EGF-phage and compared to the control endothelial cell line which is EGF receptor negative (Cell lines obtained from ATCC, Manassas, Va. and grown under standard ATCC culture conditions). As shown in FIG. 10, the carcinoma cell lines derived from various tissues were differentially transduced while the receptor negative, endothelial cells displayed no transduction. Accordingly, identification of target cells or tissues can be accomplished using these methods.

Example 16

Identification of Pathogen Cells

Ligand display phage are constructed as discussed above, with the ligand being full-length or fragments of coat or envelope proteins of a known or suspected pathogen. The ligand expressed on the display phage coat can be expressed from the cDNA or cDNA derivative of the coat or envelope protein of a known or suspected pathogen (e.g., HIV envelope protein gene). The envelope gene is randomly fragmented to form a library of display phage display distinct portions of the coat protein. Thereby allowing determination of the portion of the gene that encodes a protein that functionally interacts with the host cell surface receptors allowing internalization. Smaller pathogen coat proteins are displayed in entirety. The pathogen coat display phage acts as surrogate pathogen with the advantage of providing a simple assay for detection of host cells. Phage displaying coat protein are screened against various cell types in vitro as described above or in vivo by injection and subsequent identification of target cells and tissues by fluorescent microscopy, FACS analysis to detect GFP, or growth in selective medium to detect expression of a drug resistance marker.

Example 17

Identification of Pathogen Ligands

The gene(s) or portion of a gene that interacts with the host cell surface receptor to allow internalization is identified by making a phage display library of the cDNAs expressed by the pathogen or of the pathogen genome or fragments of the genome. The display library phage vector carries the GFP or suitable reporter gene driven by the mammalian promoter, as described above. The libraries are then screened against a known or putative host cell types by detecting transgene expression (i.e., drug selection or other detectable marker). Once cells are identified, the sequence of the nucleic acid encoding the internalizing ligand is determined by PCR sequencing of the pIII-putative ligand fusion construct.

Example 18

Identification of Secreted and Internalizing Ligands for Tumor Cells

Tumor cells interact with surrounding host stromal and other cell types via chemo-attractants and other factors which, for example, stimulate the stromal cells to secrete factors that support tumor growth (i.e., VEGF). To investigate these interactions, a library of putative secreted ligand cDNAs is prepared from tumor cell mRNA and selected by methods known in the art such as epitope-tagging, Sloan et al., *Protein Expression and Purification* 11:119–124, 1997. The secreted protein encoding cDNAs are inserted into the reporter phage vector as described above.

Individual phage clones or pools of phage clones are screened against various stromal cell types to identify cell types that are targets for tumor cell secreted factors, and to identify the secreted factors. The inverse strategy can also be applied by screening a library of, for example, fibroblast or other stromal cell secreted protein encoding cDNAs for factors that bind and internalize into various tumor cell types.

Example 19

Selection of EGF-Expressing Phage from a Population of Non-Targeted Phage

Non-targeted M13 phage was spiked with EGF-phage. The mixture was used to infect COS cells and incubated for 72 hours, as described above. The cells are washed extensively to remove non-specifically bound phage. The GFP expressing cells are isolated by flow cytometry (FACS) using an excitation wavelength of 488 and emission wavelength of 510.

DNA is extracted from GFP positive cells and the EGF sequence was amplified by PCR. The amplification primers have sequences complementary to phage sequences located on each side of the EGF sequence in the gene III coding sequence. These sequences were re-cloned into the phage vector and new phage were prepared for subsequent rounds of selection.

Briefly, the following biotinylated oligonucleotides were used to amplify the ligand gene III fusion:

However, the following have also been used with success:

```
                                          (SEQ ID NO: 7)
M8for2B  30 biotin   GCGTGGGCGATGGTTGTTGTCATTGTCGGC
                                          (SEQ ID NO: 8)
M3revB   25 biotin   CCACAGACAACCCTCATAGTTAGCG
```

Proteinase K treated nuclear preparations of FACsorted COS cells. PCR is carried out using Clontech's Advantage GF polymerase mix and cycled under the following conditions:

| 1 cycle: |
| --- |
| 94° C. 1 min. |
| 40 cycles: |
| 94° C. 20 sec. |
| 60° C. 20 sec. |
| 72° C. 20 sec. |

Following amplification, duplicate samples were combined and purified using Qiaquick columns (Qiagen Inc., Valencia, Calif.). The PCR products were then digested with NcoI and PstI restriction endonucleases. While SA-magnetic beads or other means for removal of "ends" of fragments increases ligation efficiency, such removal is not required. The digestion product is ligated into a new phage vector and used to transform competent cells by electroporation.

After sub-cloning and electroporation of bacterial cells, the bacteria were plated in top agar and grown overnight at 37° C., plaques were selected from plates and analyzed via PCR using oligonucleotides as follows:

```
MANPgIIIf 20 TTTTGGAGATTTTCAACGTG    (SEQ ID NO: 9)

MANPgIIIr 20 TGCTAAACAACTTTCAACAG    (SEQ ID NO: 10)
```

However, the oligonucleotides listed previously above, are equally useful.

Figure 11:
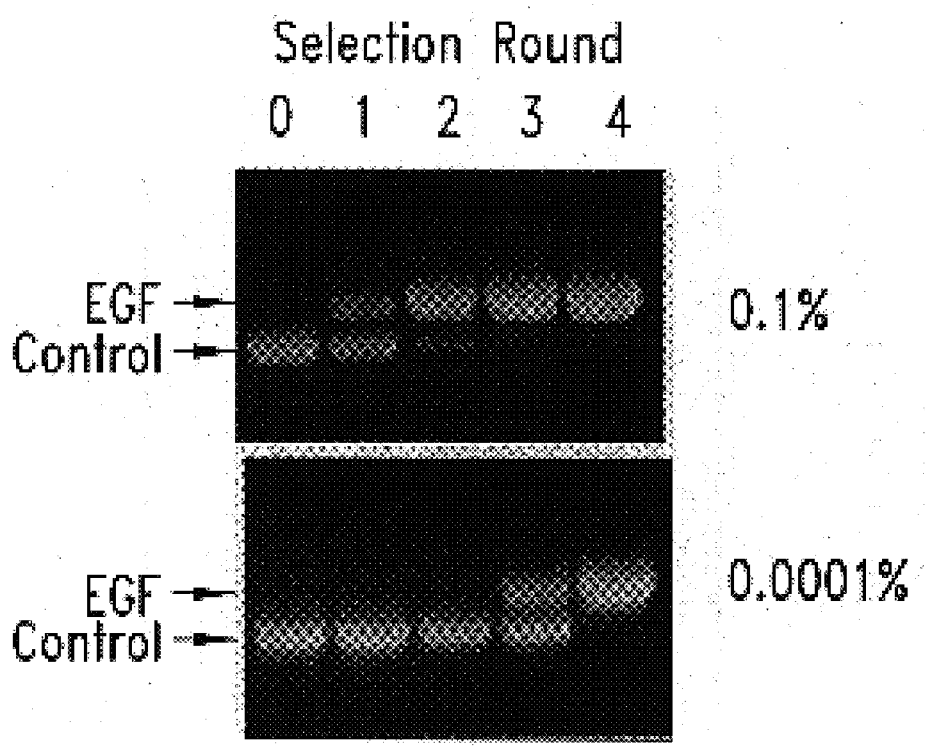
FIG. 11 is a scanned image of ethidium bromide stained gel electrophoretic analysis of products obtained by PCR amplification of pIII genes/pIII gene fusions following various rounds of selection.
Figure 12:
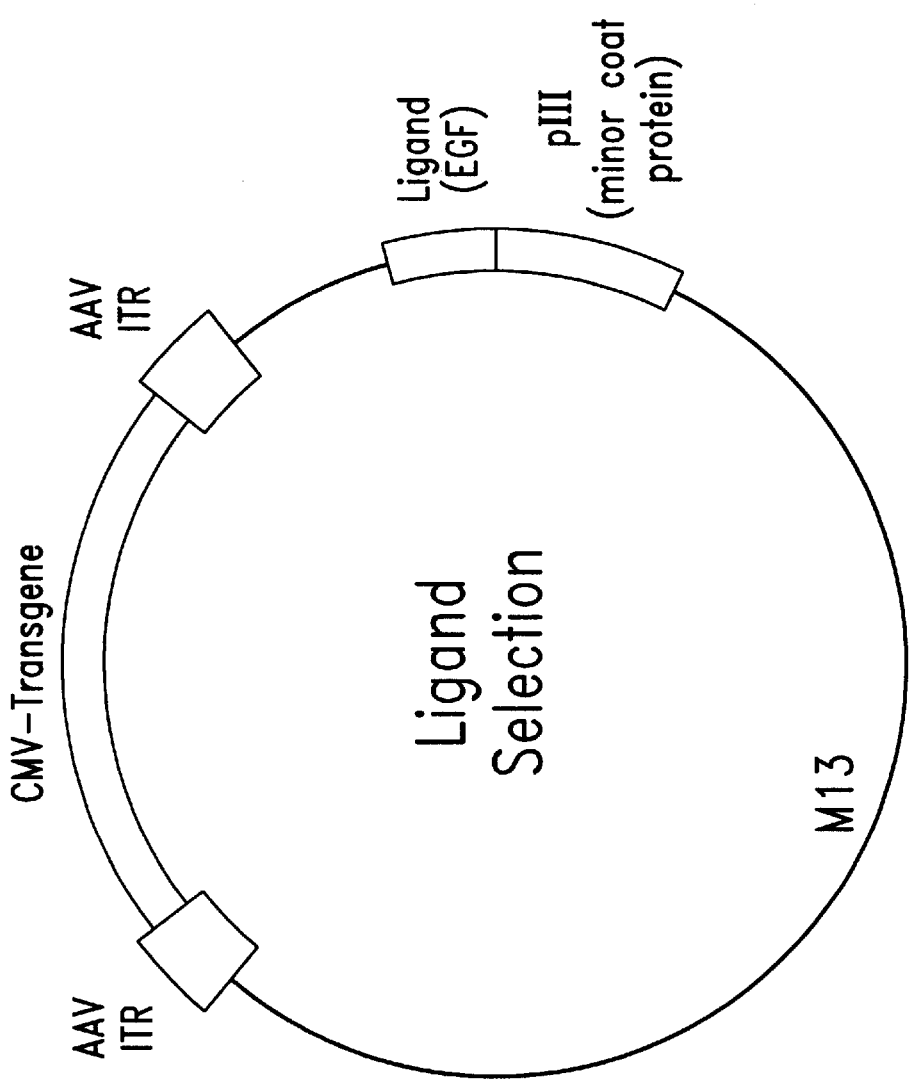
FIG. 12 is a vector map of an AAV-Phage hybrid genome vector.
Figure 13:
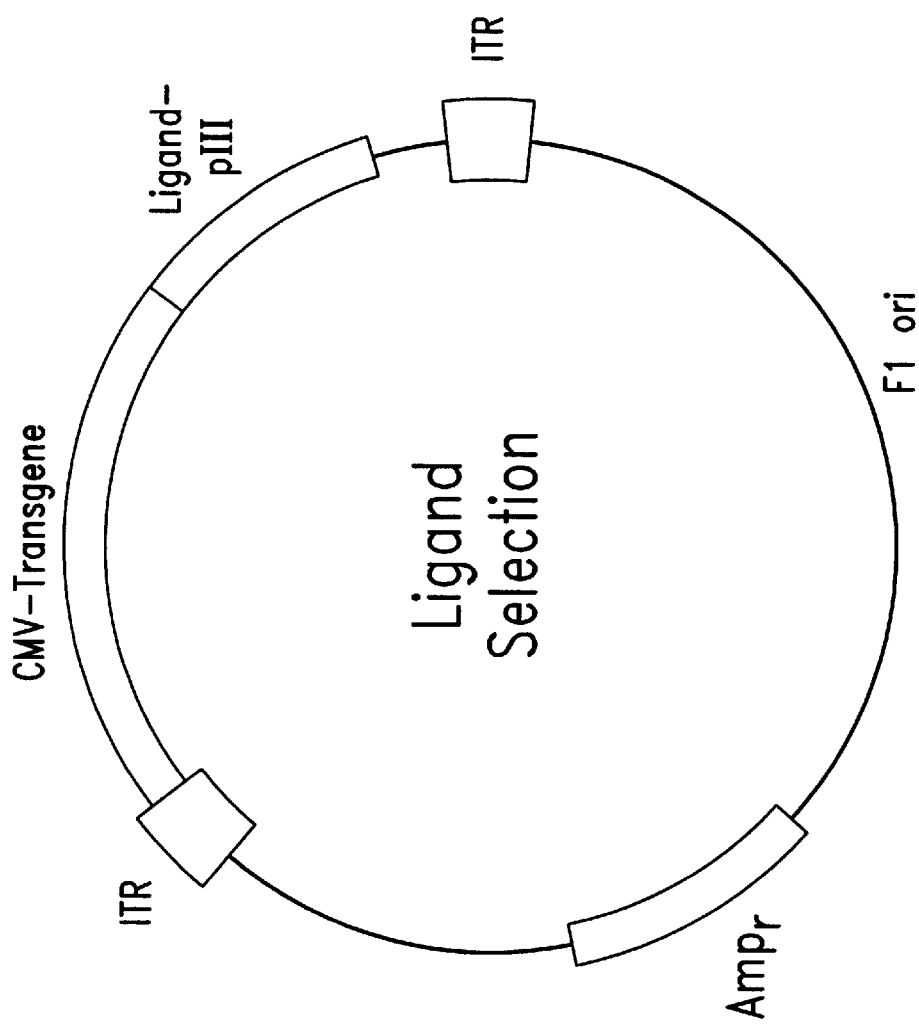
FIG. 13 is a vector map of an AAV-Phage hybrid phagemid vector.

As demonstrated in FIG. 11, enrichment of targeted EGF-phage from 0.1% to 100% EGF-phage was complete after 3 rounds of selection and enrichment from 0.0001% to 100% EGF-phage was complete after 4 rounds of selection. Accordingly, this experiment demonstrates the ability to select a specific ligand expressing phage from a population at dilutions of $1:10^3$ and $1:10^6$. In addition, while further diluted ligand expressing phage can be detected, further rounds of selection may be necessary.

Example 20

Creation of a Sub-Library of Peptides that are Internalized and Trafficked to the Nucleus Phage that display a candidate ligand as a pIII or pVIII fusion on the phage coat are prepared using standard

```
Anchor1M8f 48 5'Bio  AAAGGATCCGGGTTCCCGCGTGGGCGATGGTTGTTGTCATTGTCGGC  (SEQ ID NO: 5)

M3rev2     25 bio    CCGTAACACTGAGTTTCGTCACCAG                       (SEQ ID NO: 6)
``` protocols, as discussed above. In the present experiment a phage library (MANP-TN10, Dyax, Corp.) is used. COS cells are plated on 2×10 cm plates at about 105,000 cells/plate. At 24 hours after seeding cells, phage are added at ~$10^{10}$ pfu/ml. The plates are incubated at 37° C. for an additional 72 hours. The cells are then harvested in Trypsin-EDTA and pelleted. The cells are re-suspended in 0.5 ml of PBS and under-layed with 0.5 mls of nuclear isolation buffer (NIB) and spun at 200×g for 8 minutes at 4° C. (NIB=40% Sucrose, 0.1% DMSO, 2% NP40, 1.6% Triton X-100, 0.2 mM AEBSF (4-(2-Aminoethyl)benzenesulfonyl Fluoride, in PBS). The pellet is then re-suspended in 400 μl 1%NP40 and under-layed with 40% sucrose and again spun at 200×g for 8 minutes at 4° C.

The pellet is then re-suspended in 100 μl PKB (Proteinase K Buffer—50 mM Tris-HCl pH 8.5, 1 mM EDTA, 0.5% Tween-20). 1.4 μl of PK (Proteinase K from Boehringer Mannheim, 14 mg/ml) is added and incubated at 55° C. for 3 hours, then heated to 95° C. for 15 min. The DNA is then pelleted at maximum speed in a microfuge and washed 1 time with 70% ethanol followed by air drying in a hood. The resulting pellet is resuspended in a 20 μl of 10 mM Tris pH 7.2 and the ligand gene III fusion is amplified as described in Example 19, above, except that the cycling program was adjusted as follows:

| 1 cycle: |
| --- |
| 94° C. 1 min. |
| 25 cycles: |
| 94° C. 20 sec. |
| 60° C. 20 sec. |
| 72° C. 20 sec. |

Following amplification, the product was purified using a Qiaquick column (Qiagen) followed by digestion using NcoI and PstI restriction enzymes, as described above. Biotinylated fragments are removed using streptavidin conjugated beads (Promega Corp., Madison, Wis.), and the resulting sample is ethanol precipitated. The precipitated DNA is then washed and re-suspended in 10 μl of 10 mM Tris pH 8.5 and ligated into the reporter gene carrying phage vector. Following ligation the DNA is ethanol precipitated, washed, and used to transform competent cells (Stratagene electrocompetent cells X11Blue MRF'). Phage selected for in this manner (TN10nuclear selection) are then compared to non-selected phage (TN10library). The comparison of the pre-selected pool demonstrates that a significant population of the library which did not internalize has been removed in one round of screening, see Table below:

phagemid (e.g., any vector containing a phage origin of replication, such as pCOMB3, pBS+, pCR, and the like). The MEGFP3 vector has been modified with a mammalian expression cassette designed to express the reporter gene GFP to monitor mammalian cell transduction by the phage. Other vectors include pCANTAB 5 E (Pharmacia Biotech; Piscataway, N.J.) or M13 type 3 or 33 for gene III fusions (see Kay et al., Phage Display of Peptides and Proteins: A Laboratory Manual, Academic Press, 1996; McConnell et al., *Mol. Divers.* 1:165–176, 1996). Similarly, the ligand library is cloned into M13 type 8 or 88 vector for fusion to the gene VIII protein (Roberts et al., *Methods Enzymol.* 267:68–82, 1996; Markland et al., *Gene* 109:13–19, 1991).

Candidate cell targets are seeded into 6-well culture plates at about 40,000 cells/well. At 24 hours after seeding cells, phage are added at ~$10^{10}$ pfu/ml. The plates are incubated at 37° C. for an additional 72 hours. Following incubation with the phage library, the target cells are removed from the plate and sorted for GFP expressing cells by FACS or directly lysed and the nucleic acid purified by passing over a sepharose 4B DNA affinity-column having conjugated thereto the lac repressor protein. Prior to affinity purification the cells are lysed and a nuclear extract is produced by following standard procedures, such as those described by Cull et al., *Proc. Nat'l. Acad. Sci. USA* 89:1865–1869, 1992; Schatz et al., *Methods in Enzymology* 267:171–191, 1996). The nuclear extract is then passed over the affinity column.

After applying to the column, the column is washed extensively with loading buffer (20 mM Tris-HCl pH 7.2) and eluted with a salt gradient. The resulting DNA containing fractions are pooled, amplified by PCR using the flanking gene III or gene VIII fusion sequences as primer templates, and subcloned back into a phagemid vector for further rounds of enrichment or alternatively for direct sequence characterization.

Example 23

Internalized Ligand Sequence Amplification by SV40 Shuttle Vector Transduction

The phagemid-shuttle vector includes the SV40 origin and packaging sequences, as well as SV40 capsid-encoding late genes under control of a promoter functional in target cells. This vector is created by PCR amplification of relevant sequences or direct restriction enzyme digestion and subcloning. These sequences can be obtained from commercially available vectors or wild-type virus. Similarly, the phage coat protein fusion, the phage origin and packaging

| Phage Prep | In/Out | Dilution factor | μl plated | plaques | Titer (pfu/ml) | Vol of prep (μl) | Phage recovered | Fraction of input |
| --- | --- | --- | --- | --- | --- | --- | --- | --- |
| TN10 library | In | 8 | 100 | 123 | 1.23E+08 | 5000 | 6.15E+11 | |
| TN10 nuclear | Out | 0 | 10 | 127 | 1.27E+01 | 400 | 5.08E+03 | 8.26E−09 |

Example 21

Ligand Selection Via Nucleic Acid Binding Domains

A phage library comprising a number of ligand displaying phage are created using a lac operon containing phagemid. The phagemid can be either a reporter gene containing phage (e.g., MEGFP3) or a non-reporter gene containing sequences, and bacterial selection markers can be assembled from current phage vectors.

Phage particles expressing a library of ligands as genetic fusions on the coat proteins (gIII or gVIII) are generated by rescuing phagemid containing bacteria with a helper phage, such that the phagemid genome is packaged into the phage particle expressing the ligand which is encoded by that genome. A target cell line containing the SV40 T antigens (either transfected or provided in trans with the VP22 fusion protein as a delivery vehicle) is incubated with the phage particles. Those particles expressing the appropriate ligands deliver the phagemid DNA to the nucleus. Due to the presence of the large T antigen in the cells and the SV40 origin, the DNA replicates. The dsDNA is then packaged into SV40 viral particles due to the presence of the capsid proteins encoded by the SV40 genes also carried on the phagemid genome. The SV40 particles carrying the phagemid then infect other neighboring cells and thus amplifying the internalized ligands until the whole population of cells is infected. Eventually, in all permissive cells are lysed due to viral production. Viral particles are harvested from the supernatants and the DNA they contain is analyzed by sequencing to determine the sequence of the ligand responsible for the initial internalization.

Example 24

Figure 14:
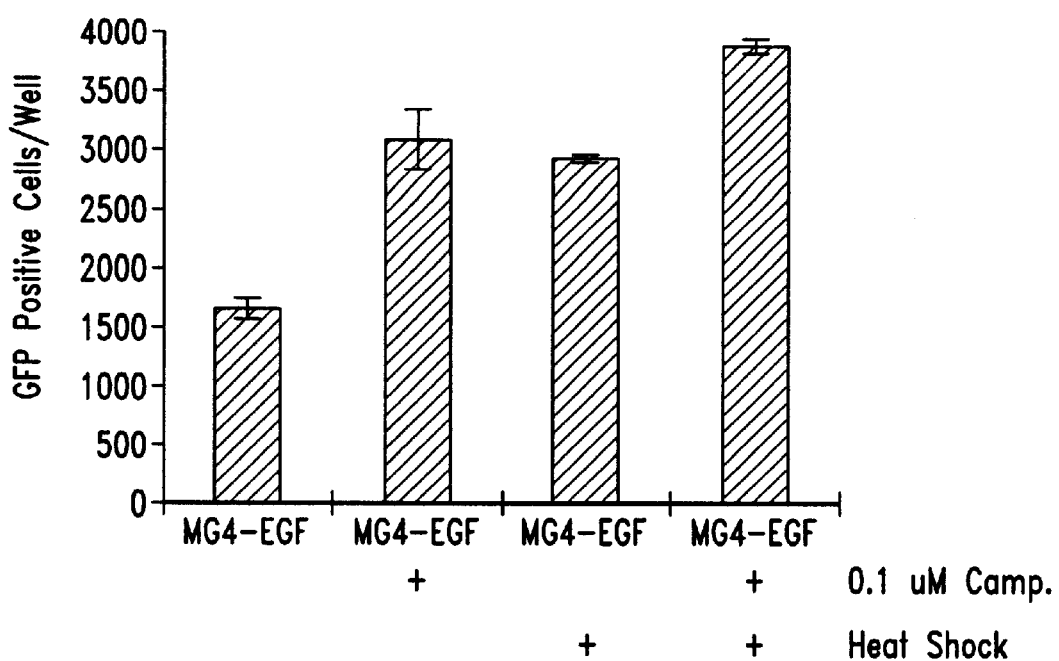
FIG. 14 is a bar graph depicting the effects on transduction following genotoxic treatment and/or heat shock treatment of target cells.

Enhancement of Target Cell Transduction Using Heat Shock and/or Genotoxic Treatment The effects of heat shock and another genotoxic treatment, camptothecin were tested. Camptothecin is a type I topoisomerase inhibiter that produces DNA strand breaks. Camptothecin is found to enhance transduction efficiency up to 2 fold at 0.1 $\mu$M but was inhibitory at higher concentrations (data not shown). EGF displaying phage (MG4-EGF vector) were incubated with COS cells for 24 hours at which time the cells were either not further treated, subjected to a four hour heat shock (42.5° C.), or treated with 0.1 $\mu$M camptothecin for four hours. GFP autofluorescent cells were counted at 72 hours after addition of phage. As depicted in FIG. 14 the results indicate about a 2 fold enhancement of targeted phage mediated transduction with either heat shock or camptothecin. The combination of both treatments resulted in a modest synergistic increase in efficiency over either treatment alone.

Example 25

Enhancement of Transduction Utilizing Endosomal Escape Peptide Display

The addition of endosomal escape peptides that are derived from minimal peptide sequences needed for viral endosome escape have been shown to enhance non-viral delivery of condensed DNA (Sosnowski et al., *J. Biol. Chem.* 271:33647–33653, 1996). Accordingly, such endosomal sequences were tested with the ligand display system described herein. Endosomal escape peptide fusions to pIII that are in-frame with both the EGF gene and the pIII gene were constructed. The sequence MAEGLFEAIEGFIENG-WEGMIDGWYG (SEQ ID NO: 15)(adapted from the INF7 N-terminal sequence of the influenza virus X-31 hemagglutinin subunit HA-2) was added to the N-terminus of EGF in MG4-EGF or pIII in MG4. This sequence is identical to the endosome disruptive peptide (INF7) described by Plank et al. (*J. Biol. Chem.* 269:12918–12924, 1994) except for the addition of the MAE tripeptide at the N-terminus. It is encoded on 2 overlapping oligonucleotides that are annealed and ligated into the Nco1 site in the MG4 and MG4-EGF vectors.

Figure 15:
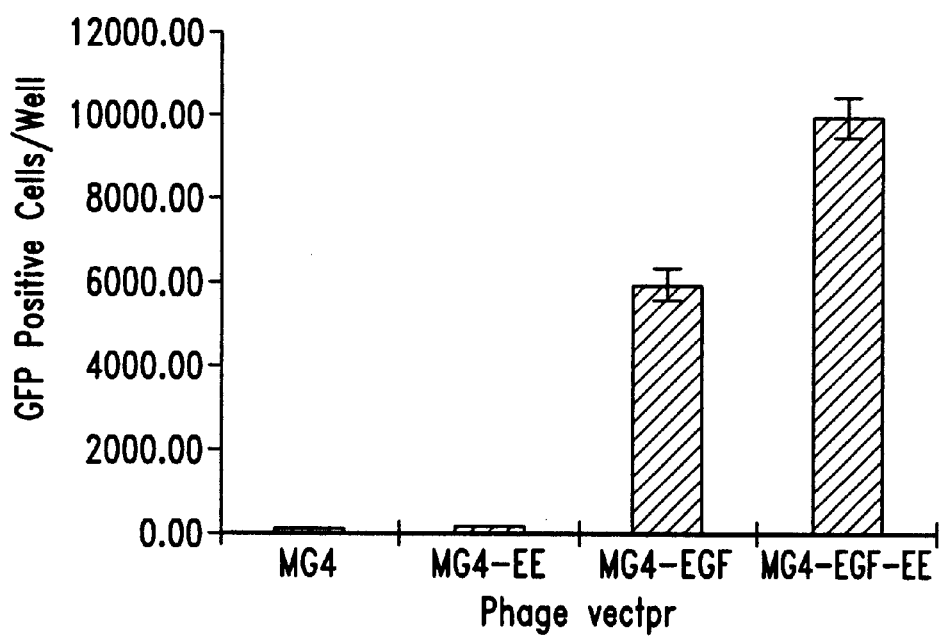
FIG. 15 is a bar graph representing the effects on transduction following display of an endosomal escape peptide.

The INF7 containing phage were tested on COS cells to determine transduction efficiency. The results (FIG. 15) show that transduction efficiency is increased about 1.8 fold with the addition of the INF7 sequence relative to the unmodified MG4-EGF phage. The addition of the INF7 sequence in the control phage has no effect on the background levels of transduction observed when transfecting COS1 cells with this phage at a titer of $10^{11}$ pfu/ml. Thus, an endosomal disruptive peptide enhances the ability of targeted phage to transduce COS1 cells when presented on the N-terminus of the EGF-pIII coat fusion protein.

Example 26

Figure 16:
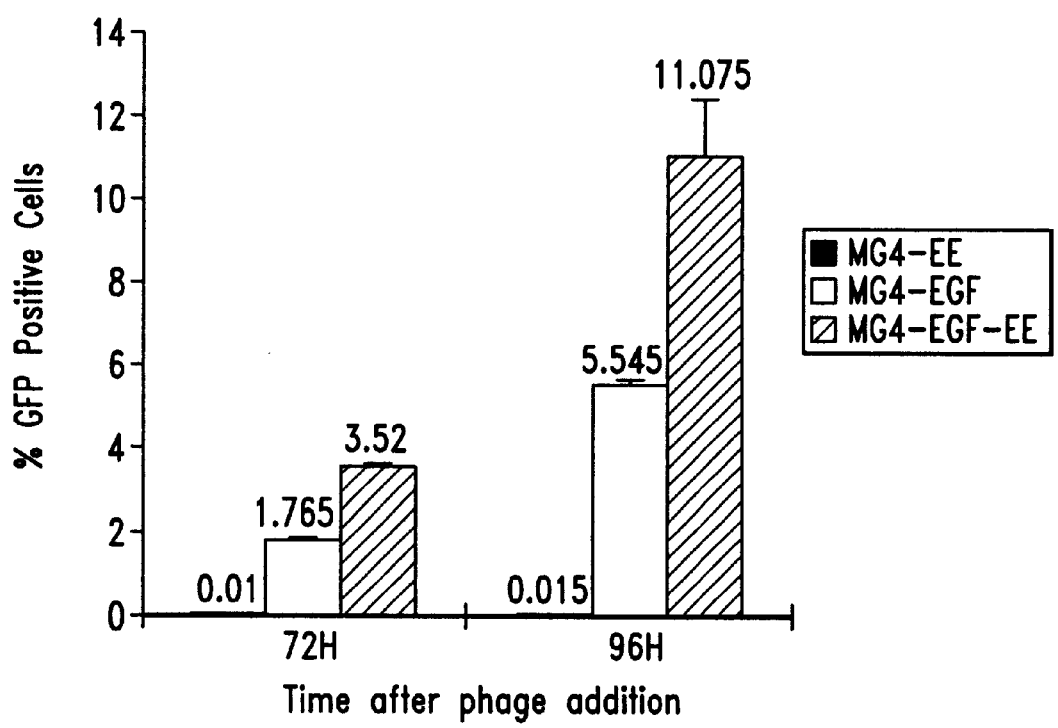
FIG. 16 is a bar graph displaying the combined effect of heat shock and display of an endosomal escape peptide on transduction.

Enhancement of Transduction Utilizing Endosomal Escape Peptide Display and Heat Shock The effect of both heat shock and the addition of an endosomal escape peptide were tested in combination to determine whether they effect distinct aspects of the transduction pathway and to test the limits of phage mediated transduction. EGF-phage (MG4-EGF), EGF-phage co-displaying an endosomal escape peptide (INF7 as above) (MG4-EGF-EE) or control phage (MG4) were added to COS1 cells at a titer of about $10^{11}$ pfu/ml and incubated for 72 or 96 hours. Cells were subjected to a seven hour heat shock (42.5° C.) at 40 hours after phage addition. The percentage of GFP positive cells was determined by FACS analysis. The results (FIG. 16) show that the effects of heat shock (HS) and the addition of the endosomal escape (EE) sequence are additive. At 72 hours after phage addition, the combination of HS and the EE sequence results in transduction efficiency of 3.5% and at 96 hours in about 11% transduction efficiency. At both time points the addition of the EE peptide results in about 2× the efficiency compared to heat shock alone. The highest transduction efficiency we observe in the absence of HS or the EE peptide is about 2% at 96 hours.

Example 27

Construction of Dual Display Vector

The pIII/pVIII dual display vector is constructed by the insertion of a pVIII encoding open reading frame down stream from the stop codon of pIII in a pIII-fusion phagemid vector (e.g., pUC-MG4 (FIG. 17)). This is accomplished by amplifying the mature gVIII gene from MG4 phage using primers that contain EcoR1 restriction endonuclease extensions on their ends.

The DNA sequence encoding the Eco R1 insert for making dual display vector encodes the pEL B Signal Peptide and gVIII gene with restriction enzyme sites Sst II, XhoI and BamH1 for insertion of peptide fusion s to gene VIII.

DNA

GAATTCATGAAATACCTATTGCCTACGGCCGCAGCAGGTCTCCTCCTCTTAGCAGCAC

AACCAGCAATGGCCGCGGAGTGACTCGAGGATCCCGCAAAAGCGGCCTTTAACTCCCT

GCAAGCCTCAGCGACCGAATATATCGGTTATGCGTGGGCGATGGTTGTTGTCATTGTC

GGCGCAACTATCGGTATCAAGCTGTTTAAGAAATTCACCTCGAAAGCAAGCTGATAAG

AATTC (SEQ ID NO: 16)

Protein translation:

MKYLLPTAAAGLLLLAAQPAMAAE.LEDPAKAAFNSLQASATEYIGYAWAMVVVIVGA

TIGIKLFKKFTSKAS (SEQ ID NO: 17)

"." = STOP CODON
pEL B leader is in bold type

Figure 18:
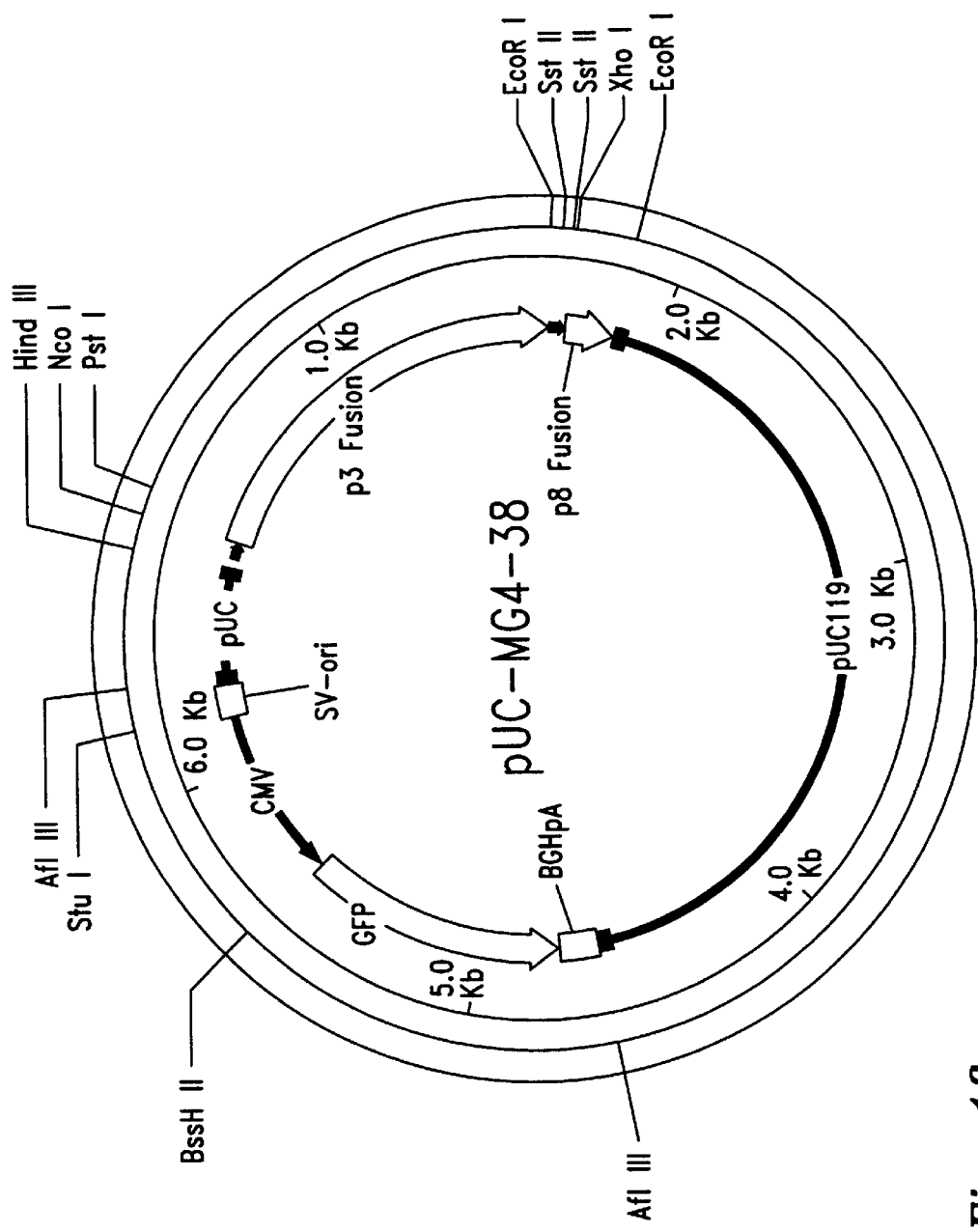
FIG. 18 is a vector map of a pUC-MG4–38 dual display vector.

The forward primer contains an additional extension that encodes the pe1B secretion signal peptide (Power et al., *Gene* 113:95–99, 1992) and restriction sites (SstII, XhoI, BamH1) for insertion of peptide or protein encoding fusions in-frame with the pVIII gene. There is an in-frame stop codon at the 5' end of the pVIII gene such that no pVIII protein is translated unless a peptide or protein encoding sequence is inserted in-frame near the sequences encoding the N-terminus of pVIII. The resulting PCR product is digested with EcoR1 and inserted into the EcoR1 site of the phagemid vector forming a bicistronic message encoding pIII followed by pVIII, both of which are regulated by the lac promoter upstream from the 2 consecutive open reading frames. (See FIG. 18)

From the foregoing it will be appreciated that, although specific embodiments of the invention have been described herein for purposes of illustration, various modifications may be made without deviating from the spirit and scope of the invention. Accordingly, the invention is not limited except as by the appended.

---

We claim:

1. A method of selecting ligands displayed on a phage that internalize and facilitate transgene expression, comprising:
   (a) contacting one or more ligand displaying phage with a cell(s), wherein said phage carry a transgene encoding a detectable product which is expressed upon internalization of the phage, and
   (b) detecting product expressed by the cell(s) and encoded by the transgene;
   (c) recovering a nucleic acid molecule encoding an internalizing ligand from the cell(s) expressing the detectable product by polymerase chain reaction (PCR) or Hirt extraction, and
   thereby selecting a ligand displayed on a phage that internalize and facilitate transgene expression.

2. The method of claim 1, further comprising isolating the cell(s) that express the detectable product.

3. The method of claim 2, wherein the cell(s) are isolated by flow cytometry.

4. The method of claim 1, wherein the ligand displaying phage comprise a library of ligand displaying phage.

5. The method of claim 4, wherein the library is a cDNA library.

6. The method of claim 4, wherein the library is an antibody gene library.

7. The method of claim 4, wherein the library is a random peptide gene library.

8. The method of claim 4, wherein the library is a mutein library.

9. The method claim 1, wherein the detectable product is selected from the group consisting of green fluorescent protein, β-galactosidase, secreted alkaline phosphatase, chloramphenicol acetyltransferase, luciferase, human growth hormone and neomycin phosphotransferase.

10. The method of claim 1, wherein the phage are filamentous phage.

11. The method of claim 10, wherein the phase carries a genome vector.

12. The method of claim 10, wherein the phage carries a hybrid vector.

13. The method of claim 12, wherein the hybrid vector comprises AAV or SV40 genome nucleic acid sequences.

14. A high throughput method of identifying a ligand displayed on a phage that internalizes and facilitates transgene expression, comprising;
   (a) contacting one or more ligand displaying phage with a cell(s) in an array, wherein said phage carry a transgene encoding at least one detectable product which is expressed upon internalization of the phage; and
   (b) detecting product(s) expressed by the cell(s) in the array, and
   thereby identifying a ligand displayed on a phage that internalizes and facilitates transgene expression.

15. The method of claim 14, further comprising recovering a nucleic acid molecule encoding a ligand from the cells expressing the product by PCR or Hirt extraction.

16. The method of claim 14, wherein the ligand displaying phage comprises a library of ligand displaying phage.

17. The method of claim 16, wherein the library is a cDNA library.

18. The method of claim 16, wherein the library is an antibody gene library.

19. The method of claim 16, wherein the library is a random peptide gene library.

20. The method of claim 16, wherein the library is a mutein library.

21. The method of claim 14, wherein the detectable product is selected from the group consisting of green fluorescent protein, β-galactosidase, secreted alkaline phosphatase, chloramphenicol acetyltransferase, luciferase, human growth hormone and neomycin phosphotransferase.

22. The method of claim 14, wherein the phage are filamentous phage.

23. The method of claim 14, wherein the phage are lambdoid phage.

24. The method of claim 14, wherein the phage carries a hybrid vector.

25. The method of claim 24, wherein the hybrid vector comprises SV40 O or AAV genome nucleic acid sequences.

26. The method of claim 14, wherein the phase carries a genome vector.

27. The method of any one of claims 1 or 14, further comprising contacting the cells with a genotoxic agent.

28. The method of any one of claims 1 or 14, further comprising subjecting the cells to heat shock.

29. The method of any one of claims 1 or 14, further comprising contacting the cells with a genotoxic agent and subjecting the cells to heat shock.

30. The method of any one of claims 1 or 14, wherein said phage displays at least two differing heterologous sequences on its surface.

31. The method of any one of claims 1 or 14, wherein the phage comprise phagemid particles.

32. The method of claim 31, wherein said phagemid are multivalent for the ligand.

33. The method of claim 31, wherein the phagemid are monovalent for the ligand.

* * * * *

UNITED STATES PATENT AND TRADEMARK OFFICE
CERTIFICATE OF CORRECTION

PATENT NO. : 6,723,512 B2 Page 1 of 1
DATED : April 20, 2004
INVENTOR(S) : David Larocca et al.

It is certified that error appears in the above-identified patent and that said Letters Patent is hereby corrected as shown below:

Column 57,
Line 38, "phase" should read as -- phage --

Column 58,
Line 31, "SV40 O" should read as -- SV40 --
Line 32, "phase" should read as -- phage --

Signed and Sealed this

Ninth Day of August, 2005

JON W. DUDAS
*Director of the United States Patent and Trademark Office*

SEQUENCE LISTING

```
<160> NUMBER OF SEQ ID NOS: 18

<210> SEQ ID NO 1
<211> LENGTH: 10
<212> TYPE: PRT
<213> ORGANISM: Unknown
<220> FEATURE:
<223> OTHER INFORMATION: Description of Unknown Organism:  A screened
      peptide, from a random peptide library, that binds
      and internalizes in a FGF receptor overproducing
      cell line

<400> SEQUENCE: 1

Phe Val Pro Asp Pro Tyr Arg Lys Ser Arg
1               5                   10

<210> SEQ ID NO 2
<211> LENGTH: 10
<212> TYPE: PRT
<213> ORGANISM: Unknown
<220> FEATURE:
<223> OTHER INFORMATION: Description of Unknown Organism:  A screened
      peptide, from a random peptide library, that binds
      and internalizes in a FGF receptor overproducing
      cell line

<400> SEQUENCE: 2

Cys Gly Gly Gly Pro Val Ala Gln Arg Cys
1               5                   10

<210> SEQ ID NO 3
<211> LENGTH: 10
<212> TYPE: PRT
<213> ORGANISM: Unknown
```

```
<220> FEATURE:
<223> OTHER INFORMATION: Description of Unknown Organism:  A screened
      peptide, from a random peptide library, that binds
      and internalizes in a FGF receptor overproducing
      cell line

<400> SEQUENCE: 3

Cys Leu Ala His Pro His Gly Gln Arg Cys
 1               5                  10

<210> SEQ ID NO 4
<211> LENGTH: 4
<212> TYPE: PRT
<213> ORGANISM: Unknown
<220> FEATURE:
<223> OTHER INFORMATION: Consensus nuclear localization sequence
<220> FEATURE:
<221> NAME/KEY: VARIANT
<222> LOCATION: (2)...(3)
<223> OTHER INFORMATION: Xaa = Any amino acid
<220> FEATURE:
<221> NAME/KEY: VARIANT
<222> LOCATION: (4)...(4)
<223> OTHER INFORMATION: Xaa = Lysine or Arginine

<400> SEQUENCE: 4

Lys Xaa Xaa Xaa

<210> SEQ ID NO 5
<211> LENGTH: 47
<212> TYPE: DNA
<213> ORGANISM: Artificial Sequence
<220> FEATURE:
<223> OTHER INFORMATION: PCR Primer

<400> SEQUENCE: 5
aaaggatccg ggttcccgcg tgggcgatgg ttgttgtcat tgtcggc                    47

<210> SEQ ID NO 6
<211> LENGTH: 25
<212> TYPE: DNA
<213> ORGANISM: Artificial Sequence
<220> FEATURE:
<223> OTHER INFORMATION: PCR Primer

<400> SEQUENCE: 6
ccgtaacact gagtttcgtc accag                                            25

<210> SEQ ID NO 7
<211> LENGTH: 30
<212> TYPE: DNA
<213> ORGANISM: Artificial Sequence
<220> FEATURE:
<223> OTHER INFORMATION: PCR Primer

<400> SEQUENCE: 7
gcgtgggcga tggttgttgt cattgtcggc                                       30

<210> SEQ ID NO 8
<211> LENGTH: 25
<212> TYPE: DNA
<213> ORGANISM: Artificial Sequence
<220> FEATURE:
<223> OTHER INFORMATION: PCR Primer

<400> SEQUENCE: 8
ccacagacaa ccctcatagt tagcg                                            25
```

```
<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
ttttggagat tttcaacgtg                                                      20

<210> SEQ ID NO 10
<211> LENGTH: 20
<212> TYPE: DNA
<213> ORGANISM: Artificial Sequence
<220> FEATURE:
<223> OTHER INFORMATION: PCR Primer

<400> SEQUENCE: 10
tgctaaacaa ctttcaacag                                                      20

<210> SEQ ID NO 11
<211> LENGTH: 4
<212> TYPE: PRT
<213> ORGANISM: Unknown
<220> FEATURE:
<223> OTHER INFORMATION: Lysosomal directing sequence

<400> SEQUENCE: 11

Lys Cys Pro Leu
 1

<210> SEQ ID NO 12
<211> LENGTH: 10
<212> TYPE: PRT
<213> ORGANISM: Unknown
<220> FEATURE:
<223> OTHER INFORMATION: Lysosomal directing sequence

<400> SEQUENCE: 12

Asp Ser Trp Val Glu Phe Ile Glu Leu Asp
 1               5                  10

<210> SEQ ID NO 13
<211> LENGTH: 6
<212> TYPE: PRT
<213> ORGANISM: Unknown
<220> FEATURE:
<223> OTHER INFORMATION: Lysosomal directing sequence

<400> SEQUENCE: 13

Asp Gln Arg Asp Leu Ile
 1               5

<210> SEQ ID NO 14
<211> LENGTH: 6
<212> TYPE: PRT
<213> ORGANISM: Unknown
<220> FEATURE:
<223> OTHER INFORMATION: Lysosomal directing sequence

<400> SEQUENCE: 14

Glu Gln Leu Pro Met Leu
 1               5

<210> SEQ ID NO 15
<211> LENGTH: 26
```

```
<212> TYPE: PRT
<213> ORGANISM: Artificial Sequence
<220> FEATURE:
<223> OTHER INFORMATION: Endosomal escape peptide adapted from the INF7
      N-terminal sequence of the influenza virus X-31
      hemagglutinin subunit HA-2.

<400> SEQUENCE: 15

Met Ala Glu Gly Leu Phe Glu Ala Ile Glu Gly Phe Ile Glu Asn Gly
 1               5                  10                  15

Trp Glu Gly Met Ile Asp Gly Trp Tyr Gly
            20                  25

<210> SEQ ID NO 16
<211> LENGTH: 237
<212> TYPE: DNA
<213> ORGANISM: Artificial Sequence
<220> FEATURE:
<223> OTHER INFORMATION: Dual display vector

<400> SEQUENCE: 16
gaattcatga ataacctatt gcctacggcc gcagcaggtc tcctcctctt agcagcacaa       60
ccagcaatgg ccgcggagtg actcgaggat cccgcaaaag cggcctttaa ctccctgcaa      120
gcctcagcga ccgaatatat cggttatgcg tgggcgatgg ttgttgtcat tgtcggcgca      180
actatcggta tcaagctgtt taagaaattc acctcgaaag caagctgata agaattc         237

<210> SEQ ID NO 17
<211> LENGTH: 72
<212> TYPE: PRT
<213> ORGANISM: Artificial Sequence
<220> FEATURE:
<223> OTHER INFORMATION: Protein translation of dual display vector

<400> SEQUENCE: 17

Met Lys Tyr Leu Leu Pro Thr Ala Ala Ala Gly Leu Leu Leu Leu Ala
 1               5                  10                  15

Ala Gln Pro Ala Met Ala Ala Glu Leu Glu Asp Pro Lys Ala Ala
            20                  25                  30

Phe Asn Ser Leu Gln Ala Ser Ala Thr Glu Tyr Ile Gly Tyr Ala Trp
        35                  40                  45

Ala Met Val Val Val Ile Val Gly Ala Thr Ile Gly Ile Lys Leu Phe
    50                  55                  60

Lys Lys Phe Thr Ser Lys Ala Ser
65                  70

<210> SEQ ID NO 18
<211> LENGTH: 6
<212> TYPE: PRT
<213> ORGANISM: Unknown
<220> FEATURE:
<223> OTHER INFORMATION: Heparin binding consensus
<220> FEATURE:
<221> NAME/KEY: VARIANT
<222> LOCATION: 3,6
<223> OTHER INFORMATION: Xaa = any amino acid

<400> SEQUENCE: 18

Arg Arg Xaa Arg Arg Xaa
 1               5
```